United States Patent
Cutshall et al.

(10) Patent No.: US 9,102,643 B2
(45) Date of Patent: Aug. 11, 2015

(54) PDE10 INHIBITORS AND RELATED COMPOSITIONS AND METHODS

(71) Applicant: Omeros Corporation, Seattle, WA (US)

(72) Inventors: Neil S. Cutshall, Snohomish, WA (US); Jennifer Lynn Gage, Kenmore, WA (US); Thomas Neil Wheeler, Raleigh, NC (US); Thomas L. Little, Redmond, WA (US)

(73) Assignee: OMEROS CORPORATION, Seattle, WA (US)

( * ) Notice: Subject to any disclaimer, the term of this patent is extended or adjusted under 35 U.S.C. 154(b) by 0 days.

(21) Appl. No.: 14/177,952

(22) Filed: Feb. 11, 2014

(65) Prior Publication Data

US 2014/0228581 A1  Aug. 14, 2014

Related U.S. Application Data

(63) Continuation of application No. 13/679,818, filed on Nov. 16, 2012, now Pat. No. 8,685,975, which is a continuation of application No. 13/045,162, filed on Mar. 10, 2011, now Pat. No. 8,343,970.

(60) Provisional application No. 61/430,841, filed on Jan. 7, 2011, provisional application No. 61/313,544, filed on Mar. 12, 2010.

(51) Int. Cl.
| | | |
|---|---|---|
| *C07D 307/34* | (2006.01) |
| *C07D 307/40* | (2006.01) |
| *C07D 231/12* | (2006.01) |
| *C07D 401/04* | (2006.01) |
| *C07D 405/10* | (2006.01) |
| *C07D 413/10* | (2006.01) |
| *C07D 417/10* | (2006.01) |
| *A61K 31/341* | (2006.01) |
| *A61K 31/415* | (2006.01) |
| *A61K 31/4155* | (2006.01) |
| *A61K 31/4192* | (2006.01) |
| *A61K 31/4196* | (2006.01) |
| *A61K 31/421* | (2006.01) |
| *A61K 31/422* | (2006.01) |
| *A61K 31/4245* | (2006.01) |
| *A61K 31/427* | (2006.01) |
| *A61K 31/433* | (2006.01) |
| *A61K 31/454* | (2006.01) |
| *A61K 31/4545* | (2006.01) |
| *A61K 31/4709* | (2006.01) |
| *A61K 31/497* | (2006.01) |
| *A61K 31/5377* | (2006.01) |
| *C07D 285/12* | (2006.01) |

(52) U.S. Cl.
CPC ............ *C07D 307/40* (2013.01); *A61K 31/341* (2013.01); *A61K 31/415* (2013.01); *A61K 31/4155* (2013.01); *A61K 31/4192* (2013.01); *A61K 31/4196* (2013.01); *A61K 31/421* (2013.01); *A61K 31/422* (2013.01); *A61K 31/427* (2013.01); *A61K 31/4245* (2013.01); *A61K 31/433* (2013.01); *A61K 31/454* (2013.01); *A61K 31/4545* (2013.01); *A61K 31/4709* (2013.01); *A61K 31/497* (2013.01); *A61K 31/5377* (2013.01); *C07D 231/12* (2013.01); *C07D 285/12* (2013.01); *C07D 307/34* (2013.01); *C07D 401/04* (2013.01); *C07D 405/10* (2013.01); *C07D 413/10* (2013.01); *C07D 417/10* (2013.01)

(58) Field of Classification Search
None
See application file for complete search history.

(56) References Cited

U.S. PATENT DOCUMENTS

2010/0035887 A1 * 2/2010 Ricciardi ...................... 514/250

* cited by examiner

*Primary Examiner* — Maury Audet
*Assistant Examiner* — Fred Reynolds
(74) *Attorney, Agent, or Firm* — Seed IP Law Group PLLC

(57) ABSTRACT

Compounds that inhibit PDE10 are disclosed that have utility in the treatment of a variety of conditions, including (but not limited to) psychotic, anxiety, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, drug-induced psychosis and panic and obsessive-compulsive disorders. Pharmaceutically acceptable salts, stereoisomers, solvates and prodrugs of the compounds are also provided. Also disclosed are compositions containing a compound in combination with a pharmaceutically acceptable carrier, as well as methods relating to the use thereof for inhibiting PDE10 in a warm-blooded animal in need of the same.

1 Claim, 10 Drawing Sheets

PDE10 INHIBITORS AND RELATED COMPOSITIONS AND METHODS

CROSS-REFERENCE TO RELATED APPLICATIONS

This application is a continuation of U.S. patent application Ser. No. 13/679,818, filed Nov. 16, 2012, which is a continuation of U.S. patent application Ser. No. 13/045,162, filed Mar. 10, 2011 (now U.S. Pat. No. 8,343,970), which claims the benefit under 35 U.S.C. §119(e) of U.S. Provisional Patent Application No. 61/313,544, filed Mar. 12, 2010, and U.S. Provisional Patent Application No. 61/430,841, filed Jan. 7, 2011, which applications are incorporated herein by reference in their entireties.

BACKGROUND

1. Technical Field

This invention relates generally to compounds having activity as PDE10 inhibitors, and to compositions containing the same, as well as to methods of treating various disorders by administration of such compounds to a warm-blooded animal in need thereof.

2. Description of the Related Art

Cyclic nucleotide phosphodiesterases (PDEs) are represented by a large superfamily of enzymes. PDEs are known to possess a modular architecture, with a conserved catalytic domain proximal to the carboxyl terminus, and regulatory domains or motifs often near the amino terminus. The PDE superfamily currently includes more than twenty different genes subgrouped into eleven PDE families (Lugnier, C., "Cyclic nucleotide phosphodiesterase (PDE) superfamily: a new target for the development of specific therapeutic agents." Pharmacol Ther. 2006 March; 109(3):366-98).

A recently described PDE, PDE10, was reported simultaneously by three independent groups (Fujishige et al., "Cloning and characterization of a novel human phosphodiesterase that hydrolyzes both cAMP and cGMP (PDE10A)," *J Biol Chem* 1999, 274:18438-18445; Loughney et al., "Isolation and characterization of PDE10A, a novel human 3',5'-cyclic nucleotide phosphodiesterase," *Gene* 1999, 234:109-117; Soderling et al., "Isolation and characterization of a dual-substrate phosphodiesterase gene family: PDE10A," *Proc Natl Acad Sci USA* 1999, 96:7071-7076). PDE10 has the capacity to hydrolyze both cAMP and cGMP; however, the $K_m$ for cAMP is approximately 0.05 µM, whereas the $K_M$ for cGMP is 3 µM. In addition, the $V_{max}$ for cAMP hydrolysis is fivefold lower than for cGMP. Because of these kinetics, cGMP hydrolysis by PDE10 is potently inhibited by cAMP in vitro, suggesting that PDE10 may function as a cAMP-inhibited cGMP phosphodiesterase in vivo. Unlike PDE8 or PDE9, PDE10 is inhibited by IBMX with an $IC_{50}$ (50% inhibitory concentration) of 2.6 µM. (See Soderling and Beavo, "Regulation of cAMP and cGMP signaling: new phosphodiesterases and new functions," *Current Opinion in Cell Biology,* 2000, 12:174-179.)

PDE10 contains two amino-terminal domains that are similar to the cGMP-binding domains of PDE2, PDE5 and PDE6, which are domains conserved across a wide variety of proteins. Because of the wide conservation of this domain, it is now referred to as the GAF domain (for the GAF proteins: cGMP binding phosphodiesterases; the cynobacterial *Anabaena* adenylyl cyclase; and the *Escherichia coli* transcriptional regulator fhlA). Although in PDE2, PDE5 and PDE6 the GAF domains bind cGMP, this is probably not the primary function of this domain in all cases (e.g., *E. coli* are not thought to synthesize cGMP). Interestingly, in vitro binding studies of PDE10 indicate the dissociation constant ($K_d$) for cGMP binding is well above 9 µM. As in vivo concentrations of cGMP are not thought to reach such high levels in most cells, it seems likely that either the affinity of PDE10 for cGMP is increased by regulation, or that the primary function of the GAF domain in PDE10 may be for something other than cGMP binding.

Inhibitors of the PDE family of enzymes have widely been sought for a broad indication of therapeutic uses. Reported therapeutic uses of PDE inhibitors include allergies, obtrusive lung disease, hypertension, renal carcinoma, angina, congestive heart failure, depression and erectile dysfunction (WO 01/41807 A2). Other inhibitors of PDE have been disclosed for treatment of ischemic heart conditions (U.S. Pat. No. 5,693,652). More specifically, inhibitors of PDE10 have been disclosed for treatment of certain neurological and psychiatric disorders including, Parkinson's disease, Huntington's disease, schizophrenia, delusional disorders, drug-induced psychosis and panic and obsessive-compulsive disorders (U.S. Patent Application No. 2003/0032579). PDE10 has been shown to be present at high levels in neurons in areas of the brain that are closely associated with many neurological and psychiatric disorders. By inhibiting PDE10 activity, levels of cAMP and cGMP are increased within neurons, and the ability of these neurons to function properly is thereby improved. Thus, inhibition of PDE10 is believed to be useful in the treatment of a wide variety of conditions or disorders that would benefit from increasing levels of cAMP and cGMP within neurons, including those neurological, psychotic, anxiety and/or movement disorders mentioned above.

While advances have been made with regard to inhibition of PDE10, there remains a need in the field for inhibitors of PDE10, as well as the need to treat various conditions and/or disorders that would benefit from the same.

BRIEF SUMMARY

In brief, this invention is generally directed to compounds that have activity as PDE10 inhibitors, as well as to methods for their preparation and use, and to pharmaceutical compositions containing the same.

In one embodiment, the compounds have the following general structure (I):

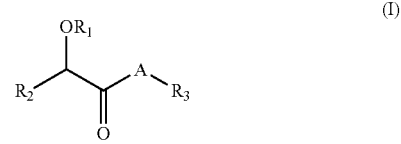

including pharmaceutically acceptable salts, stereoisomers, solvates and prodrugs thereof, wherein A, $R_1$, $R_2$ and $R_3$ are as defined below.

The compounds of this invention have utility over a wide range of therapeutic applications, and may be used to treat a wide variety of conditions or disorders that would benefit from increasing levels of cAMP and cGMP, especially within neurons, including (but not limited to) neurological disorders, such as psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis.

The methods of this invention include administering an effective amount of a compound of the foregoing structures, typically in the form of a pharmaceutical composition, to a mammal in need thereof, including a human. Thus, in a further embodiment, pharmaceutical compositions are disclosed containing one or more compounds of the foregoing structures in combination with a pharmaceutically acceptable carrier or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Figure 1:
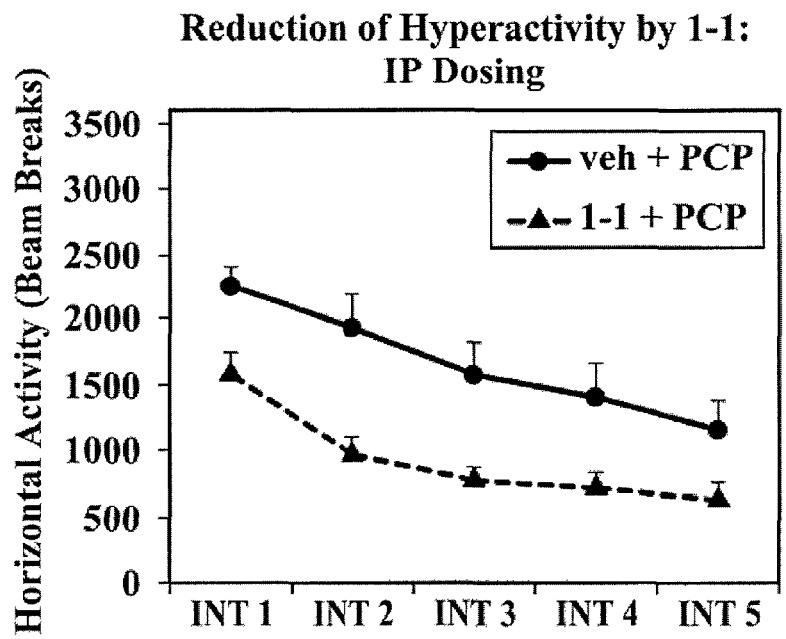
FIG. 1 illustrates that Compound 1-1 of the present invention (Example 1) administered by intraperitoneal injection significantly reduces hyperactivity of mice in a psychostimulant (PCP)-induced model of psychosis as compared to vehicle control.

As mentioned above, the present invention is directed generally to compounds useful as PDE10 inhibitors, as well as to methods for their preparation and use, and to pharmaceutical compositions containing the same.

In one embodiment, the PDE10 inhibitors have the following structure (I):

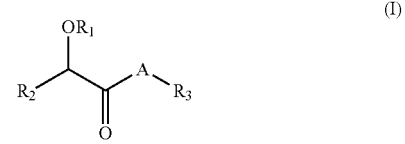

or a pharmaceutically acceptable salt, stereoisomer, solvate or prodrug thereof,
wherein:
A is:

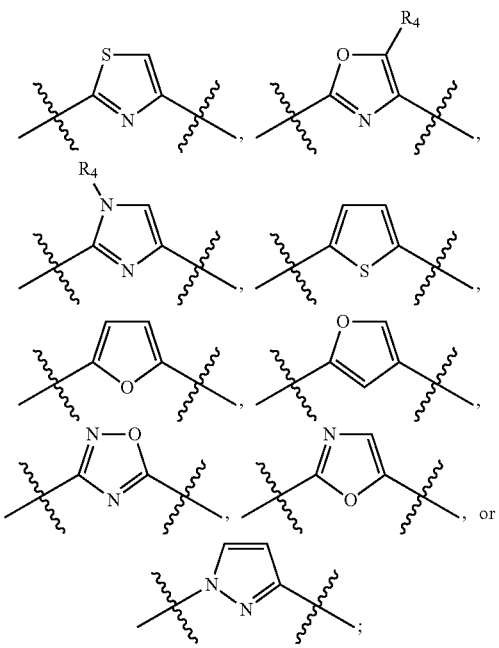

$R_1$ is $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;
$R_2$ is (i) substituted or unsubstituted aryl or (ii) substituted or unsubstituted heterocyclyl;
$R_3$ is substituted or unsubstituted aryl;
$R_4$ is hydrogen, $C_{1-6}$alkyl or $C_{1-6}$haloalkyl;
n is 1, 2, 3, 4, 5 or 6; and
m is 0, 1, 2, 3, 4, 5 or 6.

As used herein, the above terms have the following meaning:

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.

"$C_{1-6}$alkyl" means a straight chain or branched, noncyclic or cyclic, unsaturated or saturated aliphatic hydrocarbon radical containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-6}$alkylene" or "$C_{1-6}$alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to six carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain.

"$C_{1-6}$alkoxy" refers to a radical of the formula —OR$_a$ where R$_a$ is an alkyl radical as defined above, for example, methoxy, ethoxy and the like.

"Aryl" means a hydrocarbon ring system radical comprising hydrogen, 6 to 18 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

"$C_{1-6}$aralkyl" means a radical of the formula —R$_b$-R$_c$, where R$_b$ is an alkylene chain as defined above and R$_c$, is one or more aryl radicals as defined above, for example, benzyl, diphenylmethyl and the like.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Halo" or "halogen" refers to bromo, chloro, fluoro or iodo.

"$C_{1-6}$haloalkyl" refers to a $C_{1-6}$alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocycle" or "heterocyclyl" means a 4- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. An aromatic heterocycle is referred to herein as a "heteroaryl", and includes (but is not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, oxadiazolyl, thiadiazolyl, benzisoxazolyl, triazolyl, tetrazolyl, indazolyl and quinazolinyl. In addition to the heteroaryls listed above, heterocycles also include morpholinyl, pyrrolidinonyl, pyrrolidinyl, piperidinyl, piperazinyl, and the like. In addition, heterocycles also include benzothiophen-2-yl, 2,3-dihydrobenzo-1,4-dioxin-6-yl, benzo-1,3-dioxol-5-yl and the like.

The term "substituted" as used herein (for example, in the context of a substituted heterocyclyl or substituted aryl) means that at least one hydrogen atom is replaced with a substituent. "Substituents" within the context of this invention include halogen, hydroxy, oxo, cyano, nitro, imino, thioxo, amino, alkylamino, dialkylamino, alkyl, alkoxy, alkylthio, haloalkyl, aryl, aralkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$—NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$, —S(=O)$_2$OR$_a$, =NSO$_2$R$_a$ and —SO$_2$NR$_a$R$_b$. In the foregoing, R$_a$ and R$_b$ in this context may be the same or different and independently hydrogen, alkyl, haloalkyl, cycloalkyl, aryl, aralkyl, heterocyclyl. In addition, the foregoing substituents may be further substituted with one or more of the above substituents.

In further embodiments of structure (I), the compound has the following structure (I-A):

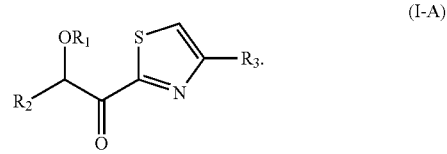

(I-A)

In other further embodiments of structure (I), the compound has the following structure (I-B):

(I-B)

In other further embodiments of structure (I), the compound has the following structure (I-C):

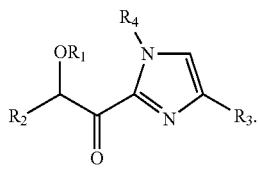

(I-C)

In other further embodiments of structure (I), the compound has the following structure (I-D):

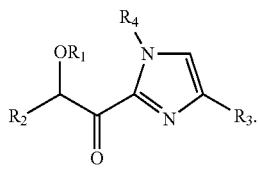

(I-D)

In other further embodiments of structure (I), the compound has the following structure (I-E):

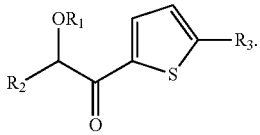

(I-E)

In other further embodiments of structure (I), the compound has the following structure (I-F):

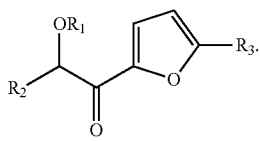

(I-F)

In other further embodiments of structure (I), the compound has the following structure (I-G):

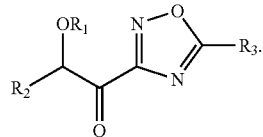

(I-G)

In other further embodiments of structure (I), the compound has the following structure (I-H):

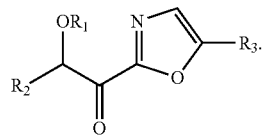

(I-H)

In other further embodiments of structure (I), the compound has the following structure (I-I):

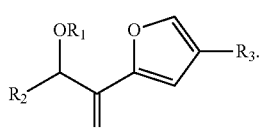

(I-I)

In other further embodiments of structure (I), in particular, structures (I-B) and (I-C), $R_4$ is hydrogen or $R_4$ is $C_{1-6}$alkyl (such as, for example, methyl).

In other further embodiments of structure (I), $R_1$ is $C_{1-6}$alkyl (such as, for example, $R_1$ is methyl or ethyl).

In other further embodiments of structure (I), $R_3$ is substituted or unsubstituted phenyl (such as, for example, 4-bromo-3,5-dimethoxyphenyl, 4-chloro-3,5-dimethoxyphenyl or 3,4,5-trimethoxyphenyl).

In other further embodiments of structure (I), $R_2$ is substituted or unsubstituted aryl, such as substituted or unsubstituted phenyl. In more specific embodiments, wherein $R_2$ is substituted phenyl, $R_2$ is phenyl substituted with $C_{1-6}$ alkoxy, or $R_2$ is phenyl substituted with substituted or unsubstituted heterocyclyl (such as, for example, 4-(5-methyl-1,3,4-oxadiazol-2-yl)phenyl, 4-(5-methyl-1,3,4-thiadiazol-2-yl)phenyl or 4-morpholinophenyl).

In other further embodiments of structure (I), $R_2$ is substituted or unsubstituted heterocyclyl.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}C$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment of the invention, pharmaceutical compositions containing one or more compounds of structure (I) are disclosed. For the purposes of administration, the compounds of the present invention may be formulated as pharmaceutical compositions. Pharmaceutical compositions of the present invention comprise one or more compounds of the present invention and a pharmaceutically acceptable carrier and/or diluent. The PDE10 inhibitor is present in the composition in an amount which is effective to treat a particular disorder—that is, in an amount sufficient to achieve desired PDE10 inhibition, and preferably with acceptable toxicity to the warm-blooded animal. Typically, the pharmaceutical compositions of the present invention may include a PDE10 inhibitor in an amount from 0.1 mg to 250 mg per dosage depending upon the route of administration, and more typically from 1 mg to 60 mg. Appropriate concentrations and dosages can be readily determined by one skilled in the art.

In general terms, a typical daily dosage might range from about 1 µg/kg to 100 mg/kg, preferably 0.01-100 mg/kg, more preferably 0.1-70 mg/kg, depending on the type and severity of the disease whether, for example, by one or more separate administrations. For repeated administrations over several days or longer, depending on the condition, the treatment is sustained until a desired suppression of disease symptoms occurs. However, other dosage regimens may be useful. The progress of this therapy can be monitored by standard techniques and assays. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a PDE10 inhibitor, diluents, dispersing and surface active agents, binders, and lubricants. One skilled in this art may further formulate the PDE10 inhibitor in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating diseases such as (but not limited to) psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis as discussed above. Such methods include administering of a compound of the present invention to a warm-blooded animal in an amount sufficient to treat the condition. In this context, "treat" includes prophylactic administration. Such methods include systemic administration of a PDE10 inhibitor of this invention, preferably in the form of a pharmaceutical composition as discussed above. As used herein, systemic administration includes oral and parenteral methods of administration, including subcutaneous, intramuscular, intracranial, intraorbital, ophthalmic, intraventricular, intracapsular, intraarticular, intraspinal, intracisternal, intraperitoneal, intranasal, aerosol, intravenous, intradermal, inhalational, transdermal, transmucosal, and rectal administration.

For oral administration, suitable pharmaceutical compositions of PDE10 inhibitors include powders, granules, pills, tablets, and capsules as well as liquids, syrups, suspensions, and emulsions. These compositions may also include flavorants, preservatives, suspending, thickening and emulsifying agents, and other pharmaceutically acceptable additives and excipients. For parenteral administration, the compounds of the present invention can be prepared in aqueous injection solutions which may contain, in addition to the PDE10 inhibitor, buffers, antioxidants, bacteriostats, and other additives and excipients commonly employed in such solutions. Compositions of the present invention may be carried in a delivery system to provide for sustained release or enhanced uptake or activity of the therapeutic compound, such as a liposomal or hydrogel system for injection, a microparticle, nanopartical or micelle system for oral or parenteral delivery, or a staged capsule system for oral delivery.

In a further advantage of the present invention, compounds of structure (I) are expected to avoid or reduce metabolic side effects associated with conventional antipsychotics, in particular the incidence of therapeutically induced obesity. For example, chronic use of olanzapine (Zyprexa®), the most widely prescribed medication to treat schizophrenia, and related atypical antipsychotics is associated with significant metabolic side effects including obesity and associated conditions such as diabetes.

In animals, subchronic treatment with olanzapine stimulates food intake and increases body weight, consistent with human situations. Furthermore, olanzapine acutely lowers blood leptin levels. Leptin is a satiety hormone produced from adipose tissues, and decrease of leptin level stimulates appetite. It is theorized that olanzapine could stimulate food intake at least partly by reducing leptin levels. Acute administration of olanzapine also changes the animal's response in glucose and insulin levels in glucose tolerance tests, which may also be directly linked to olanzapine's effect in food intake and body weight gain. Examination of the acute effect of PDE10 inhibitors of the present invention on metabolism, such as leptin, insulin and glucose changes during a metabolic challenge in standard animal models, as well as the chronic effect of PDE10 inhibitors of the present invention in food intake, body weight and energy homeostasis, in comparison with olanzapine should provide evidence to the pharmaceutical advantage of PDE10 inhibitors as antipsychotics in terms of less side-effect concerns.

The compositions of the present invention may be administered in combination with one or more additional therapeutic agents, in combination or by concurrent or sequential administration. Suitable additional agents (i.e., adjuvants) may include typical antipsychotics that block dopamine-$D_2$ receptors and serotonin $5HT_2$ receptors, e.g., haloperidol, fluphenazine, chlorpromazine, and atypical antipsychotics, e.g., clozapine, olanzapine, risperidone, quetiapine, ziprasidone.

Compounds of this invention may be assayed to determine their $IC_{50}$ values by a modification of the two-step method of Thompson and Appleman (*Biochemistry* 10; 311-316; 1971). In short, cAMP is spiked with ($^3$H) cAMP and incubated with PDE10 and various concentrations of a compound of structure (I). After the appropriate incubation time, the reaction is terminated by heating. The mixture is then subjected to treatment with snake venom phosphatase. The phosphatase hydrolyzes any AMP in the mixture, but leaves unreacted cAMP intact. Thus, by separating cAMP from the mixture and determining its concentration (by radiography), the percent of inhibition can be determined $IC_{50}$ values can be calculated by performing the experiment at several concentrations using standard graphical means. A detailed description of the actual technique used for $IC_{50}$ assays as set forth in following Examples. To this end, PDE10 inhibitors of the invention have an $IC_{50}$ of 100 µM or less, generally less than 10 µM, and typically less than 1 µM.

The compounds of the present invention may be prepared by known organic synthesis techniques, including the methods described in more detail in the following examples. The following examples are provided for purposes of illustration, not limitation.

EXAMPLES

Example 1

1-(4-(4-Bromo-3,5-Dimethoxyphenyl)Thiazol-2-yl)-2-Methoxy-2-(4-Morpholinophenyl)Ethanone

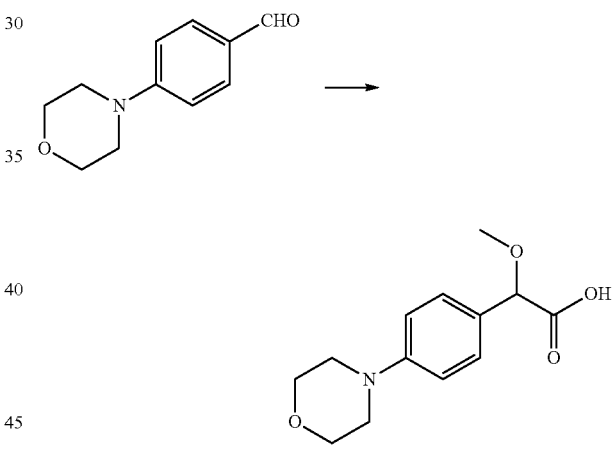

An oven-dried flask was charged with 4-(4-morpholinyl)benzaldehyde (10.1 g, 53 mmol), anhydrous methanol (60 mL) and anhydrous dioxane (60 mL) then fitted with an addition funnel. The addition funnel was charged with a solution of KOH (14.8 g, 264 mmol) in anhydrous methanol (60 mL) and an aliquot (~2 mL) was added to the reaction mixture. Bromoform (5.8 mL, 67.1 mmol) was added to the reaction mixture then the remaining KOH/MeOH solution was added dropwise over 10 minutes. After stirring for 18 h, the mixture was filtered through Celite and rinsed with methanol. The filtrate was collected and concentrated in vacuo. The residue was then diluted with saturated aqueous $NH_4Cl$ and extracted with EtOAc. Additional EtOAc was then used to extract the aqueous phase while slowly adjusting the pH from ~8 to ~2 using concentrated HCl. A total of approximately 1.5 L of EtOAc was used for the extraction process. The combined EtOAc extracts were dried over $Na_2SO_4$ and filtered. Concentration of the filtrate in vacuo gave 2-methoxy-2-(4-morpholinophenyl)acetic acid as a tan solid (7.25 g, 58%).

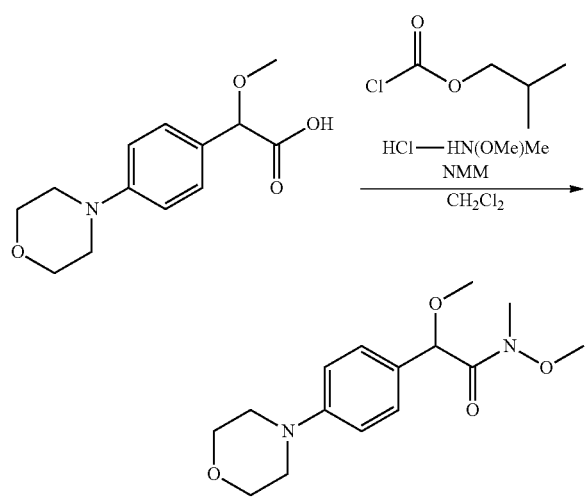

To a suspension of 2-methoxy-2-(4-morpholinophenyl) acetic acid (2.97 g, 11.8 mmol) in anhydr. CH$_2$Cl$_2$ (66 mL) in an oven-dried flask under argon was added N-methylmorpholine (3 mL, 27.3 mmol) and the resulting solution was cooled over ice. Isobutylchloroformate (1.8 mL, 13.76 mmol) was added dropwise. After stirring for 50 min, N,O-dimethylhydroxylamine hydrochloride (1.5 g, 15.3 mmol) was added and the mixture was allowed to warm slowly to room temp. After stirring for 16 hours, saturated aqueous NaHCO$_3$ was added and the mixture stirred for >15 min. The mixture was diluted with CH$_2$Cl$_2$ and the layers were separated. The organics were washed with brine, dried over MgSO$_4$/Na$_2$SO$_4$ and concentrated. Purification by chromatography (60-85% EtOAc-hexanes) gave N,2-dimethoxy-N-methyl-2-(4-morpholinophenyl) acetamide as an off-white solid (3.15 g, 90% yield).

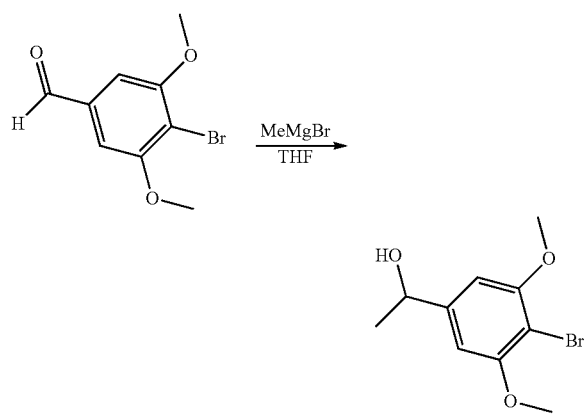

An oven-dried flask under argon was charged with 4-bromo-3,5-dimethoxybenzaldehyde (10.08 g, 41.1 mmol) and anhydrous THF (70 mL). The mixture was cooled over a −78° C. bath then a solution of MeMgBr (3.0 M in diethyl ether, 17.8 mL, 53.4 mmol) was added dropwise from an addition funnel over a period of 45 min. After stirring for 20 min, the mixture was allowed to warm to room temperature and stirred for 19 hours. After quenching with a solution of aqueous NH$_4$Cl, it was diluted with H$_2$O and EtOAc then cooled over an ice bath. After the mixture was cooled, the layers were separated. The organics were washed with H$_2$O and brine then dried over Na$_2$SO$_4$ and concentrated in vacuo. The residue was dissolved in dichloromethane and concentrated in vacuo again to give 1-(4-bromo-3,5-dimethoxyphenyl)ethanol as a white solid (10.8 g, quantitiative yield). The product was used without further purification.

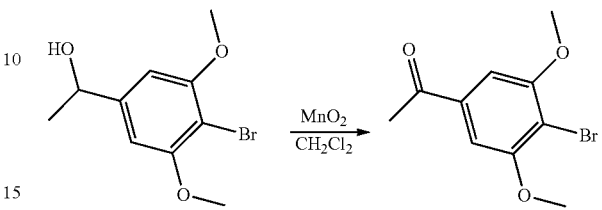

To a solution of 1-(4-bromo-3,5-dimethoxyphenyl)ethanol (10.8 g, 41.1 mmol) in anhydrous CH$_2$Cl$_2$ (150 mL) was added MnO$_2$ (48 g, 552 mmol). After the mixture was placed under a drying tube and stirred at room temperature for 22 hours, it was filtered through a pad of Celite and silica gel and rinsed with EtOAc. Concentration of the filtrate in vacuo gave 1-(4-bromo-3,5-dimethoxyphenyl)ethanone as a white solid (10.3 g, 97% yield). The product was used without further purification.

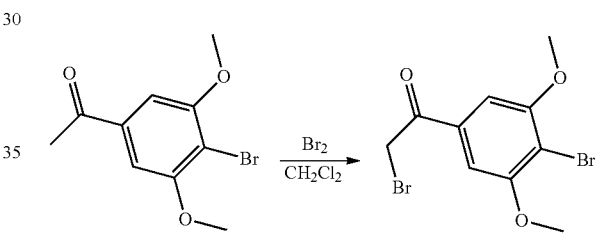

To a solution of 1-(4-bromo-3,5-dimethoxyphenyl)ethanone (0.895 g, 3.45 mmol) in anhydrous CH$_2$Cl$_2$ (5 mL) under a drying tube was added a freshly made solution of Br$_2$ in CH$_2$Cl$_2$ (1.95 M, 1.9 mL, 3.7 mmol) dropwise. The reaction was stirred at room temperature for 30 min then neutralized with a solution of saturated aqueous NaHCO$_3$. The mixture was diluted with CH$_2$Cl$_2$ and the layers were separated. The organics were washed with saturated aqueous NaHCO$_3$ and brine then dried over MgSO$_4$/Na$_2$SO$_4$ and concentrated in vacuo. The crude product was adsorbed onto silica gel (2.9 g) as a CH$_2$Cl$_2$ solution. Purification by chromatography (0-20% EtOAc-hexanes) gave 2-bromo-1-(4-bromo-3,5-dimethoxyphenyl)ethanone as a white solid (0.737 g, 63% yield). Large-scale synthesis of 2-bromo-1-(4-bromo-3,5-dimethoxyphenyl)ethanone was performed without chromatographic purification of the bromide.

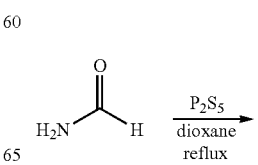

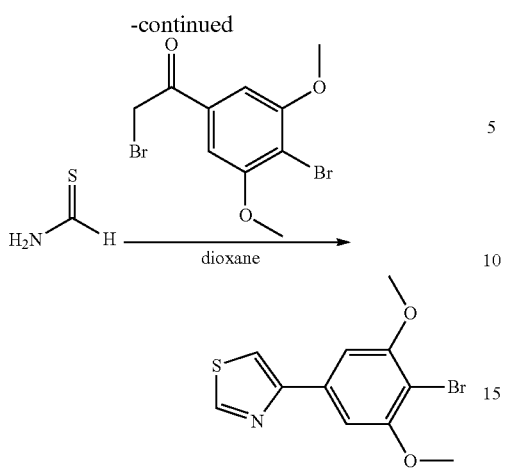

An oven-dried flask under argon was charged with P₂S₅ (0.53 g, 1.2 mmol), anhydrous dioxane (5 mL), and formamide (0.53 mL, 13.3 mmol). The reaction flask was fitted with a reflux condenser and a drying tube and refluxed for 2.25 hours. A separate oven-dried flask under argon was charged with 2-bromo-1-(4-bromo-3,5-dimethoxyphenyl)ethanone (0.313 g, 0.93 mmol) and anhydrous dioxane (6 mL). The thioformamide mixture (above) was decanted into the reaction flask leaving solids behind. The reaction flask was fitted with a reflux condenser, put under a drying tube and refluxed for 3 hours then cooled to room temp. After stirring overnight, the mixture was made basic with the addition of an aqueous solution of 2 M Na₂CO₃, diluted with H₂O then extracted with EtOAc three times. The combined organics were washed with brine, dried over Na₂SO₄ and concentrated. The crude solid was dissolved in CH₂Cl₂ and adsorbed onto silica gel. Purification by chromatography (0-35% EtOAc-hexanes) gave 4-(4-bromo-3,5-dimethoxyphenyl)thiazole as a white solid (0.20 g, 73% yield).

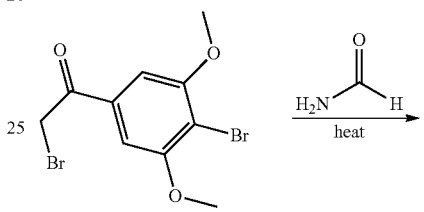

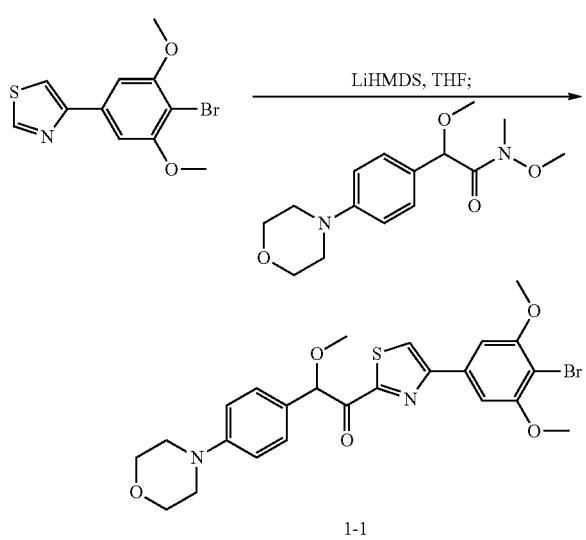

1-1

To a −78° C. solution of 4-(4-bromo-3,5-dimethoxyphenyl)thiazole (0.096 g, 0.32 mmol) in anhydrous THF (2 mL) under argon was added a solution of LiHMDS (1.0 M in THF, 0.35 mmol) dropwise. After stirring for 30 min, a solution of N, 2-dimethoxy-N-methyl-2-(4-morpholinophenyl)aceta-mide (0.121 g, 0.41 mmol) in anhydrous THF (1.5 mL, 1.0 mL) was added dropwise. After stirring for 35 min, the cold bath was removed and the reaction was allowed to warm to room temp. The mixture was quenched with brine and diluted with EtOAc. The layers were separated and the organic layer was washed with brine, dried over Na₂SO₄ and concentrated. Purification by chromatography (25-45% EtOAc-hexanes) gave 1-(4-(4-bromo-3,5-dimethoxyphenyl)thiazol-2-yl)-2-methoxy-2-(4-morpholinophenyl)ethanone as a yellow solid (0.050 g, 29% yield). MS: m/z 533.1 [M+H]⁺.

Example 2

1-(4-(4-Bromo-3,5-Dimethoxyphenyl)Oxazol-2-yl)-2-Methoxy-2-(4-Morpholinophenyl)-Ethanone

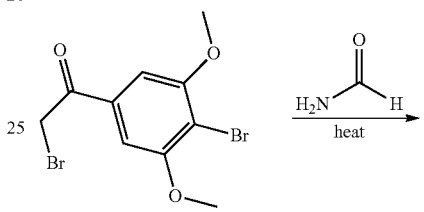

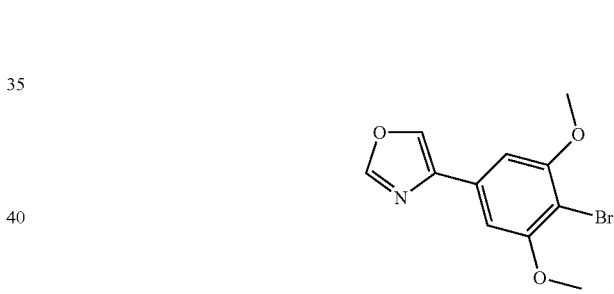

A solution of 2-bromo-1-(4-bromo-3,5-dimethoxyphenyl)ethanone (0.8 g, 0.96 mmol) in formamide (7 mL) in an oven-dried flask under argon was heated at 100° C. for 10 hours then 110° C. for 5 hours. After cooling to room temp, EtOAc and saturated aqueous NaHCO₃ were carefully added and the mixture was stirred for 15 minutes. It was then extracted with EtOAc twice and the combined organics were washed with H₂O and brine, dried over Na₂SO₄ and concentrated. Purification by chromatography (20-40% EtOAc-hexanes) provided 4-(4-bromo-3,5-dimethoxyphenyl)oxazole as a yellow solid (0.387 g, 58% yield).

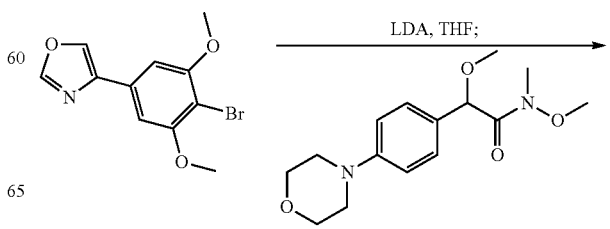

-continued

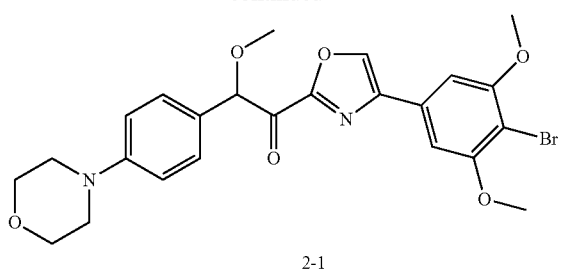

2-1

To a −20° C. solution of 4-(4-bromo-3,5-dimethoxyphenyl)oxazole (0.158 g, 0.56 mmol) in anhydrous THF (2 mL) in an oven-dried flask under argon was added a solution of LDA (2.0 M in THF/heptane/ethylbenzene; 0.37 mL, 0.74 mmol) dropwise. The mixture was stirred at −20 to −10° C. for 50 min then cooled to −20° C. A solution of N,2-dimethoxy-N-methyl-2-(4-morpholinophenyl)acetamide (0.245 g, 0.83 mmol) in anhydrous THF (3 mL) was added then the mixture was allowed to slowly warm to room temperature and stirred for a total of 21 hours. The reaction mixture was quenched with H$_2$O and extracted with EtOAc. The combined organics were washed with brine, dried over Na$_2$SO$_4$ and concentrated. Purification by chromatography (50-60% EtOAc-hexanes) provided 1-(4-(4-bromo-3,5-dimethoxyphenyl)oxazol-2-yl)-2-methoxy-2-(4-morpholinophenyl)-ethanone as a yellow solid (0.097 g, 34% yield). MS: m/z 517.1 [M+H]$^+$.

Example 3

2-(4-(1H-Pyrazol-1-yl)Phenyl)-1-(4-(4-Bromo-3,5-Dimethoxyphenyl)Thiazol-2-yl)-2-Methoxyethanone

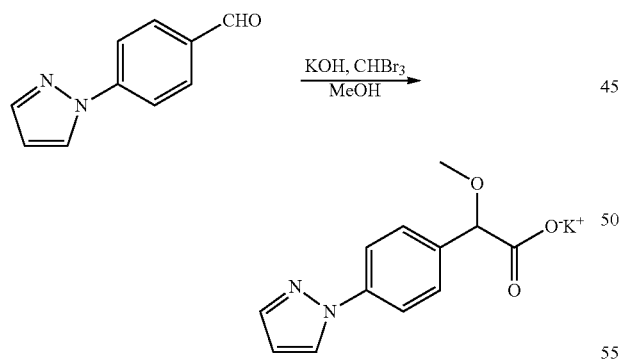

To a stirred solution of 4-(1H-pyrazol-1-yl)benzaldehyde (1.3 g, 7.55 mmol) and bromoform (0.85 mL, 9.75 mmol) in MeOH (10 mL) and dioxane (10 mL) was added dropwise a solution of potassium hydroxide (2.2 g, 39 mmol) in MeOH (10 mL) over 15 minutes. Stirring was then continued for 23 hours. The mixture was filtered through Celite, rinsed through with EtOAc and concentrated under reduced pressure to yield potassium 2-(4-(1H-pyrazol-1-yl)phenyl)-2-methoxyacetate as a light yellow solid (3.2 g) that was used without further purification. See U.S. Pat. No. 7,129,238.

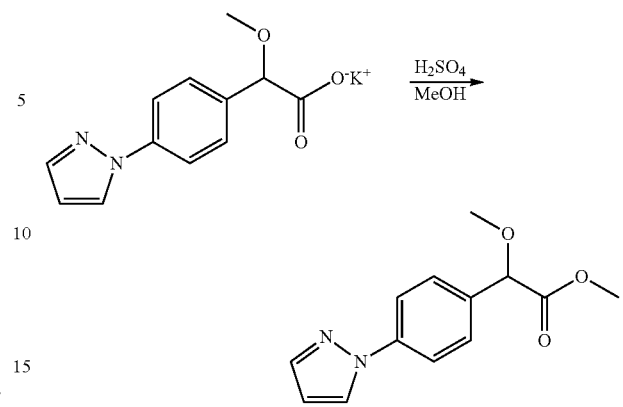

To a stirred solution of potassium 2-(4-(1H-pyrazol-1-yl)phenyl)-2-methoxyacetate (~7.55 mmol) in dry MeOH under argon was added sulfuric acid (2.0 mL) dropwise. The mixture was heated at 80° C. for 17 hours. After cooling to room temperature, water was added then the mixture made basic with saturated aqueous NaHCO$_3$ addition. The aqueous phase was extracted with EtOAc and the combined organics were washed with water and brine then dried over Na$_2$SO$_4$ and concentrated in vacuo. Purification by chromatography (20-35% EtOAc-hexanes) provided methyl 2-(4-(1H-pyrazol-1-yl)phenyl)-2-methoxyacetate as a colorless oil (0.88 g, 47% yield for two steps).

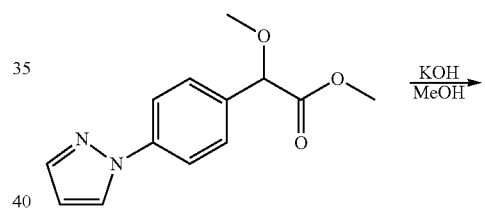

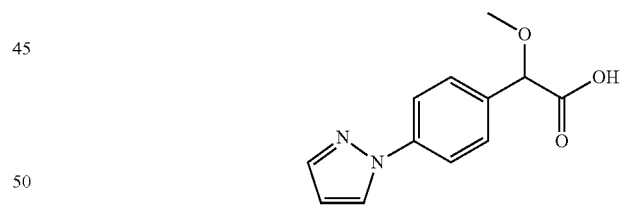

To a stirred solution of methyl 2-(4-(1H-pyrazol-1-yl)phenyl)-2-methoxyacetate (0.204 g, 0.83 mmol) in dry MeOH (5 mL) under argon was added a solution of KOH in MeOH (1.6 mL of a 0.5 M solution, 8.3 mmol) and the reaction was heated to reflux for 5 hours. The reaction mixture was cooled to room temperature and the volatiles were removed under reduced pressure. The residue was diluted with saturated aqueous NH$_4$Cl and extracted with EtOAc. Additional EtOAc was then used to extract the aqueous phase as the pH was adjusted from ~8 to ~2 using concentrated HCl. The combined organics were dried over Na$_2$SO$_4$, filtered, and the solvents removed under reduced pressure to yield 2-(4-(1H-pyrazol-1-yl)phenyl)-2-methoxyacetic acid (0.18 g, 95%) which was used without further purification.

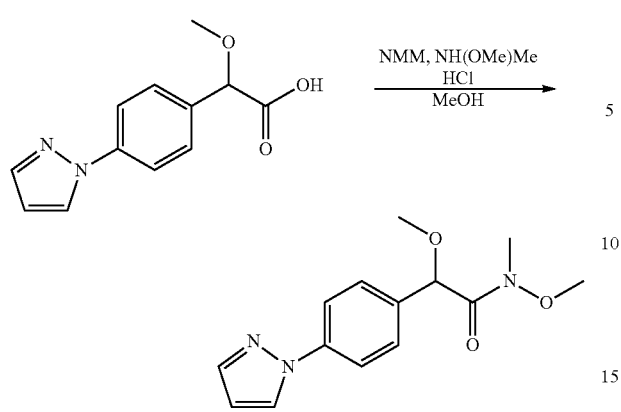

To a solution of methyl 2-(4-(1H-pyrazol-1-yl)phenyl)-2-methoxyacetic acid (0.18 g, 0.77 mmol) in dry dichloromethane (5 mL) under argon was added N-methylmorpholine (0.18 mL, 1.7 mmol). The reaction mixture was cooled to 0° C., isobutylchloroformate was added, (0.11 mL, 0.85 mmol) and the mixture was stirred for 40 minutes. N,O-dimethylhydroxylamine hydrochloride (0.098 g, 1 mmol) was then added in one portion and slowly allowed to warm to room temperature and stirred for 18 hours. The mixture was diluted with saturated aqueous NaHCO$_3$ and extracted with EtOAc. The combined organics were washed with brine, dried over Na$_2$SO$_4$ and concentrated in vacuo. Purification by chromatography (0-80% EtOAc-hexanes) provided 2-(4-(1H-pyrazol-1-yl)phenyl)-N,2-dimethoxy-N-methylacetamide (0.16 g, 76% yield).

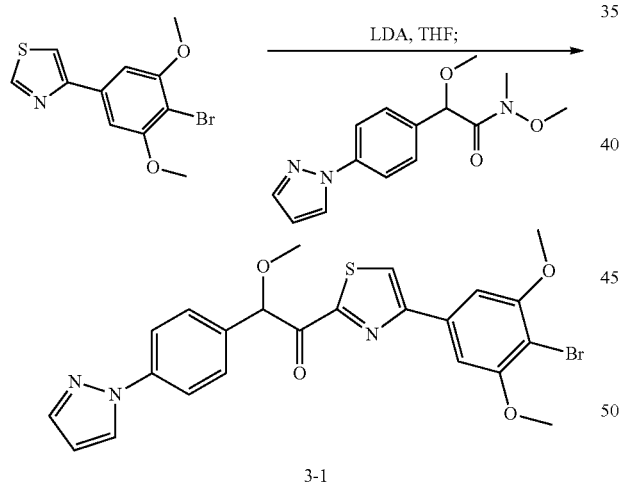

3-1

To a −20° C. solution of 4-(4-bromo-3,5-dimethoxyphenyl)thiazole (0.092 g, 0.305 mmol) in anhydrous THF (2 mL) under argon was added a solution of LDA (0.18 mL of a 2.0 M solution in THF/heptane/ethylbenzene, 0.37 mmol) dropwise. After stirring for 30 min, the reaction was cooled to −78° C. and a solution of 2-(4-(1H-pyrazol-1-yl)phenyl)-N,2-dimethoxy-N-methylacetamide (0.15 g, 0.55 mmol) in anhydrous THF (1.5 mL, 1.0 mL) was added dropwise. After stirring for 90 min, the mixture was quenched with brine and diluted with EtOAc. The layers were separated and the organic layer was washed with brine, dried over Na$_2$SO$_4$ and concentrated. Purification by chromatography (0-35% EtOAc-hexanes) gave 2-(4-(1H-pyrazol-1-yl)phenyl)-1-(4-(4-bromo-3,5-dimethoxyphenyl)thiazol-2-yl)-2-methoxyethanone as a yellow solid (0.030 g, 20% yield). MS: m/z 514.0 [M+H]$^+$.

Example 4

1-(4-(4-Bromo-3,5-Dimethoxyphenyl)-1-Methyl-1H-Imidazol-2-yl)-2-Methoxy-2-(4-Morpholinophenyl) Ethanone

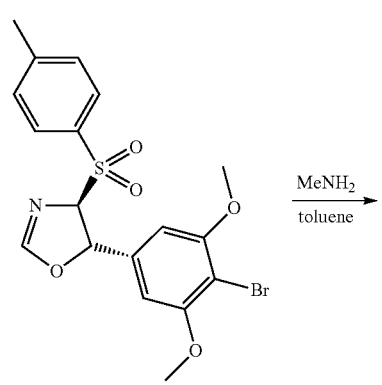

To an oven-dried flask under argon was added 4-bromo-3,5-dimethoxybenzaldehyde (1.0 g, 4.08 mmol), absolute EtOH (34 mL), p-toluenesulfonylmethyl isocyanide (0.78 g, 4.0 mmol) and KCN (0.035 g, 0.54 mmol). The mixture was stirred for 19 hours at room temperature then concentrated in vacuo to give 5-(4-bromo-3,5-dimethoxyphenyl)-4-tosyl-4,5-dihydrooxazole which was used in the next synthetic step without purification.

-continued

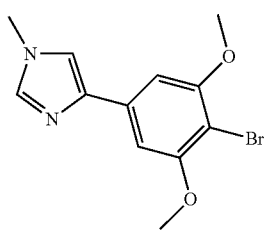

5

10

To an oven-dried pressure tube was added 5-(4-bromo-3,5-dimethoxyphenyl)-4-tosyl-4,5-dihydrooxazole (0.4 g, 0.91 mmol), methylamine-THF solution (1.8 mL of a 2.0 M solution, 3.6 mmol), and xylenes (5 mL). The tube was sealed under argon then heated at 135° C. for 15 hours. After cooling to room temperature, the reaction mixture was transferred and concentrated in vacuo then partitioned between EtOAc and H₂O. The layers were separated and the aqueous layer was extracted with EtOAc. The combined organics were washed with brine twice, dried over Na₂SO₄ and concentrated. Purification by chromatography (50-100% EtOAc-hexanes then 2-5% MeOH-EtOAc) provided 4-(4-bromo-3,5-dimethoxyphenyl)-1-methyl-1H-imidazole as a light yellow solid (0.056 g, 21% yield).

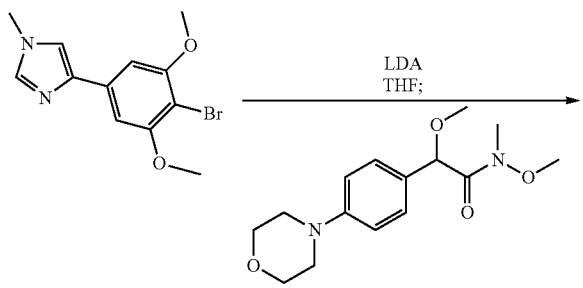

2-methoxy-2-(4-morpholinophenyl) ethanone (0.0039 g, 4% yield). MS: m/z 530.1 [M+H]⁺.

Example 5

2-(4-(1H-Pyrazol-1-yl)Phenyl)-1-(4-(4-Bromo-3,5-Dimethoxyphenyl)Oxazol-2-yl)-2-Methoxyethanone

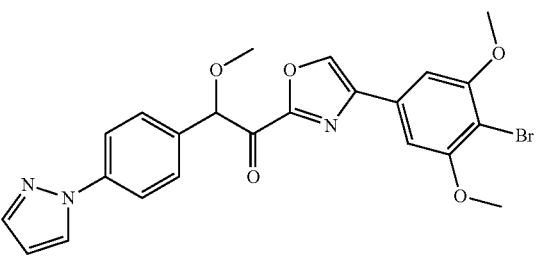

5-1

2-(4-(1H-pyrazol-1-yl)phenyl)-1-(4-(4-bromo-3,5-dimethoxyphenyl) oxazol-2-yl)-2-methoxyethanone was synthesized from 2-(4-(1H-pyrazol-1-yl)phenyl)-N,2-dimethoxy-N-methylacetamide and 4-(4-bromo-3,5-dimethoxyphenyl)oxazole by a method similar to that used for Example 2 except that the amide was added to the reaction mixture at −50° C. MS: m/z 498.1 [M+H]⁺.

Example 6

1-(4-(4-Bromo-3,5-Dimethoxyphenyl)Oxazol-2-yl)-2-Methoxy-2-(4-(Piperidin-1-yl)Phenyl)Ethanone

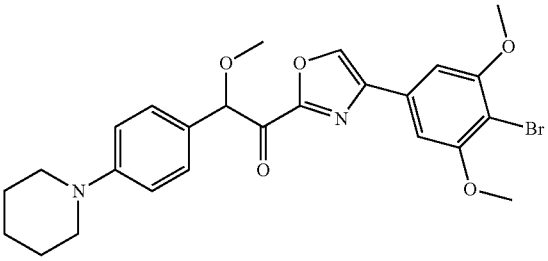

6-1

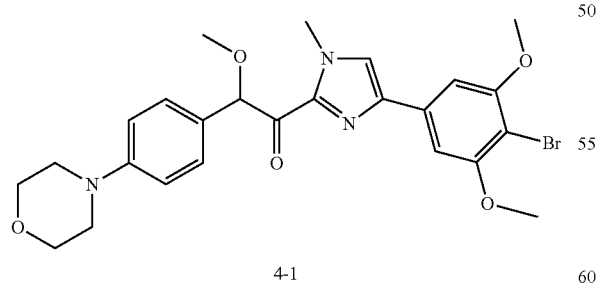

4-1

The method used for the final coupling step of Example 3 was used with modification. The reaction was allowed to warm to room temperature overnight. Purification by chromatography (40-55% EtOAc-hexanes) provided 1-(4-(4-bromo-3,5-dimethoxyphenyl)-1-methyl-1H-imidazol-2-yl)-

N,2-dimethoxy-N-methyl-2-(4-(piperidin-1-yl)phenyl) acetamide was synthesized in two steps from 4-(piperidin-1-yl)benzaldehyde following the method used for Example 1. 1-(4-(4-Bromo-3,5-dimethoxyphenyl)oxazol-2-yl)-2-methoxy-2-(4-(piperidin-1-yl)phenyl)ethanone was synthesized from N,2-dimethoxy-N-methyl-2-(4-(piperidin-1-yl)phenyl)

acetamide and 4-(4-bromo-3,5-dimethoxyphenyl)oxazole following the method used for Example 5. MS: m/z 515.1 [M+H]⁺.

Example 7

1-(4-(4-Bromo-3,5-Dimethoxyphenyl)Oxazol-2-yl)-2-Methoxy-2-(4-(Pyrrolidin-1-yl)Phenyl)Ethanone 7-1

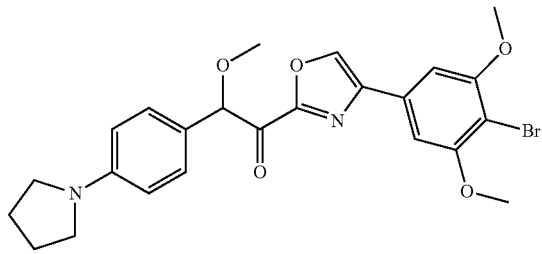

N,2-dimethoxy-N-methyl-2-(4-(pyrrolidin-1-yl)phenyl) acetamide was synthesized from 4-(pyrrolidin-1-yl)benzaldehyde following the method used for the synthesis of Example 1. 1-(4-(4-Bromo-3,5-dimethoxyphenyl)oxazol-2-yl)-2-methoxy-2-(4-(pyrrolidin-1-yl)phenyl)ethanone was synthesized from N,2-dimethoxy-N-methyl-2-(4-(pyrrolidin-1-yl)phenyl)acetamide and 4-(4-bromo-3,5-dimethoxyphenyl)oxazole following the method used for Example 2 except that the amide was added to the reaction mixture at −45° C. MS: m/z 501.1 [M+H]⁺.

Example 8

1-(4-(4-Bromo-3,5-Dimethoxyphenyl)Oxazol-2-yl)-2-(4-Isopropoxyphenyl)-2-Methoxyethanone

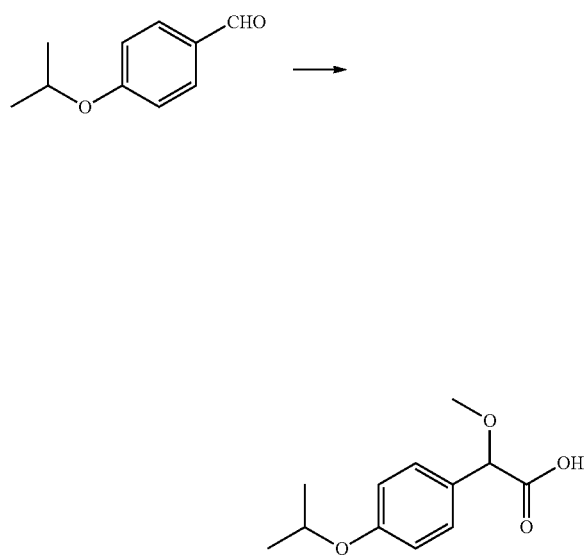

An oven-dried flask was charged with 4-isopropoxybenzaldehyde (4.9 g, 29.9 mmol), anhydrous methanol (30 mL) and anhydrous dioxane (30 mL) then fitted with an addition funnel. The addition funnel was charged with a solution of KOH (8.4 g, 149.5 mmol) in anhydrous methanol (30 mL) and an aliquot (~2 mL) was added to the reaction mixture. Bromoform (3.4 mL, 38.8 mmol) was added to the reaction mixture then the remaining KOH/MeOH solution was added dropwise over 10 minutes. After stirring for 18 hours, the mixture was concentrated in vacuo. The residue was diluted with water and the pH was adjusted to ~2 using concentrated HCl then extracted with EtOAc. The combined organics were dried over Na₂SO₄ and filtered. Concentration of the filtrate in vacuo gave 2-(4-isopropoxyphenyl)-2-methoxyacetic acid as a light yellow solid (6.8 g) which was used without further purification.

8-1

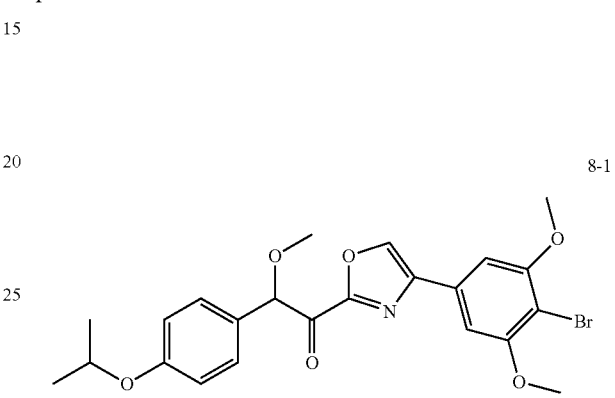

2-(4-Isopropoxyphenyl)-N,2-dimethoxy-N-methylacetamide was synthesized from 2-(4-isopropoxyphenyl)-2-methoxyacetic acid following the method used for the synthesis of Example 1. 1-(4-(4-Bromo-3,5-dimethoxyphenyl)oxazol-2-yl)-2-(4-isopropoxyphenyl)-2-methoxyethanone was synthesized from 2-(4-isopropoxyphenyl)-N,2-dimethoxy-N-methylacetamide and 4-(4-bromo-3,5-dimethoxyphenyl)oxazole following the method used for the synthesis of Example 7. MS: m/z 490.1 [M+H]⁺.

Example 9

1-(4-(4-Bromo-3,5-Dimethoxyphenyl)Oxazol-2-yl)-2-Methoxy-2-(Quinolin-5-yl)Ethanone 9-1

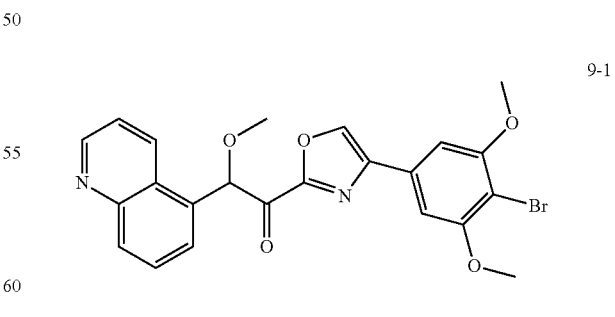

N,2-dimethoxy-N-methyl-2-(quinolin-5-yl)acetamide was synthesized from quinoline-5-carbaldehyde in two steps following the method used for the synthesis of Example 1. 1-(4-(4-Bromo-3,5-dimethoxyphenyl)oxazol-2-yl)-2-methoxy-2-(quinolin-5-yl)ethanone was synthesized from N,2-dimethoxy-N-methyl-2-(quinolin-5-yl)acetamide and 4-(4- bromo-3,5-dimethoxyphenyl)oxazole following the method used for Example 2. MS: m/z 483.0 [M+H]+.

Example 10

1-(4-(4-Bromo-3,5-Dimethoxyphenyl)Oxazol-2-yl)-2-Methoxy-2-(Quinolin-3-yl)Ethanone

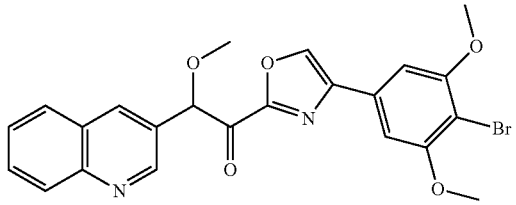

10-1

N,2-dimethoxy-N-methyl-2-(quinolin-3-yl)acetamide was synthesized from quinoline-3-carbaldehyde in two steps following the method used for the synthesis of Example 1. 1-(4-(4-Bromo-3,5-dimethoxyphenyl)oxazol-2-yl)-2-methoxy-2-(quinolin-3-yl)ethanone was synthesized from N,2-dimethoxy-N-methyl-2-(quinolin-3-yl)acetamide and 4-(4-bromo-3,5-dimethoxyphenyl)oxazole following the method used for Example 2. MS: m/z 483.1 [M+H]+.

Example 11

1-(4-(4-Bromo-3,5-Dimethoxyphenyl)Oxazol-2-yl)-2-Methoxy-2-(4-(5-Methyl-1,3,4-Oxadiazol-2-yl)Phenyl)Ethanone

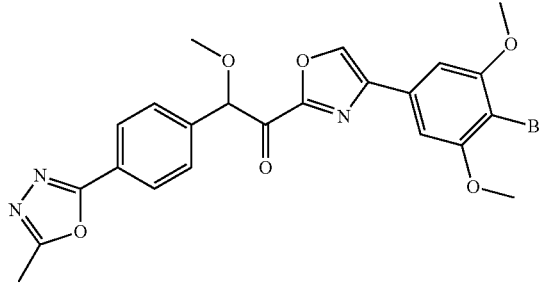

11-1

N,2-dimethoxy-N-methyl-2-(4-(5-methyl-1,3,4-oxadiazol-2-yl)phenyl)acetamide was synthesized from 4-(5-methyl-1,3,4-oxadiazol-2-yl)benzaldehyde in two steps following the method used for the synthesis of Example 1. 1-(4-(4-Bromo-3,5-dimethoxyphenyl)oxazol-2-yl)-2-methoxy-2-(4-(5-methyl-1,3,4-oxadiazol-2-yl)phenyl)ethanone was synthesized from N,2-dimethoxy-N-methyl-2-(4-(5-methyl-1,3,4-oxadiazol-2-yl)phenyl)acetamide and 4-(4-bromo-3,5-dimethoxyphenyl)oxazole following the method used for Example 2 except that the amide was added to the reaction mixture at −30° C. MS: m/z 514.0 [M+H]+.

Example 12

1-(5-(4-Bromo-3,5-Dimethoxyphenyl)Furan-2-yl)-2-Methoxy-2-(4-Morpholinophenyl)Ethanone

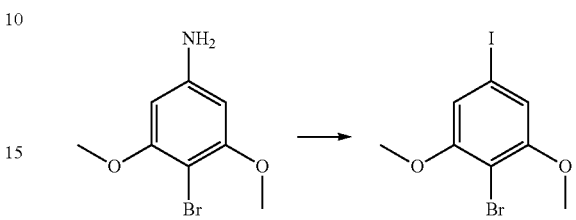

To a flask containing a suspension of 4-bromo-3,5-dimethoxyaniline (1.99 g, 8.56 mmol; synthesized according to US2006/128695) in H₂O (60 mL) was slowly added concentrated $H_2SO_4$ (10 mL). The exotherm was controlled by cooling over ice then the reaction was cooled to −10 to −8° C. (bath temperature). After a solution of $NaNO_2$ (0.70 g, 10 mmol) in $H_2O$ (3.5 mL) was added dropwise over a period of 6 min, the mixture was stirred for 70 min. A solution of KI (2.8 g, 16.9 mmol) in $H_2O$ (3.5 mL) was added dropwise and the mixture was stirred at −10 to −5° C. for 30 min. After the cold bath was removed, the mixture was stirred for 80 min then EtOAc was added and the mixture stirred for an additional 40 min. The layers were separated and the aqueous layer was extracted with EtOAc several times. The combined organics were washed with 1 M NaOH twice, 10% $Na_2S_2O_3$ twice and brine then dried over $Na_2SO_4$. Purification by chromatography (0-20% EtOAc-hexanes) provided 2-bromo-5-iodo-1,3-dimethoxybenzene (1.86 g, 63% yield).

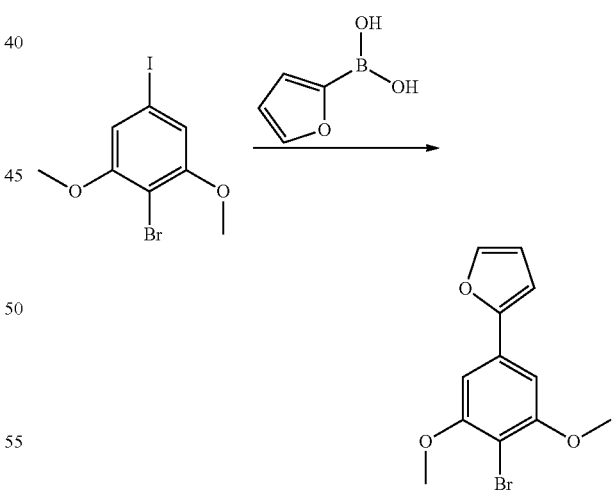

2-(4-Bromo-3,5-dimethoxyphenyl)furan was synthesized according to the procedure reported in WO 2008/040669 as follows. To a round bottom flask containing 3,5-dimethoxy-4-bromo-iodobenzene (7.9 g, 85% purity, 19.6 mmol), 2-furylboronic acid (3.4 g, 30.4 mmol), triphenylphosphine (0.358 g, 1.37 mmol), tetrabutylammonium bromide (7.94 g, 14.6 mmol) and $Na_2CO_3$ (4.9 g, 46.2 mmol) was added THF (87 mL) and $H_2O$ (87 mL). The mixture was degassed by alternately putting under house vacuum and argon three times for several minutes each. 10% Pd/C (1.36 g) was added and the mixture was heated at 60° C. for 17 hrs under argon. After cooling to room temperature, the mixture was filtered through Celite and rinsed with THF and EtOAc. The filtrate layers were separated and the organic layer was washed with brine, dried over Na$_2$SO$_4$ and concentrated. Purification by column chromatography (0-25% Et$_2$O-hexanes) gave 2-(4-bromo-3,5-dimethoxyphenyl)furan as a white solid (5.06 g, 91% yield). Product TLC Rf 0.35 (15% EtOAc-hexanes TLC eluent).

was collected from MeOH-Et$_2$O (~10%) to give additional product (0.220 g total, 59% yield). MS: m/z 516.1 [M+H]$^+$.

Example 13

1-(5-(4-Bromo-3,5-Dimethoxyphenyl)Furan-2-yl)-2-Methoxy-2-(4-(5-Methyl-1,3,4-Oxadiazol-2-yl)Phenyl)Ethanone

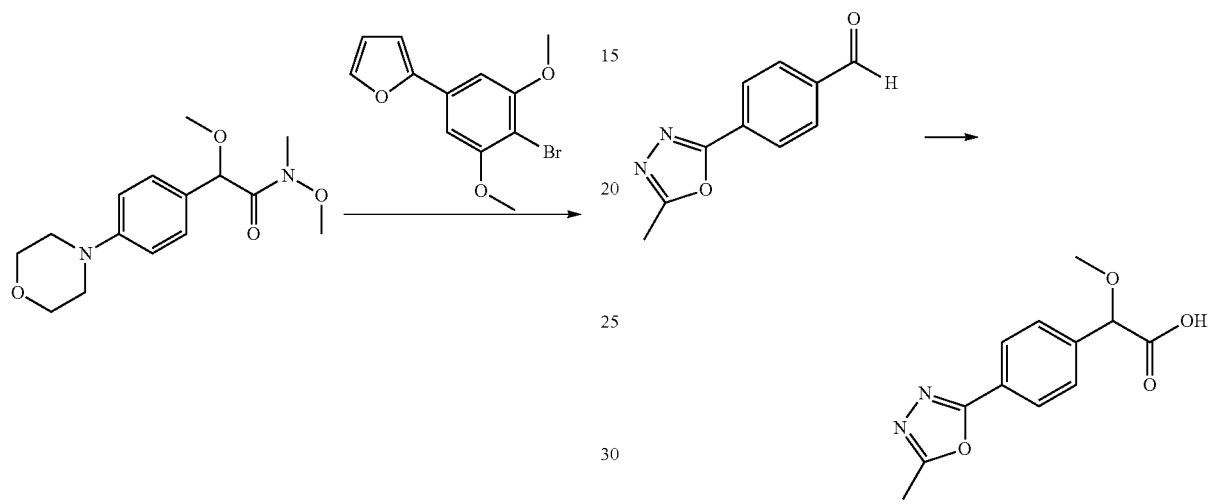

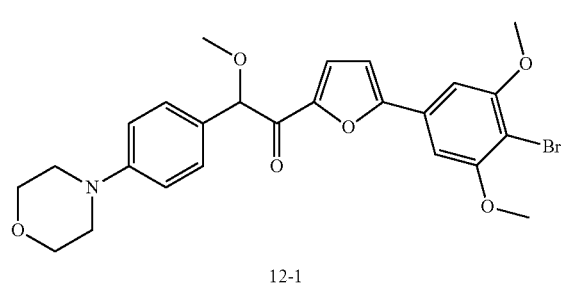

12-1

To a solution of 2-(4-bromo-3,5-dimethoxyphenyl)furan (0.203 g, 0.72 mmol) in anhydrous THF (2 mL) under argon in an oven-dried flask cooled to −78° C. was added a solution of lithium diisopropylamide (2.0 M in THF/heptane/ethylbenzene; 0.4 mL, 0.8 mmol) dropwise. After stirring for 35 min at −78° C., a solution of N,2-dimethoxy-N-methyl-2-(4-morpholinophenyl)acetamide (0.315 g, 1.1 mmol) in THF (2 mL) was added dropwise. After stirring for 25 min, the mixture was allowed to warm to room temp while stirring for 2 hrs. The reaction was quenched with the addition of saturated aqueous NH$_4$Cl then brine and EtOAc were added. The layers were separated and the organic layer was washed with brine, dried over Na$_2$SO$_4$ and concentrated in vacuo. Purification by column chromatography (35-65% EtOAc-hexanes) provided an oil that was triturated with MeOH-Et$_2$O (1:1) with sonication. The solid was collected on a Büchner, rinsed with MeOH-Et$_2$O (1:1) and dried in vacuo to give 1-(5-(4-bromo-3,5-dimethoxyphenyl)furan-2-yl)-2-methoxy-2-(4-morpholinophenyl)ethanone as a yellow solid. A second batch To a solution of 4-(5-methyl-1,3,4-oxadiazol-2-yl)benzaldehyde (5.12 g, 27.2 mmol) in anhydrous MeOH (27 mL) and anhydrous dioxane (27 mL) at −15 to −10° C. (bath temperature) was added several drops of a solution of KOH (7.6 g, 135.4 mmol) in MeOH (27 mL). Bromoform (3 mL, 34.4 mmol) was added, then the remaining KOH/MeOH solution was added over a period of 20 min. The mixture was stirred for 1 hr and the cold bath was removed. After stirring for 30 min, the reaction was put over an ice bath and allowed to warm slowly to room temperature overnight then concentrated to dryness. After dissolving in a minimum amount of H$_2$O, the residue was acidified to pH 1 with 6 M HCl. The aqueous mixture was extracted with EtOAc several times with the addition of brine to the aqueous layer during extraction. The combined organics were washed with brine, dried over Na$_2$SO$_4$ and concentrated in vacuo to give 2-methoxy-2-(4-(5-methyl-1,3,4-oxadiazol-2-yl)phenyl)acetic acid as a semisolid (6.8 g, quantitative yield). The product was used without further purification.

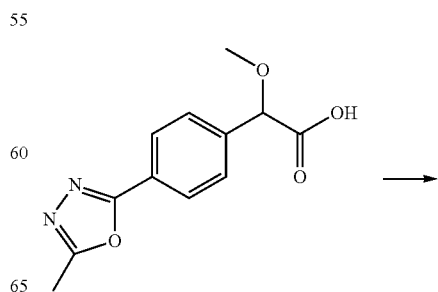

-continued

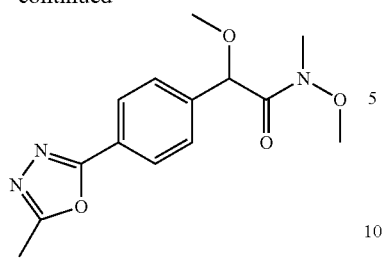

To an ice-cold solution of 2-methoxy-2-(4-(5-methyl-1,3,4-oxadiazol-2-yl)phenyl)acetic acid (6.8 g, 27.4 mmol) in anhydrous CH₂Cl₂ (270 mL) and diisopropylethylamine (17 mL, 97 mmol) under argon was added bis(2-methoxyethyl)aminosulfur trifluoride (5.6 mL, 30.3 mmol) dropwise. After stirring over an ice bath for 45 min, N,O-dimethylhydroxylamine hydrochloride (3.40 g, 34.8 mmol) was added in three aliquots over a period of 15 min. The mixture was stirred for 15 min then the ice bath was removed. After 3 hrs, saturated aqueous NaHCO₃ was added and stirred for 30 min. The layers were separated and the aqueous layer was extracted with CH₂Cl₂. The combined organics were washed with saturated aqueous NaHCO₃, H₂O and brine, dried over MgSO₄, filtered through Celite and concentrated in vacuo. Purification by chromatography (75-100% EtOAc-hexanes then 0-5% EtOH-EtOAc) gave N,2-dimethoxy-N-methyl-2-(4-(5-methyl-1,3,4-oxadiazol-2-yl)phenyl)acetamide as an oil that solidified upon standing (2.06 g, 26% yield).

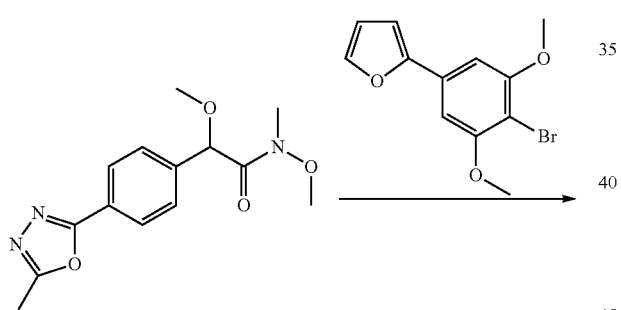

13-1

2-(4-Bromo-3,5-dimethoxyphenyl)furan was coupled with N,2-dimethoxy-N-methyl-2-(4-(5-methyl-1,3,4-oxadiazol-2-yl)phenyl)acetamide according to the method used for the synthesis of Example 12. Purification by chromatography (50-80% EtOAc-hexanes) provided 1-(5-(4-bromo-3,5-dimethoxyphenyl)furan-2-yl)-2-methoxy-2-(4-(5-methyl-1,3,4-oxadiazol-2-yl)phenyl)ethanone as a yellow foam (0.356 g, 40% yield). MS: m/z 513.2 [M+H]⁺.

Example 14

2-(4-(1H-Pyrazol-1-yl)Phenyl)-1-(5-(4-Bromo-3,5-Dimethoxyphenyl)Furan-2-yl)-2-Methoxyethanone

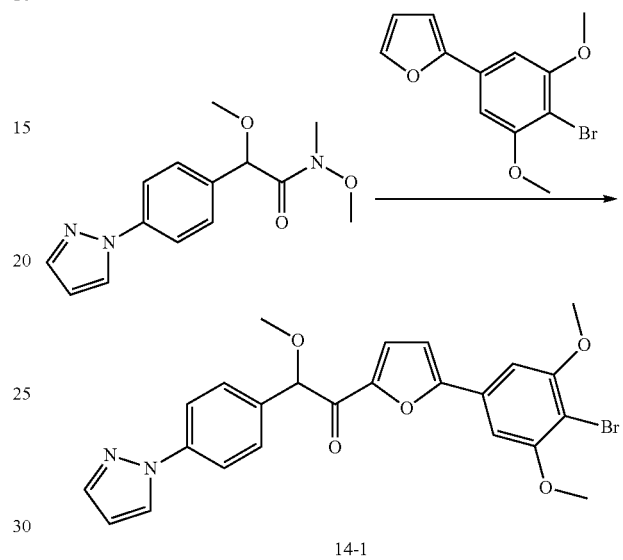

14-1

The method used for the final coupling step of Example 12 was used. Purification by chromatography (20-55% EtOAc-hexanes) provided 2-(4-(1H-pyrazol-1-yl)phenyl)-1-(5-(4-bromo-3,5-dimethoxyphenyl)furan-2-yl)-2-methoxyethanone as a light yellow solid (0.0625 g, 37% yield). MS: m/z 497.2 [M+H]⁺.

Example 15

2-(4-(1H-Pyrazol-4-yl)Phenyl)-1-(5-(4-Bromo-3,5-Dimethoxyphenyl)Furan-2-yl)-2-Methoxyethanone

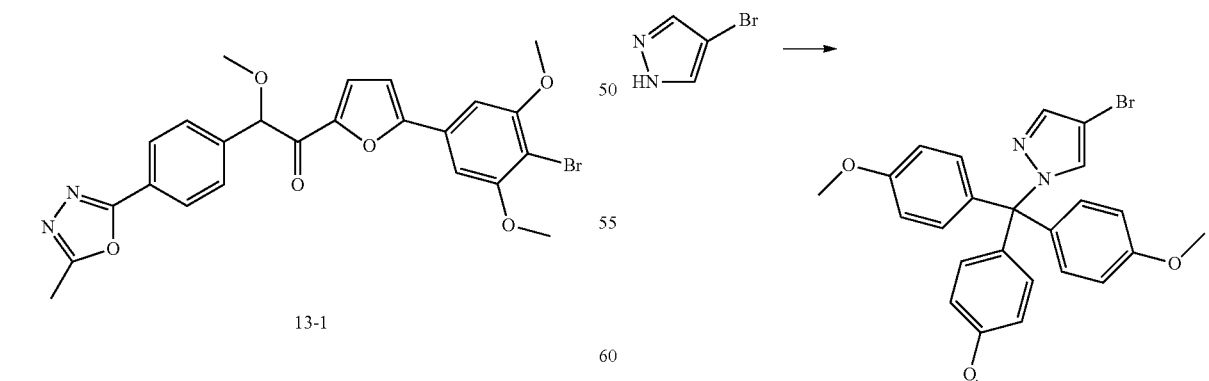

To a suspension of 4-bromopyrazole (1.5 g, 10.2 mmol) and 4,4',4''-trimethoxytrityl chloride (4.5 g, 12.2 mmol) in anhydrous DMF (20 mL) under argon was added triethylamine (3 mL, 21.5 mmol) and the mixture was cooled over an ice bath. After stirring for 10 min, the ice bath was removed and the reaction stirred for 2.5 hrs. The mixture was diluted with H₂O and extracted with EtOAc. The combined organics were washed with H₂O three times then saturated aqueous NaHCO₃ and brine. The solution was dried over Na₂SO₄ and concentrated in vacuo. The crude oil was recrystallized from isopropanol to give 4-bromo-1-(tris(4-methoxyphenyl)methyl)-1H-pyrazole as off-white crystals (two batches; 2.55 g, 52% yield).

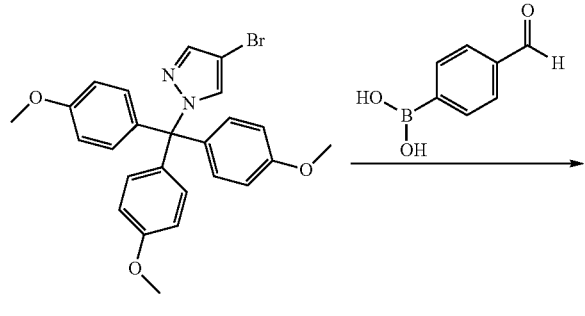

A mixture of 4-bromo-1-(tris(4-methoxyphenyl)methyl)-1H-pyrazole (1.47 g, 3.1 mmol), (4-formylphenyl)boronic acid (0.94 g, 6.3 mmol), and K₂CO₃ (0.65 g, 4.7 mmol) in DME-H₂O (25 mL, 4:1) was degassed by alternately putting under house vacuum and argon three times for several minutes each. Tetrakis(triphenylphosphine)palladium (0.35 g, 0.3 mmol) was added then the mixture was degassed again. After heating for 16.5 hrs at 80° C. and cooling to room temperature, H₂O was added. The mixture was extracted with EtOAc and the combined organics were washed with H₂O, saturated aqueous NaHCO₃ and brine then dried over Na₂SO₄ and concentrated in vacuo. Purification by chromatography (20-30% EtOAc-hexanes; EtOAc containing 1% Et₃N) gave 4-(1-(tris(4-methoxyphenyl)methyl)-1H-pyrazol-4-yl)benzaldehyde (1.31 g combined from two reactions, 33%).

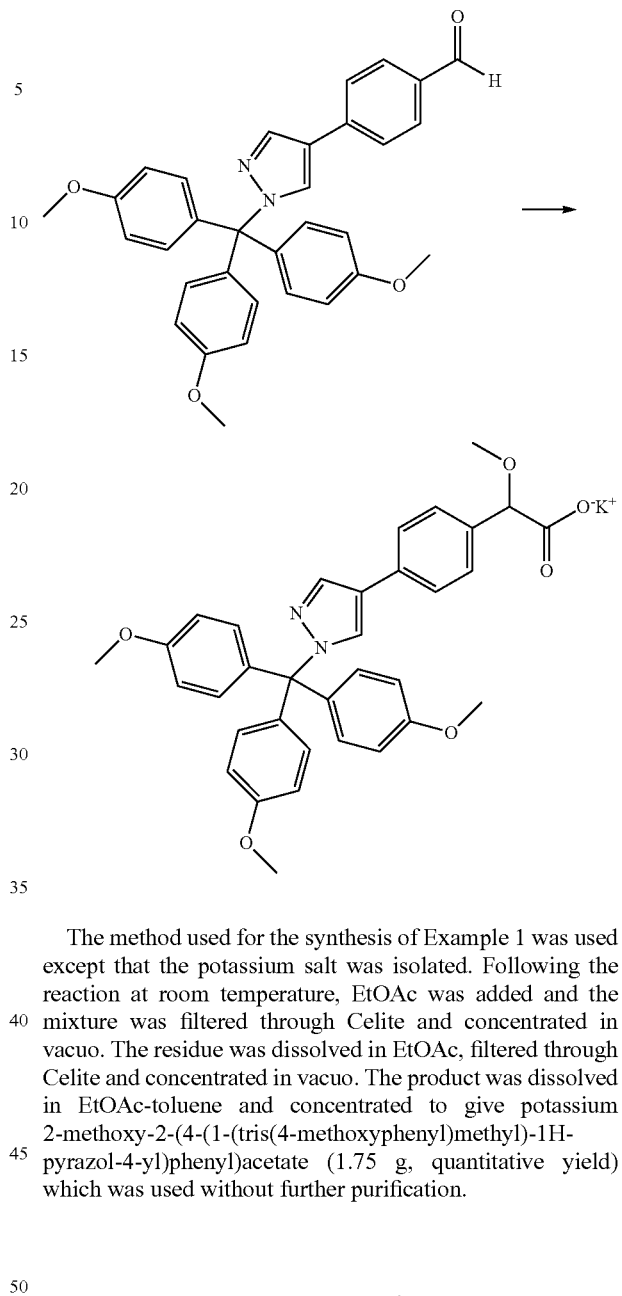

The method used for the synthesis of Example 1 was used except that the potassium salt was isolated. Following the reaction at room temperature, EtOAc was added and the mixture was filtered through Celite and concentrated in vacuo. The residue was dissolved in EtOAc, filtered through Celite and concentrated in vacuo. The product was dissolved in EtOAc-toluene and concentrated to give potassium 2-methoxy-2-(4-(1-(tris(4-methoxyphenyl)methyl)-1H-pyrazol-4-yl)phenyl)acetate (1.75 g, quantitative yield) which was used without further purification.

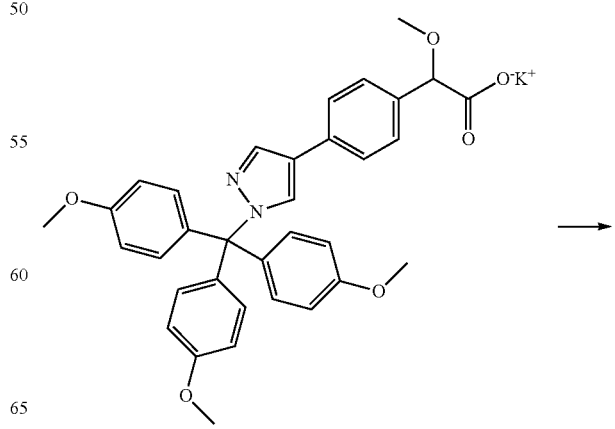

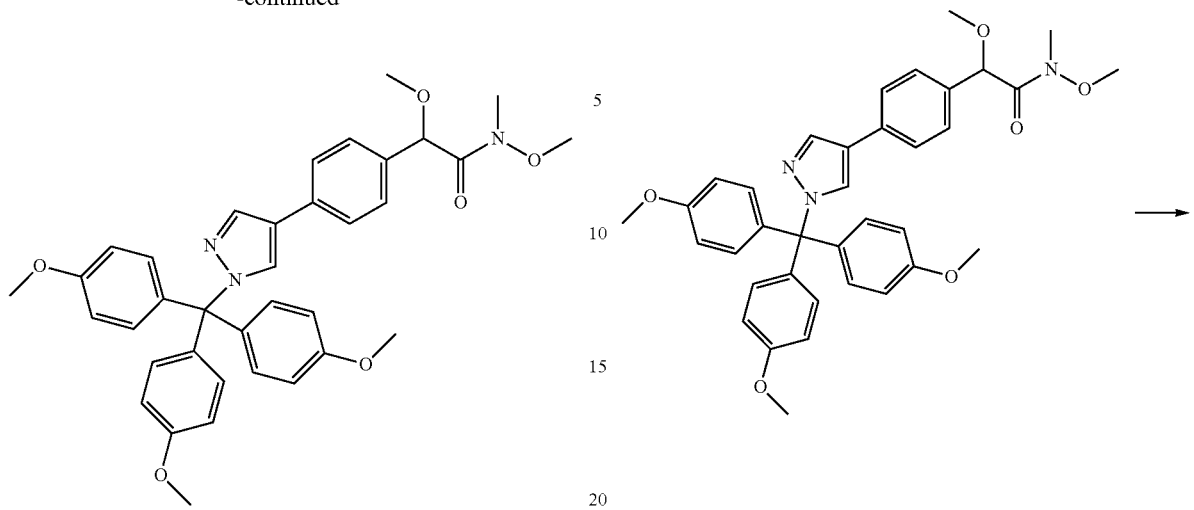

To an ice-cold solution of potassium 2-methoxy-2-(4-(1-(tris(4-methoxyphenyl)methyl)-1H-pyrazol-4-yl)phenyl)acetate (1.25 g, 2.1 mmol) in anhydrous DMF (10 mL) under argon was added diisopropylethylamine (0.54 mL, 3.1 mmol) and bis(2-methoxyethyl)aminosulfur trifluoride (0.46 mL, 2.5 mmol) dropwise. The reaction was stirred for 30 min then N,O-dimethylhydroxylamine hydrochloride (0.303 g, 3.1 mmol) was added. After stirring for a further 15 min over an ice bath, the mixture was allowed to warm to room temperature and stirred for 3.5 hrs. H₂O was added and the mixture was extracted with EtOAc. The combined organics were washed with H₂O, saturated aqueous NH₄Cl, saturated aqueous NaHCO₃, and brine then dried over Na₂SO₄ and concentrated in vacuo. Purification by chromatography (45-90% EtOAc-hexanes; EtOAc containing 1% Et₃N) to give N,2-dimethoxy-N-methyl-2-(4-(1-(tris(4-methoxyphenyl)methyl)-1H-pyrazol-4-yl)phenyl)acetamide (0.478 g from two reactions, 32% yield overall).

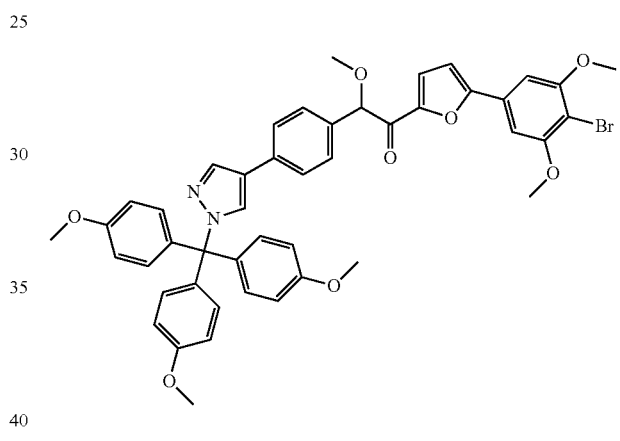

The method used for the final coupling step of Example 12 was used except with a shorter reaction time at room temperature of 70 min. Purification by chromatography (35-90% EtOAc-hexanes; EtOAc containing 1% Et₃N) provided 1-(5-(4-bromo-3,5-dimethoxyphenyl)furan-2-yl)-2-methoxy-2-(4-(1-(tris(4-methoxyphenyl)methyl)-1H-pyrazol-4-yl)phenyl)ethanone as a solid (0.10 g, 18% yield).

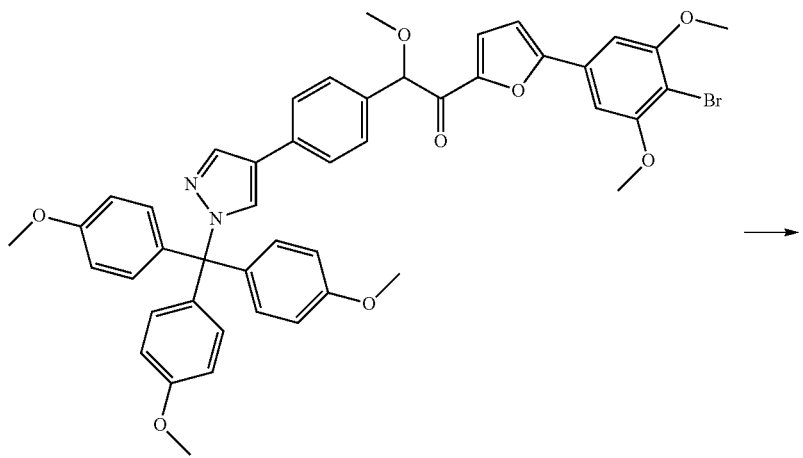

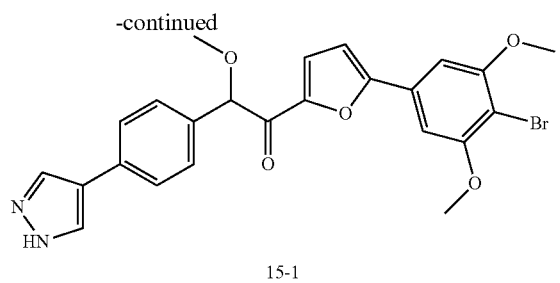

15-1

To a suspension of 1-(5-(4-bromo-3,5-dimethoxyphenyl)furan-2-yl)-2-methoxy-2-(4-(1-(tris(4-methoxyphenyl)methyl)-1H-pyrazol-4-yl)phenyl)ethanone (0.10 g, 0.12 mmol) in MeOH—H$_2$O (22 mL, 10:1) was added pyridinium para-toluenesulfonate (0.046 g, 0.16 mmol). After stirring for 18 hrs at room temperature, saturated aqueous NaHCO$_3$ was added and the volatiles were removed in vacuo. The residue was diluted with a small amount of H$_2$O then extracted with EtOAc. The combined organics were washed with H$_2$O and brine, dried over Na$_2$SO$_4$ and concentrated in vacuo. Purification by chromatography (50-100% EtOAc-hexanes) provided 2-(4-(1H-pyrazol-4-yl)phenyl)-1-(5-(4-bromo-3,5-dimethoxyphenyl)furan-2-yl)-2-methoxyethanone as a yellow foam (0.010 g, 17% yield). MS: m/z 497.0 [M+H]$^+$.

Example 16

1-(5-(4-Bromo-3,5-Dimethoxyphenyl)Furan-2-yl)-2-Methoxy-2-(4-(5-Methylfuran-2-yl)Phenyl)Ethanone

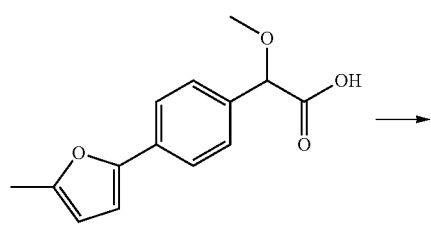

2-Methoxy-2-(4-(5-methylfuran-2-yl)phenyl)acetic acid was synthesized from 4-(5-methylfuran-2-yl)benzaldehyde using the method described for Example 1 (3.3 g, quantitative yield). The product was used without further purification.

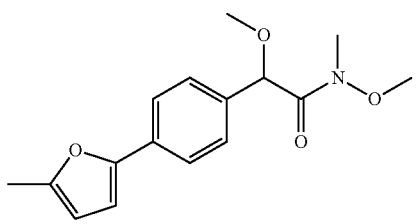

N,2-Dimethoxy-N-methyl-2-(4-(5-methylfuran-2-yl)phenyl)acetamide was synthesized from 2-methoxy-2-(4-(5-methylfuran-2-yl)phenyl)acetic acid following the method used for Example 13. The product was isolated as an orange oil (0.693 g, 18% yield).

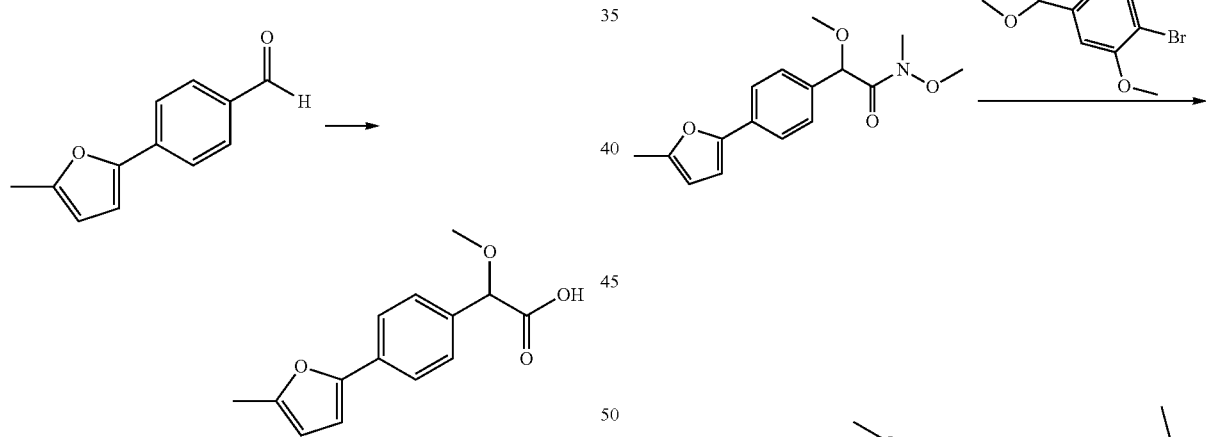

16-1

2-(4-Bromo-3,5-dimethoxyphenyl)furan was coupled with N,2-dimethoxy-N-methyl-2-(4-(5-methylfuran-2-yl)phenyl)acetamide following the method used for the final coupling step of Example 12. Purification by chromatography (30-60% EtOAc-hexanes) provided 1-(5-(4-bromo-3,5-dimethoxyphenyl)furan-2-yl)-2-methoxy-2-(4-(5-methylfuran-2-yl)phenyl)ethanone as a pale orange colored solid (0.172 g, 47% yield). MS: m/z 511.0 [M+H]+.

Example 17

2,3-Dimethoxy-5-(5-(2-Methoxy-2-(4-(5-Methyl-1,3,4-Oxadiazol-2-yl)Phenyl)Acetyl)Furan-2-yl)Benzonitrile

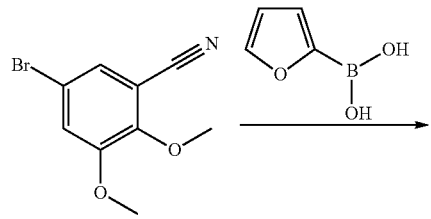

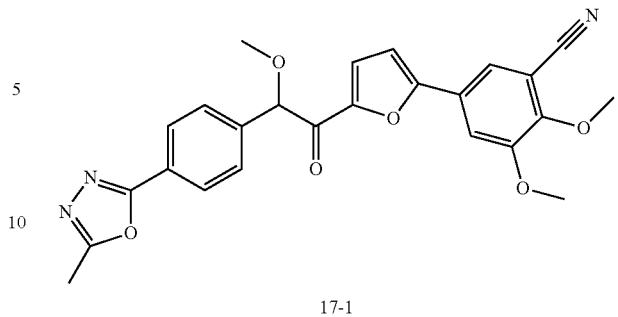

17-1

The method used for the final coupling step of Example 12 was followed for the reaction of 5-(furan-2-yl)-2,3-dimethoxybenzonitrile and N,2-dimethoxy-N-methyl-2-(4-(5-methyl-1,3,4-oxadiazol-2-yl)phenyl)acetamide except that the reaction was performed at −40 to −25° C. then warmed to room temperature. Purification by chromatography (20-100% EtOAc-hexanes) provided 2,3-dimethoxy-5-(5-(2-methoxy-2-(4-(5-methyl-1,3,4-oxadiazol-2-yl)phenyl)acetyl)furan-2-yl)benzonitrile (0.040 g, 13% yield). MS: m/z 460.2 [M+H]+.

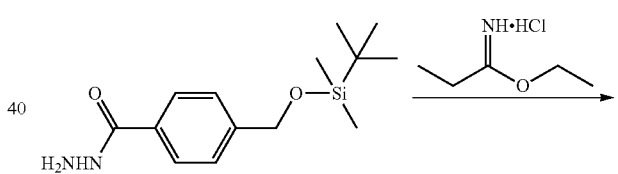

To a mixture of 5-bromo-2,3-dimethoxybenzonitrile (0.958 g, 4.0 mmol), 2-furylboronic acid (0.53 g, 4.7 mmol), dioxane (24 mL), H₂O (8 mL) and Na₂CO₃ (1.1 g, 10.4 mmol) was added tetrakis(triphenylphosphine)palladium (0.23 g, 0.2 mmol). The mixture was degassed by alternately putting under house vacuum and argon three times for several minutes each then heated at 85° C. under argon for 16.5 hrs. After cooling to room temperature, the mixture was diluted with H₂O and extracted with EtOAc. The combined organics were washed with H₂O and brine, dried over Na₂SO₄ and concentrated in vacuo. Purification by chromatography (0-20% EtOAc-hexanes) provided 5-(furan-2-yl)-2,3-dimethoxybenzonitrile as a white solid (0.85 g, 94% yield).

Example 18

1-(5-(4-Bromo-3,5-Dimethoxyphenyl)Furan-2-yl)-2-(4-(5-Ethyl-1,3,4-Oxadiazol-2-yl)Phenyl)-2-Methoxyethanone

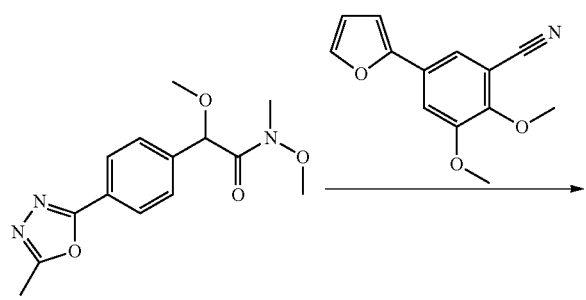

To a solution of 4-(((tert-butyldimethylsilyl)oxy)methyl)benzohydrazide (6.0 g, 21.4 mmol; reported in Tanaka, A. et al. *J. Med. Chem.* 1998, 41, 2390) and ethyl propionimidate hydrochloride (3.5 g, 25.7 mmol; preparation reported in WO2007/73299A1) in EtOH (120 mL) was added Et₃N (2.59 g, 25.7 mmol). The mixture was stirred at room temperature for 1 hr then concentrated in vacuo. The residue was partitioned into EtOAc and H₂O and the organics were washed with H₂O and brine, dried over Na₂SO₄ and concentrated in vacuo. Purification by chromatography (EtOAc-hexanes) gave 2-(4-(((tert-butyldimethylsilyl)oxy)methyl)phenyl)-5-ethyl-1,3,4-oxadiazole as a brown oil (3.0 g, 44% yield).

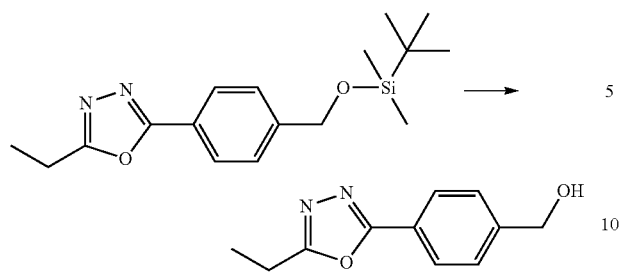
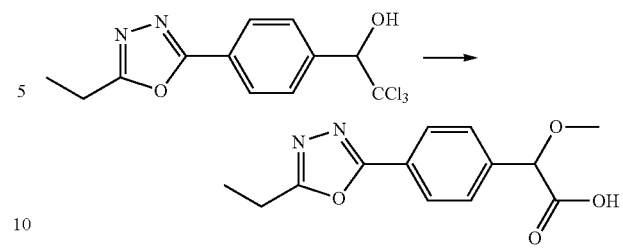

To an ice-cold solution of 2-(4-(((tert-butyldimethylsilyl)oxy)methyl)phenyl)-5-ethyl-1,3,4-oxadiazole (3.0 g, 9.4 mmol) in MeOH (30 mL) was added 1 M HCl (20 mL, 20 mmol) dropwise. The reaction was stirred over ice for 1 hr then concentrated. The residue was quenched with saturated aqueous NaHCO$_3$ and extracted with EtOAc. The combined organics were dried over Na$_2$SO$_4$ and concentrated in vacuo to give (4-(5-ethyl-1,3,4-oxadiazol-2-yl)phenyl)methanol as an off-white solid (1.92 g, 93% yield).

To a solution of 2,2,2-trichloro-1-(4-(5-ethyl-1,3,4-oxadiazol-2-yl)phenyl)ethanol (2.0 g, 6.25 mmol) in anhydr 1,4-dioxane (12.5 mL) and anhydr MeOH (15 mL) was added a solution of NaOH (1.25 g, 31.3 mmol) in anhydr MeOH (15 mL). After stirring for 4 hrs at 55° C., the mixture was cooled to room temperature and concentrated in vacuo. The residue was neutralized with saturated aqueous NH$_4$Cl, acidified carefully with 1 M HCl and extracted with EtOAc. The combined organics were dried over Na$_2$SO$_4$ and concentrated in vacuo. The residue was triturated with Et$_2$O to give 2-(4-(5-ethyl-1,3,4-oxadiazol-2-yl)phenyl)-2-methoxyacetic acid as an off-white solid (1.2 g, 73% yield).

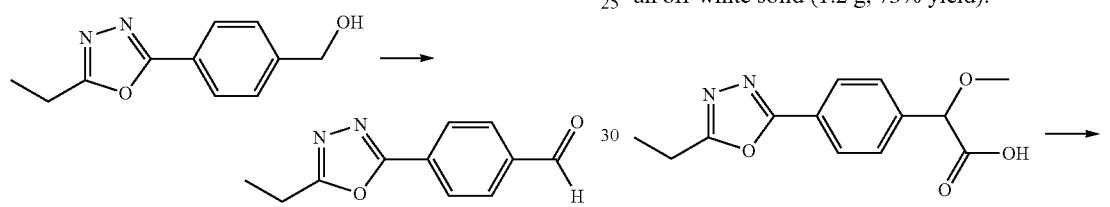

To a solution of (4-(5-ethyl-1,3,4-oxadiazol-2-yl)phenyl)methanol (1.8 g, 8.8 mmol) in CH$_2$Cl$_2$ (50 mL) was added molecular sieves (1.5 g, 4 Å) and the mixture was cooled to 0° C. Pyridinium chlorochromate (2.27 g, 10.5 mmol) was added in portions to the reaction mixture then it was warmed to room temperature. After stirring for 2 hrs, the mixture was filtered through Celite and rinsed with additional CH$_2$Cl$_2$. The filtrate was concentrated in vacuo. Purification by chromatography (EtOAc-hexanes) provided 4-(5-ethyl-1,3,4-oxadiazol-2-yl)benzaldehyde as an off-white solid (1.3 g, 70%).

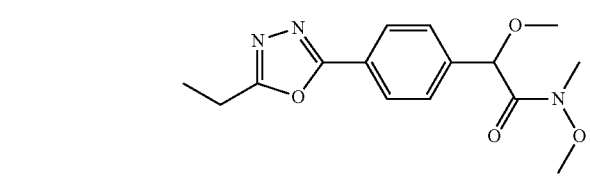

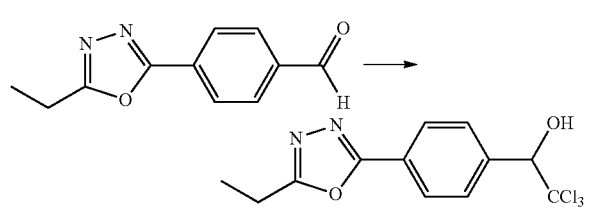

To a solution of 4-(5-ethyl-1,3,4-oxadiazol-2-yl)benzaldehyde (1.6 g, 7.9 mmol) in anhydr DMF (7 mL) was added CHCl$_3$ (2.13 g, 17.8 mmol). After cooling to −10° C., a solution of KOH (0.31 g, 5.5 mmol) in anhydr MeOH (1.5 mL) was added dropwise over 20 min. After stirring at −10° C. for 1 hr, the reaction mixture was quenched with 1 M HCl. The solid formed was collected on a Büchner, washed with H$_2$O and dried under vacuum to give 2,2,2-trichloro-1-(4-(5-ethyl-1,3,4-oxadiazol-2-yl)phenyl)ethanol as a white solid (2.0 g, 80% yield).

The method used for the synthesis of Example 1 was followed for the synthesis of 2-(4-(5-ethyl-1,3,4-oxadiazol-2-yl)phenyl)-N,2-dimethoxy-N-methylacetamide from 2-(4-(5-ethyl-1,3,4-oxadiazol-2-yl)phenyl)-2-methoxyacetic acid. Purification by chromatography (20% EtOAc-hexanes) gave 2-(4-(5-ethyl-1,3,4-oxadiazol-2-yl)phenyl)-N,2-dimethoxy-N-methylacetamide as an amorphous solid (0.55 g, 40% yield).

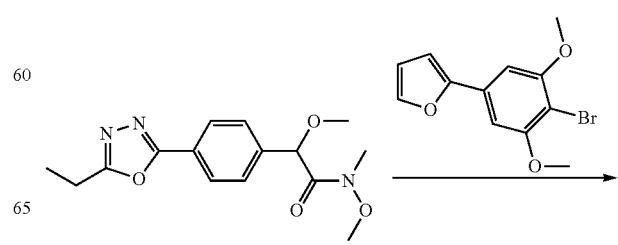

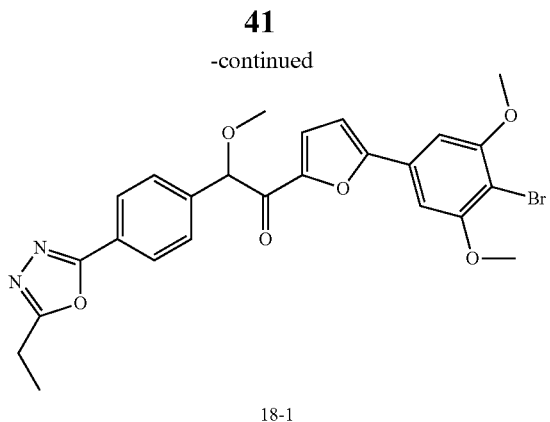

18-1

The method used for the final coupling step of Example 12 was followed for the reaction of 2-(4-bromo-3,5-dimethoxyphenyl)furan with 2-(4-(5-ethyl-1,3,4-oxadiazol-2-yl)phenyl)-N,2-dimethoxy-N-methylacetamide. Purification by chromatography (20-100% EtOAc-hexanes) gave 1-(5-(4-bromo-3,5-dimethoxyphenyl)furan-2-yl)-2-(4-(5-ethyl-1,3,4-oxadiazol-2-yl)phenyl)-2-methoxyethanone as a yellow foam (0.037 g, 12% yield). MS: m/z 527.1 [M+H]⁺.

Example 19

1-(5-(4-Bromo-3,5-Dimethoxyphenyl)Furan-2-yl)-2-(4-(1,1-Dioxidoisothiazolidin-2-yl)Phenyl)-2-Methoxyethanone

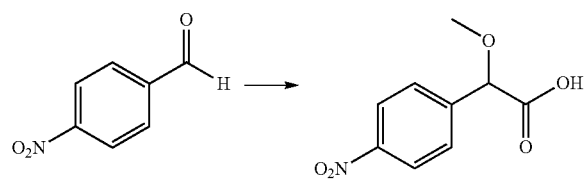

The method used for the synthesis of Example 1 was followed for the synthesis of 2-methoxy-2-(4-nitrophenyl)acetic acid from 4-nitrobenzaldehyde. The acid isolated after aqueous extraction was used without further purification (5.3 g, 76% yield).

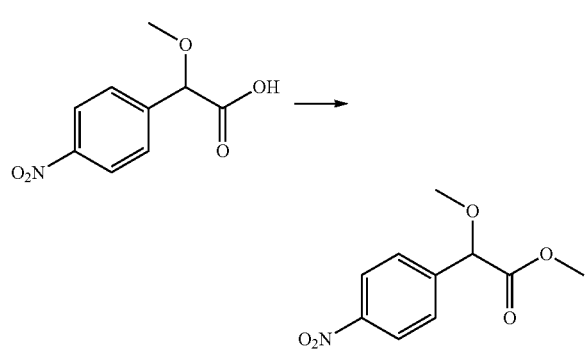

2-Methoxy-2-(4-nitrophenyl)acetic acid was esterified according to the procedure for the synthesis of Example 3. Purification by chromatography (15-22% EtOAc-hexanes) gave methyl 2-methoxy-2-(4-nitrophenyl)acetate as a yellow oil (2.15 g, 38% yield).

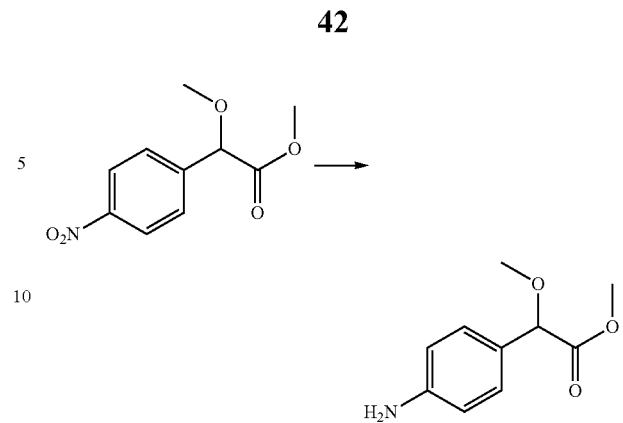

A solution of methyl 2-methoxy-2-(4-nitrophenyl)acetate (0.42 g, 1.87 mmol) in absolute EtOH (15 mL) was degassed by alternately putting under house vacuum and argon three times for several minutes each then 10% Pd/C (0.19 g) was added. The mixture was stirred under H₂ (1 atm.) for 3 hrs then diluted with EtOAc and filtered through a pad of Celite and silica gel. The filtrate was concentrated in vacuo. Purification by chromatography (25-40% EtOAc-hexanes) provided methyl 2-(4-aminophenyl)-2-methoxyacetate as a yellow oil containing impurities (0.6 g from two batches, 77% yield). The compound was used without further purification.

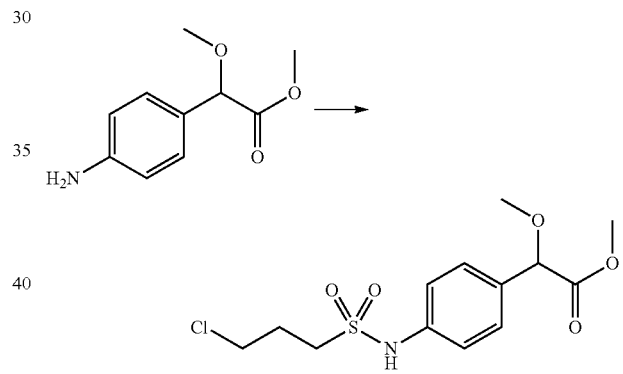

To a solution of methyl 2-(4-aminophenyl)-2-methoxyacetate (0.6 g, 3.07 mmol) in anhydrous pyridine (6 mL) under argon was added 3-chloropropane-1-sulfonyl chloride (0.5 mL, 4.11 mmol) dropwise. The exothermic reaction was cooled briefly over a cold H₂O bath. After stirring for 1 hr, the reaction was diluted with H₂O, 1 M HCl and brine and extracted with EtOAc. The combined organics were washed with 1 M HCl, H₂O and brine then dried over Na₂SO₄ and concentrated in vacuo to give methyl 2-(4-(3-chloropropylsulfonamido)phenyl)-2-methoxyacetate as an orange oil (1.03 g, quant. yield). The product was used without further purification.

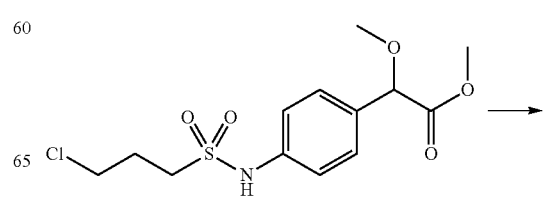

-continued

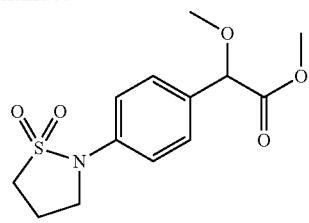

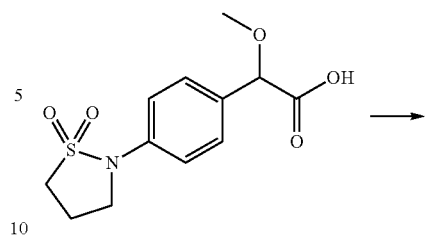

To a solution of methyl 2-(4-(3-chloropropylsulfonamido) phenyl)-2-methoxyacetate (1.03 g, 3.07 mmol) in anhydr DMF (10 mL) was added N,N-diisopropylethylamine (2.0 mL, 11.5 mmol). The mixture was heated at 50° C. under argon for 17 hrs. After cooling to room temperature, the reaction was diluted with $H_2O$, 1 M HCl and brine then extracted with EtOAc. The combined organics were washed with 1 M HCl, $H_2O$ and brine the dried over $Na_2SO_4$ and concentrated in vacuo. The residue was triturated with $Et_2O$-EtOAc. After sitting overnight, the solution was decanted from solids then concentrated in vacuo. Purification by chromatography (50-70% EtOAc-hexanes) provided methyl 2-(4-(1,1-dioxidoisothiazolidin-2-yl)phenyl)-2-methoxyacetate as an impure oil (0.69 g, 75% yield). The product was used in the next synthetic step without further purification.

2-(4-(1,1-Dioxidoisothiazolidin-2-yl)phenyl)-N,2-dimethoxy-N-methylacetamide was synthesized from 2-(4-(1,1-dioxidoisothiazolidin-2-yl)phenyl)-2-methoxyacetic acid following the procedure for the synthesis of Example 13. Purification by chromatography (0-4% EtOH-EtOAc) gave an oil that was triturated with $Et_2O$. The solid was dried under vacuum to give pure 2-(4-(1,1-dioxidoisothiazolidin-2-yl)phenyl)-N,2-dimethoxy-N-methylacetamide as a light yellow powder (0.182 g, 64% yield).

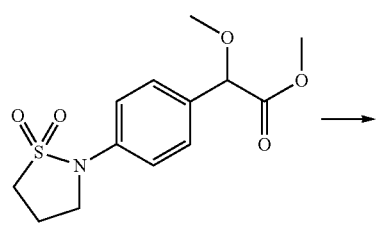

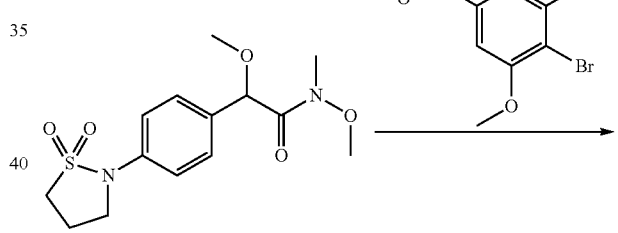

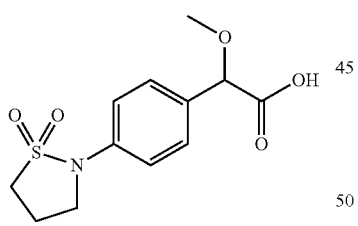

To a solution of methyl 2-(4-(1,1-dioxidoisothiazolidin-2-yl)phenyl)-2-methoxyacetate (0.48 g, 1.6 mmol) in MeOH (21 mL) was added 1 M NaOH (7 mL, 7 mmol) slowly. After stirring at room temperature for 23 hrs, the volatiles were removed in vacuo and the residue was dissolved in $H_2O$. EtOAc was added to the aqueous solution and saturated aqueous $NH_4Cl$ and 1 M HCl were added slowly until the pH ~3. The mixture was extracted with EtOAc then the aqueous layer was acidified to pH 1 and extracted with EtOAc again. The combined organics were washed with $H_2O$ and brine, dried over $Na_2SO_4$ and concentrated in vacuo to give 2-(4-(1,1-dioxidoisothiazolidin-2-yl)phenyl)-2-methoxyacetic acid as a yellow foam (0.378 g, 82% yield). The product was used in the next synthetic step without further purification.

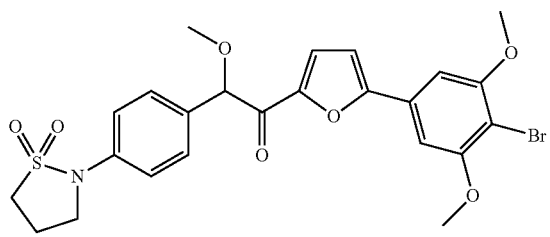

19-1

1-(5-(4-Bromo-3,5-dimethoxyphenyl)furan-2-yl)-2-(4-(1,1-dioxidoisothiazolidin-2-yl)phenyl)-2-methoxyethanone was synthesized from 2-(4-(1,1-dioxidoisothiazolidin-2-yl)phenyl)-N,2-dimethoxy-N-methylacetamide and 2-(4-bromo-3,5-dimethoxyphenyl)furan following the procedure used for the synthesis of Example 12. Purification by chromatography (EtOAc-hexanes) provided Example 19 as a yellow solid (0.111 g, 37% yield). MS: m/z 550.1 [M+H]$^+$.

Example 20

1-(5-(4-Bromo-3,5-Dimethoxyphenyl)Furan-2-yl)-2-Methoxy-2-(Quinolin-5-yl)Ethanone

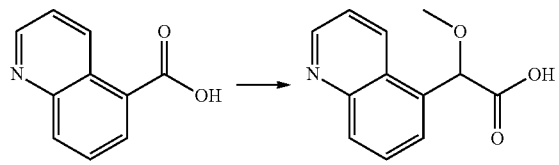 [SMILES: O=C(O)c1cccc2ncccc12 ; COC(C(=O)O)c1cccc2ncccc12]

To an ice-cold solution of quinoline-5-carbaldehyde (3.5 g, 22.3 mmol) in anhydr MeOH (30 mL) and anhydr dioxane (30 mL) was added several drops of a solution of KOH (6.2 g, 113.4 mmol) in MeOH (30 mL). Bromoform (2.5 mL, 30 mmol) was added, then the remaining KOH/MeOH solution was added over a period of 10 min. After stirring for 30 min the reaction mixture was allowed to warm slowly to room temperature overnight then concentrated to dryness. After dissolving in a minimum amount of H$_2$O, the residue was acidified to pH 1 with concentrated HCl. The aqueous mixture was extracted with EtOAc several times with the addition of brine to the aqueous layer during extraction. The combined organics were washed with brine, dried over Na$_2$SO$_4$ and concentrated in vacuo to give 2-methoxy-2-(quinolin-5-yl)acetic acid as a semisolid (2.8 g, 58% yield). The product was used without further purification.

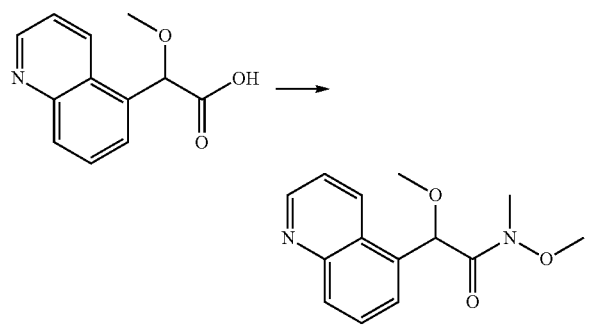

To an ice-cold solution of 2-methoxy-2-(quinolin-5-yl)acetic acid (2.8 g, 12.9 mmol) in anhydrous CH$_2$Cl$_2$ (50 mL) and NMM (3.1 mL, 29 mmol) under argon was added isobutyl chloroformate (1.9 mL, 14 mmol) dropwise. After stirring over an ice bath for 40 min, N,O-dimethylhydroxylamine hydrochloride (1.63 g, 16.8 mmol) was added in three aliquots over a period of 15 min. The mixture was stirred for 15 min then the ice bath was removed. After 24 hrs, saturated aqueous NaHCO$_3$ was added and stirred for 30 min. The layers were separated and the aqueous layer was extracted with CH$_2$Cl$_2$. The combined organics were washed with saturated aqueous NaHCO$_3$, H$_2$O and brine, dried over Na$_2$SO$_4$ and concentrated in vacuo. Purification by chromatography (0-100% EtOAc-hexanes) gave N,2-dimethoxy-N-methyl-2-(quinolin-5-yl)acetamide as an oil which became crystalline upon standing (1.8 g, 60% yield).

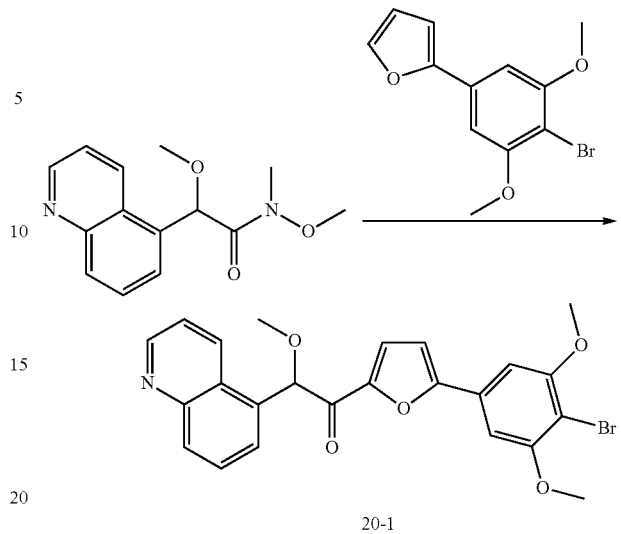

20-1

1-(5-(4-Bromo-3,5-dimethoxyphenyl)furan-2-yl)-2-methoxy-2-(quinolin-5-yl)ethanone was synthesized from N,2-dimethoxy-N-methyl-2-(quinolin-5-yl)acetamide and 2-(4-bromo-3,5-dimethoxyphenyl)furan following the procedure used for the synthesis of Example 12. Purification by chromatography (EtOAc-hexanes) provided 1-(5-(4-bromo-3,5-dimethoxyphenyl)furan-2-yl)-2-methoxy-2-(quinolin-5-yl)ethanone as a light yellow foam (0.102 g, 46% yield). MS: m/z 482.1 [M+H]$^+$.

Example 21

1-(5-(3,5-Dimethoxy-4-Methylphenyl)Furan-2-yl)-2-Methoxy-2-(4-(5-Methyl-1,3,4-Oxadiazol-2-yl)Phenyl)Ethanone

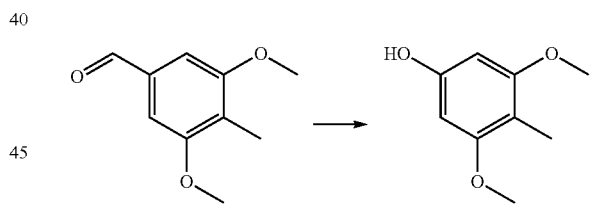

To a solution of 3,5-dimethoxy-4-methylbenzaldehyde (3.0 g, 16.8 mmol) in CH$_2$Cl$_2$ (35 mL) was added meta-chloroperoxybenzoic acid (77% purity; 5.8 g, 25.9 mmol). After stirring at room temperature for 19 hrs, additional meta-chloroperoxybenzoic acid (77% purity; 3.5 g, 15.6 mmol) was added. After heating for 4 hrs at 40° C. and cooling to room temperature, 10% aqueous Na$_2$S$_2$O$_5$ was added and the mixture was stirred for 30 min. The mixture was diluted with CH$_2$Cl$_2$ and the layers separated. The organics were washed with 10% aqueous Na$_2$S$_2$O$_5$, ~5% aqueous NaHCO$_3$ and brine then dried over MgSO$_4$ and concentrated to give 3,5-dimethoxy-4-methylphenyl formate as a yellow solid (2.9 g, 88% yield).

To a solution of 3,5-dimethoxy-4-methylphenyl formate (2.9 g, 14.8 mmol) in wet MeOH (81 mL) was added K$_2$CO$_3$ (8.1 g, 58.6 mmol). The mixture was stirred for 2 hrs at room temperature then H$_2$O (2-3 mL) was added. After stirring for 21 hrs, the mixture was diluted with H$_2$O, acidified with 6M HCl to pH 3-4, and extracted with EtOAc. The combined organics were washed with brine, dried over Na₂SO₄ and concentrated in vacuo. Purification by chromatography (0-35% EtOAc-hexanes) gave 3,5-dimethoxy-4-methylphenol as an impure yellow powder (0.71 g, 29% yield).

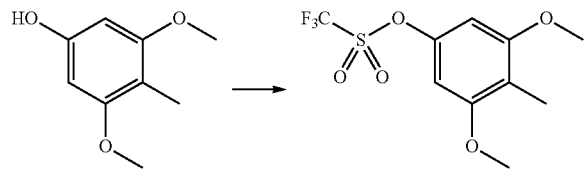 [SMILES: COc1cc(O)cc(OC)c1C ; COc1cc(OS(=O)(=O)C(F)(F)F)cc(OC)c1C]

To a suspension of 3,5-dimethoxy-4-methylphenol in anhydr CH₂Cl₂ (10 mL) under argon was added dry pyridine (0.4 mL, 4.9 mmol) then the mixture was cooled over an ice bath. Trifluoromethanesulfonic anhydride (0.52 g, 3.1 mmol) was added dropwise and the reaction was stirred for 1 hr. Saturated aqueous NaHCO₃ was added and stirred then it was warmed to room temperature. The mixture was diluted with CH₂Cl₂ and the layers were separated. The organics were washed with H₂O and saturated aqueous NaHCO₃ then dried over MgSO₄ and concentrated in vacuo to give 3,5-dimethoxy-4-methylphenyl trifluoromethanesulfonate as a yellow oil (0.508 g, 60% yield). The product was used without further purification.

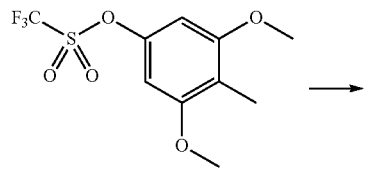

To a solution of 3,5-dimethoxy-4-methylphenyl trifluoromethanesulfonate (0.50 g, 1.67 mmol) in DME (15 mL) was added 2-furylboronic acid (0.245 g, 2.2 mmol), LiCl (0.149 g, 3.5 mmol), 2 M aqueous Na₂CO₃ (1.8 mL, 3.6 mmol) and tetrakis(triphenylphosphine)palladium (0.098 g, 0.085 mmol) and the mixture was degassed as described previously. The reaction was heated at 80° C. under argon for 22 hrs. After cooling to room temperature, the reaction was diluted with H₂O and extracted with EtOAc. The combined organics were washed with H₂O, saturated aqueous NH₄Cl, H₂O and brine, dried over Na₂SO₄ and concentrated in vacuo. Purification by chromatography (0-25% Et₂O-hexanes) gave 2-(3,5-dimethoxy-4-methylphenyl)furan as a white solid (0.28 g, 77% yield).

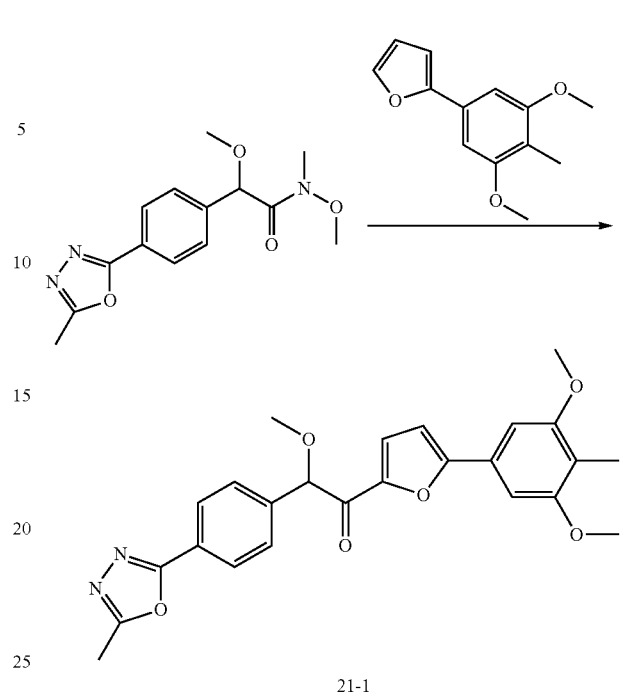

21-1

N,2-Dimethoxy-N-methyl-2-(4-(5-methyl-1,3,4-oxadiazol-2-yl)phenyl)acetamide was reacted with 2-(3,5-dimethoxy-4-methylphenyl)furan according to the procedure used for the synthesis of Example 12. Purification by chromatography (EtOAc-hexanes) gave 1-(5-(3,5-dimethoxy-4-methylphenyl)furan-2-yl)-2-methoxy-2-(4-(5-methyl-1,3,4-oxadiazol-2-yl)phenyl)ethanone as a yellow foam (0.148 g, 29% yield). MS: m/z 449.2 [M+H]⁺.

Example 22

1-(5-(4-Bromo-3,5-Dimethoxyphenyl)Furan-2-yl)-2-(4-(5-Cyclopropyl-1,3,4-Oxadiazol-2-yl)Phenyl)-2-Methoxyethanone

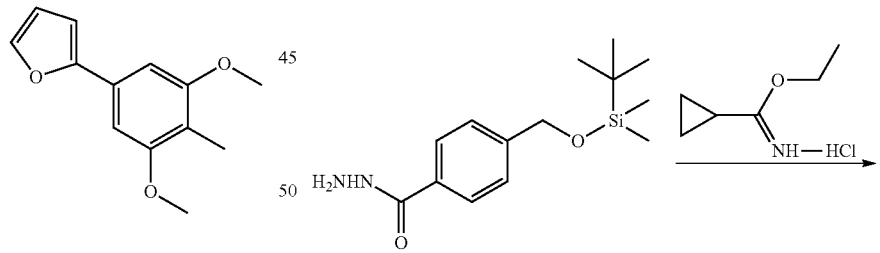

4-(((Tert-butyldimethylsilyl)oxy)methyl)benzohydrazide was reacted with ethyl cyclopropanecarbimidate hydrochloride according to the procedure used for the synthesis of Example 18. Purification by chromatography (EtOAc-hexanes) gave 2-(4-(((tert-butyldimethylsilyl)oxy)methyl)phenyl)-5-cyclopropyl-1,3,4-oxadiazole as a brown oil (3.7 g, 40% yield).

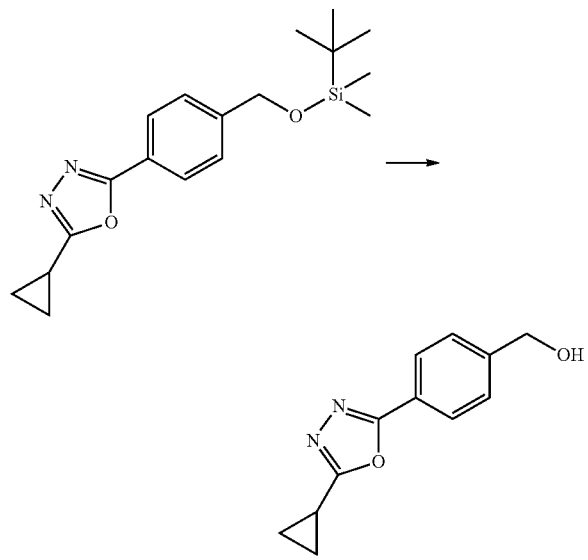

(4-(5-Cyclopropyl-1,3,4-oxadiazol-2-yl)phenyl)methanol was synthesized from 2-(4-(((tert-butyldimethylsilyl)oxy)methyl)phenyl)-5-cyclopropyl-1,3,4-oxadiazole according to the procedure for Example 18. (4-(5-Cyclopropyl-1,3,4-oxadiazol-2-yl)phenyl)methanol was isolated as an off-white solid and was used in the next synthetic step without further purification (2.2 g, 84% yield).

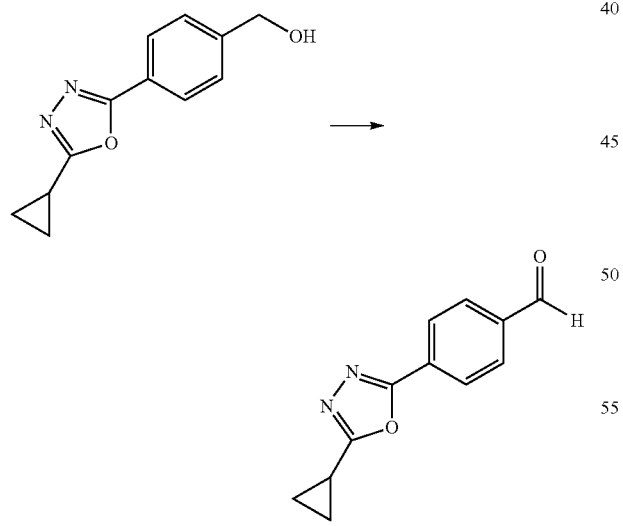

4-(5-Cyclopropyl-1,3,4-oxadiazol-2-yl)benzaldehyde was synthesized from (4-(5-cyclopropyl-1,3,4-oxadiazol-2-yl)phenyl)methanol according to the procedure for Example 18. Purification by chromatography (EtOAc-hexanes) gave 4-(5-cyclopropyl-1,3,4-oxadiazol-2-yl)benzaldehyde as a white solid (1.8 g, 82% yield).

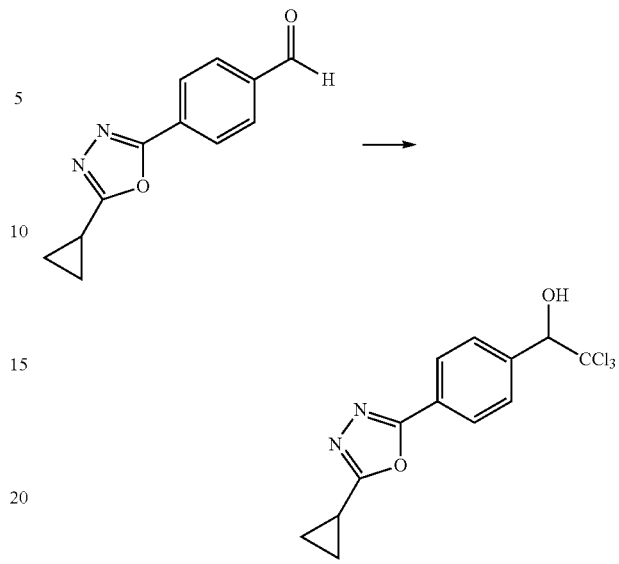

2,2,2-Trichloro-1-(4-(5-cyclopropyl-1,3,4-oxadiazol-2-yl)phenyl)ethanol was synthesized from 4-(5-cyclopropyl-1,3,4-oxadiazol-2-yl)benzaldehyde according to the procedure for the synthesis of Example 18. The product was isolated as a white solid and used without further purification (2.5 g, 89% yield).

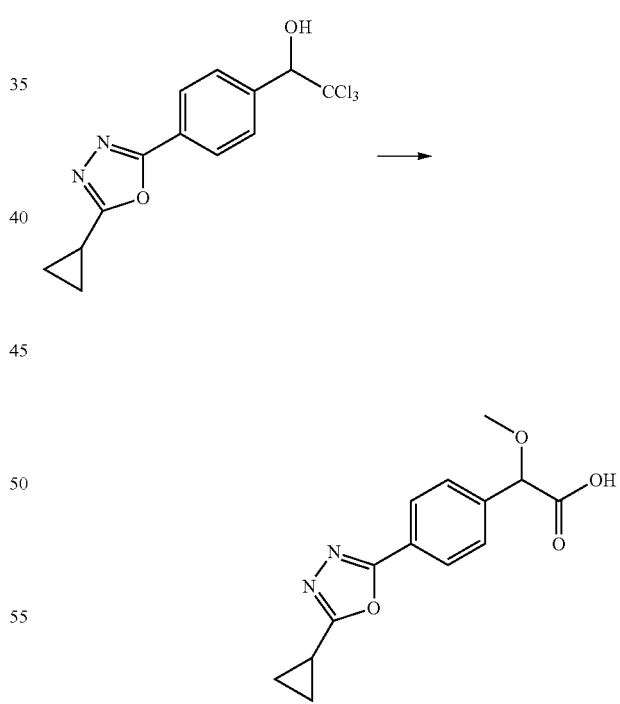

2-(4-(5-Cyclopropyl-1,3,4-oxadiazol-2-yl)phenyl)-2-methoxyacetic acid was synthesized from 2,2,2-trichloro-1-(4-(5-cyclopropyl-1,3,4-oxadiazol-2-yl)phenyl)ethanol following the procedure used for the synthesis of Example 18. The product was isolated as a yellow semi-solid and used for the next synthetic step without further purification (1.8 g, 90% yield).

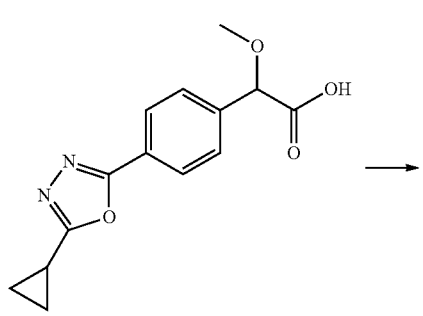

2-(4-(5-Cyclopropyl-1,3,4-oxadiazol-2-yl)phenyl)-N,2-dimethoxy-N-methylacetamide was synthesized from 2-(4-(5-cyclopropyl-1,3,4-oxadiazol-2-yl)phenyl)-2-methoxyacetic acid according to the procedure for the synthesis of Example 18. The product was isolated as a white semi-solid (0.56 g, 27% yield).

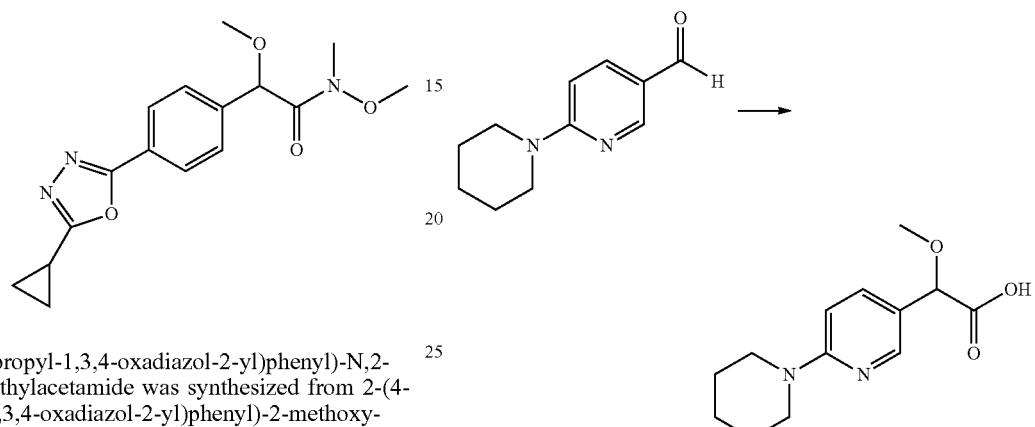

22-1

2-(4-(5-Cyclopropyl-1,3,4-oxadiazol-2-yl)phenyl)-N,2-dimethoxy-N-methylacetamide was reacted with 2-(4-bromo-3,5-dimethoxyphenyl)furan according to the procedure for the synthesis of Example 12. Purification by chromatography (EtOAc-hexanes) gave 1-(5-(4-bromo-3,5-dimethoxyphenyl)furan-2-yl)-2-(4-(5-cyclopropyl-1,3,4-oxadiazol-2-yl)phenyl)-2-methoxyethanone as a yellow foam (0.126 g, 31% yield). MS: m/z 539.2 [M+H]+.

Example 23

1-(5-(4-Bromo-3,5-Dimethoxyphenyl)Furan-2-yl)-2-Methoxy-2-(6-(Piperidin-1-yl)Pyridin-3-yl)Ethanone

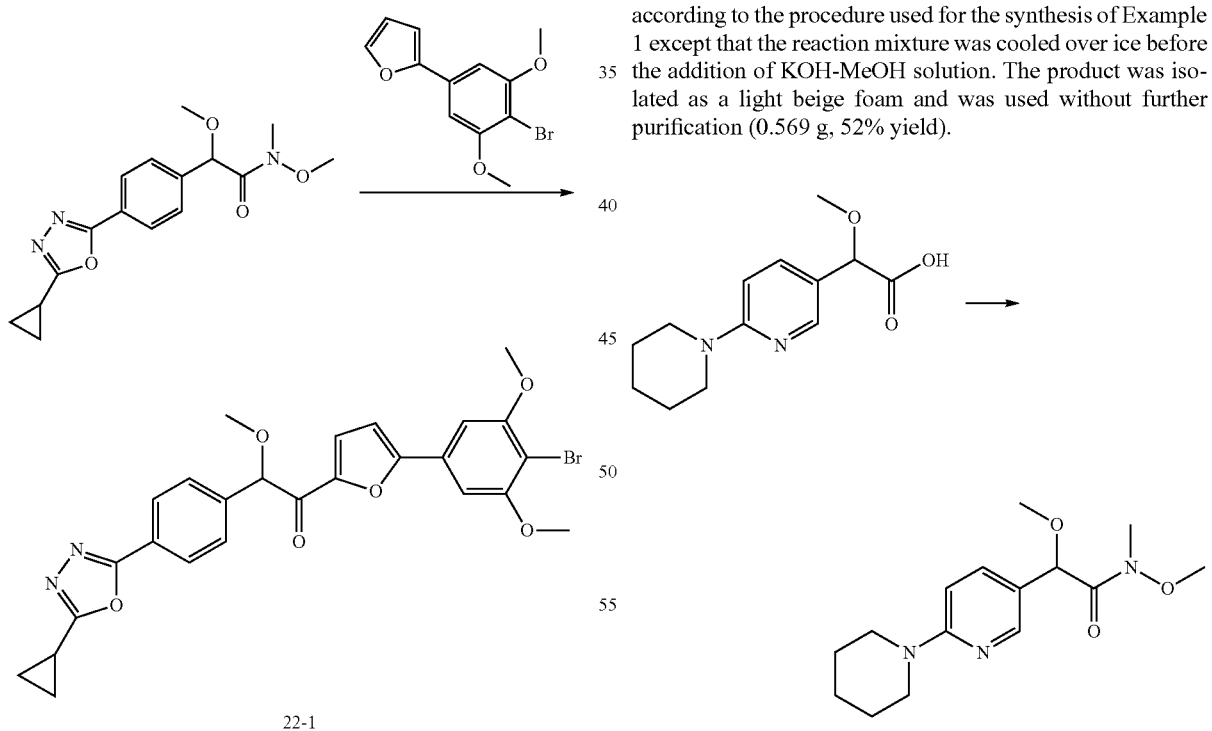

2-Methoxy-2-(6-(piperidin-1-yl)pyridin-3-yl)acetic acid was synthesized from 6-(piperidin-1-yl)nicotinaldehyde according to the procedure used for the synthesis of Example 1 except that the reaction mixture was cooled over ice before the addition of KOH-MeOH solution. The product was isolated as a light beige foam and was used without further purification (0.569 g, 52% yield).

N,2-Dimethoxy-N-methyl-2-(6-(piperidin-1-yl)pyridin-3-yl)acetamide was synthesized from 2-methoxy-2-(6-(piperidin-1-yl)pyridin-3-yl)acetic acid according to the procedure used for the synthesis of Example 13. Purification by chromatography (50-100% EtOAc-hexanes) gave the product as an orange oil (0.295 g, 46% yield).

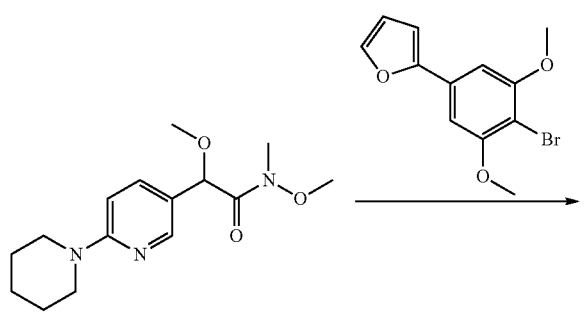

ronic acid according to the procedure used in the synthesis of Example 21. Purification by chromatography (20-40% EtOAc-hexanes) gave 4-(furan-2-yl)-2,6-dimethoxyphenol as a light orange solid (1.95 g, 79% yield).

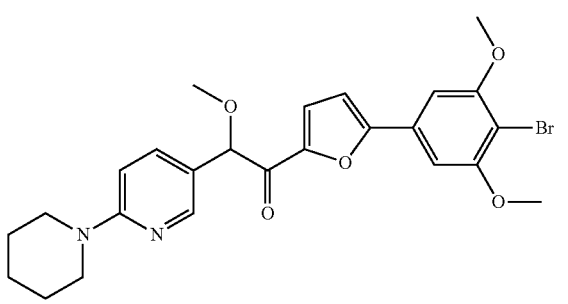

23-1

N,2-Dimethoxy-N-methyl-2-(6-(piperidin-1-yl)pyridin-3-yl)acetamide was reacted with 2-(4-bromo-3,5-dimethoxyphenyl)furan according to the procedure used for Example 12. Purification by chromatography (20-75% EtOAc-hexanes) gave 1-(5-(4-bromo-3,5-dimethoxyphenyl)furan-2-yl)-2-methoxy-2-(6-(piperidin-1-yl)pyridin-3-yl)ethanone as a light yellow solid (0.328 g, 65% yield). MS: m/z 515.4 [M+H]$^+$.

Example 24

2,6-Dimethoxy-4-(5-(2-Methoxy-2-(4-Morpholinophenyl)Acetyl)Furan-2-yl)Phenyl Benzoate

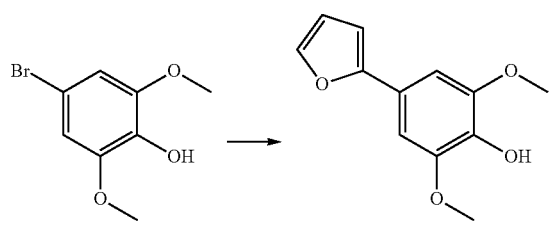 [SMILES: COc1cc(Br)cc(OC)c1O ; COc1cc(-c2ccco2)cc(OC)c1O]

4-Bromo-2,6-dimethoxyphenol (Lee, H.; et al. *Tetrahedron Letters*, 2004, 45, 1019) was coupled with 2-furylbo-

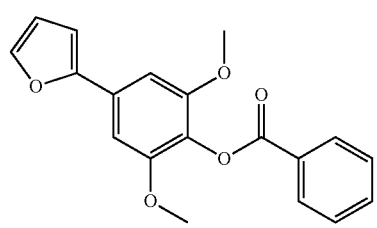

To a solution of 4-(furan-2-yl)-2,6-dimethoxyphenol (1.3 g, 5.9 mmol) in anhydr CH$_2$Cl$_2$ (20 mL) under argon was added Et$_3$N (1.6 mL, 11.5 mmol) then the mixture was cooled over an ice bath. Benzoyl chloride (0.75 mL, 6.4 mmol) was added dropwise and the reaction was stirred for 3 hrs. 10% aqueous NaHCO$_3$ and CH$_2$Cl$_2$ were added, stirred, and the layers were separated. The organics were washed with H$_2$O and saturated aqueous NaHCO$_3$, dried over MgSO$_4$ and concentrated in vacuo. Purification by chromatography (0-25% EtOAc-hexanes) gave 4-(furan-2-yl)-2,6-dimethoxyphenyl benzoate as a light yellow solid (0.54 g isolated from chromatography of approximately half of the crude product; 57% yield).

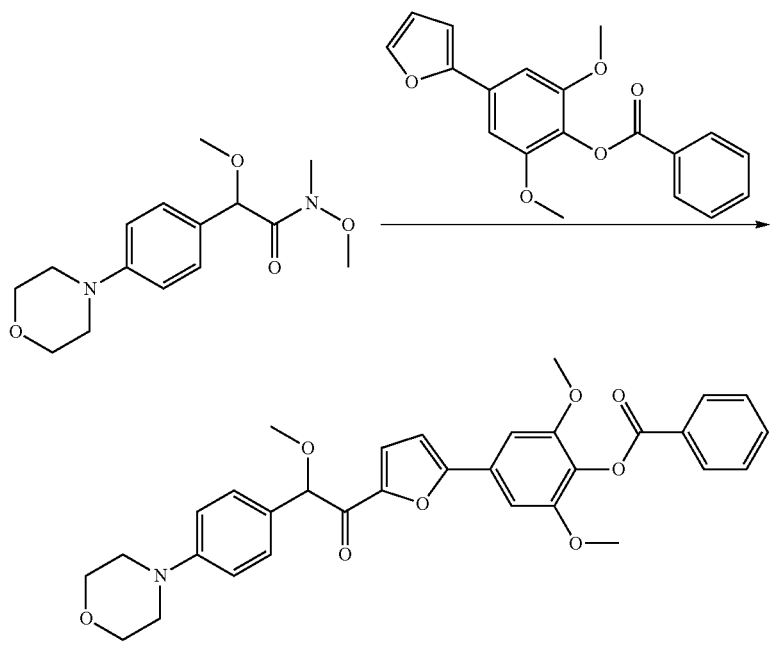

4-(Furan-2-yl)-2,6-dimethoxyphenyl benzoate was reacted with N,2-dimethoxy-N-methyl-2-(4-morpholinophenyl)acetamide according to the procedure described for the synthesis of Example 12 except that the reaction was warmed to only 0° C. Purification by chromatography (EtOAc-hexanes) provided 2,6-dimethoxy-4-(5-(2-methoxy-2-(4-morpholinophenyl)acetyl)furan-2-yl)phenyl benzoate as a yellow solid (0.257 g, 50% yield). MS: m/z 558.2 [M+H]$^+$.

Example 25

1-(5-(4-Bromo-3,5-Dimethoxyphenyl)Furan-2-yl)-2-Methoxy-2-(1-Methyl-1H-Benzo[D][1,2,3]Triazol-5-yl)Ethanone

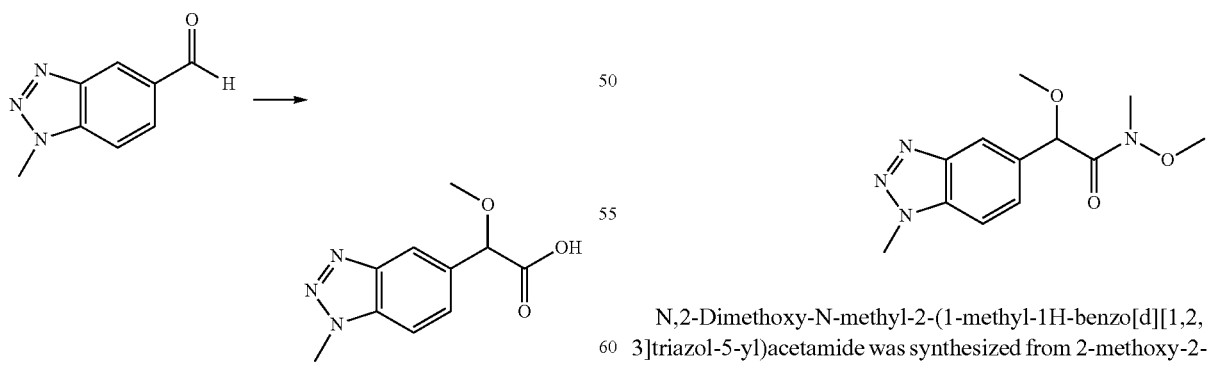

2-Methoxy-2-(1-methyl-1H-benzo[d][1,2,3]triazol-5-yl)acetic acid was synthesized from 1-methyl-1H-benzo[d][1,2,3]triazole-5-carbaldehyde according to the procedure for the synthesis of Example 23. The product was isolated as a yellow solid (1.5 g, 96% yield).

N,2-Dimethoxy-N-methyl-2-(1-methyl-1H-benzo[d][1,2,3]triazol-5-yl)acetamide was synthesized from 2-methoxy-2-(1-methyl-1H-benzo[d][1,2,3]triazol-5-yl)acetic acid according to the method used for the synthesis of Example 13. Purification by chromatography (60-100% EtOAc-hexanes) gave N,2-dimethoxy-N-methyl-2-(1-methyl-1H-benzo[d][1,2,3]triazol-5-yl)acetamide as a yellow solid (1.02 g, 57% yield).

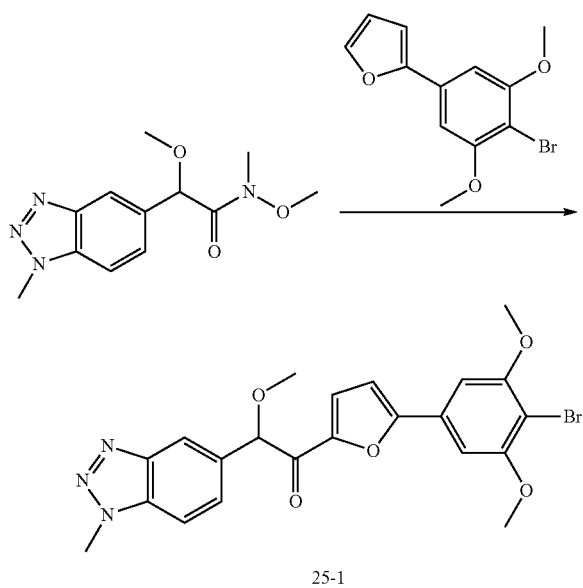

N,2-Dimethoxy-N-methyl-2-(1-methyl-1H-benzo[d][1,2,3]triazol-5-yl)acetamide was coupled with 2-(4-bromo-3,5-dimethoxyphenyl)furan according to the procedure for the synthesis of Example 13. Purification by chromatography provided 1-(5-(4-bromo-3,5-dimethoxyphenyl)furan-2-yl)-2-methoxy-2-(1-methyl-1H-benzo[d][1,2,3]triazol-5-yl)ethanone as a light yellow foam (0.153 g, 34% yield). MS: m/z 486.1 [M+1-1]$^+$.

Example 26

1-(5-(4-Bromo-3,5-Dimethoxyphenyl)Furan-2-yl)-2-Methoxy-2-(4-(Morpholinomethyl)Phenyl)Ethanone

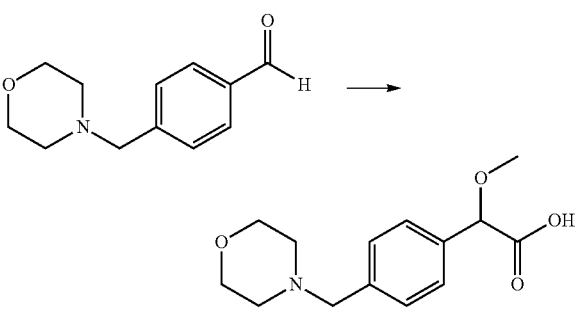

2-Methoxy-2-(4-(morpholinomethyl)phenyl)acetic acid was synthesized from 4-(morpholinomethyl)benzaldehyde following the procedure for the synthesis of Example 23. Following the reaction, the volatiles were removed in vacuo. The residue was redissolved in a minimum amount of H$_2$O and acidified with 1 M HCl to pH 3. The aqueous layer was concentrated in vacuo and the residue was suspended in MeOH and sonicated and warmed slightly. The mixture was filtered through Celite and concentrated in vacuo to give a white solid (3 g, quant. yield). The product was taken on to the next synthetic step without purification.

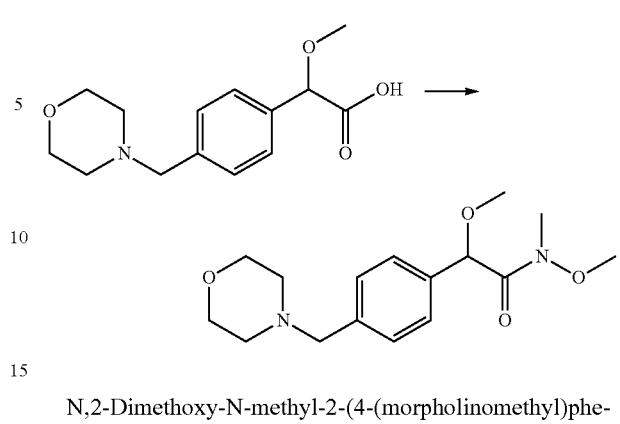

N,2-Dimethoxy-N-methyl-2-(4-(morpholinomethyl)phenyl)acetamide was synthesized from 2-methoxy-2-(4-(morpholinomethyl)phenyl)acetic acid following the procedure used for Example 13. Purification by chromatography (0-7% NH$_3$-MeOH solution in CH$_2$Cl$_2$; 0.7 M NH$_3$-MeOH) gave N,2-dimethoxy-N-methyl-2-(4-(morpholinomethyl)phenyl)acetamide as an orange oil (0.743 g, 41% yield).

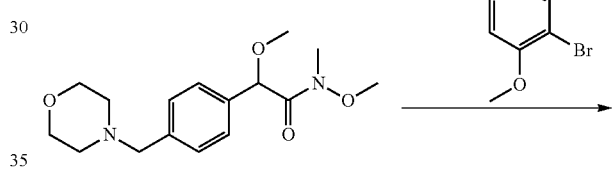

N,2-Dimethoxy-N-methyl-2-(4-(morpholinomethyl)phenyl)acetamide was coupled with 2-(4-bromo-3,5-dimethoxyphenyl)furan following the procedure of Example 12. Purification by chromatography (0-9% NH$_3$-MeOH in CH$_2$Cl$_2$; 0.7 M NH$_3$-MeOH used) gave a mixture which was digested with EtOAc at 30-40° C. After cooling to room temperature, the crystals were collected on a Büchner, rinsed with EtOAc and dried in vacuo to give 1-(5-(4-bromo-3,5-dimethoxyphenyl)furan-2-yl)-2-methoxy-2-(4-(morpholinomethyl)phenyl)ethanone as a white solid. A second batch was also isolated (0.125 g for two batches, 13% yield). MS: m/z 530.1 [M+H]⁺.

Example 27

1-(5-(3,5-Dimethoxyphenyl)Furan-2-yl)-2-Methoxy-2-(4-Morpholinophenyl)Ethanone

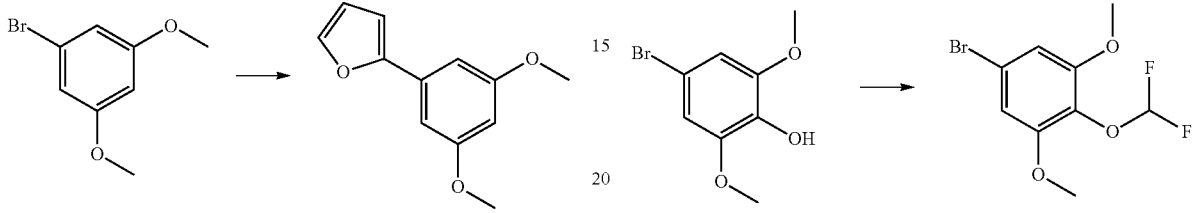

1-Bromo-3,5-dimethoxybenzene was coupled with 2-furylboronic acid following the procedure for Example 21. 2-(3,5-Dimethoxyphenyl)furan was isolated as a colorless liquid (0.746 g, 79% yield).

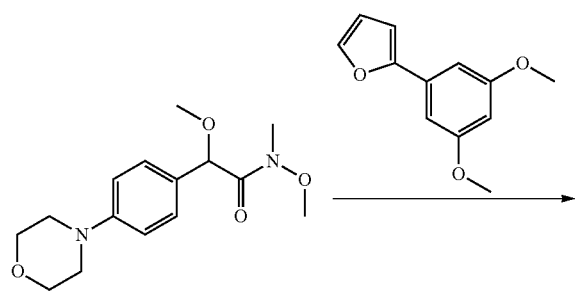

N,2-Dimethoxy-N-methyl-2-(4-morpholinophenyl)acetamide was coupled with 2-(3,5-dimethoxyphenyl)furan following the procedure of Example 12. 1-(5-(3,5-Dimethoxyphenyl)furan-2-yl)-2-methoxy-2-(4-morpholinophenyl) ethanone was isolated as a yellow oily foam (0.343 g, 62% yield). MS: m/z 438.2 [M+H]⁺.

Example 28

1-(5-(4-(Difluoromethoxy)-3,5-Dimethoxyphenyl)Furan-2-yl)-2-Methoxy-2-(4-Morpholinophenyl)Ethanone

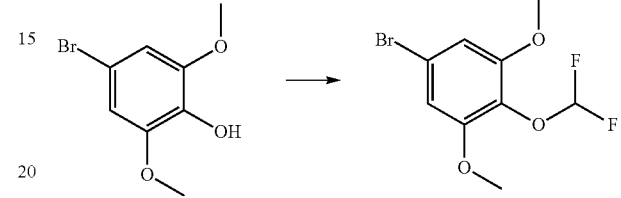

5-Bromo-2-(difluoromethoxy)-1,3-dimethoxybenzene was synthesized from 4-bromo-2,6-dimethoxyphenol according to the procedure of Zafrani, Y. *Tetrahedron* 2009, 65, 5278 as follows. To a solution of 4-bromo-2,6-dimethoxyphenol (1.08 g, 4.6 mmol) in MeCN (27 mL) was added a solution of KOH (5.0 g, 89 mmol) in H₂O (27 mL). The mixture was immediately cooled over a −78° C. bath and diethyl(bromodifluoromethyl)phosphonate (1.6 mL, 8.9 mmol) was added. The flask was sealed with a septum and the cold bath was removed. The mixture was stirred for a total of 3.5 hrs during which time the septum was ejected from the flask. The reaction was diluted with EtOAc and the layers were separated. The aqueous layer was extracted with EtOAc and the combined organics were washed with 1 M NaOH, H₂O and brine then dried over Na₂SO₄ and concentrated in vacuo. Purification by chromatography (0-30% EtOAc-hexanes) provided 5-bromo-2-(difluoromethoxy)-1,3-dimethoxybenzene as a white solid (0.808 g, 62% yield).

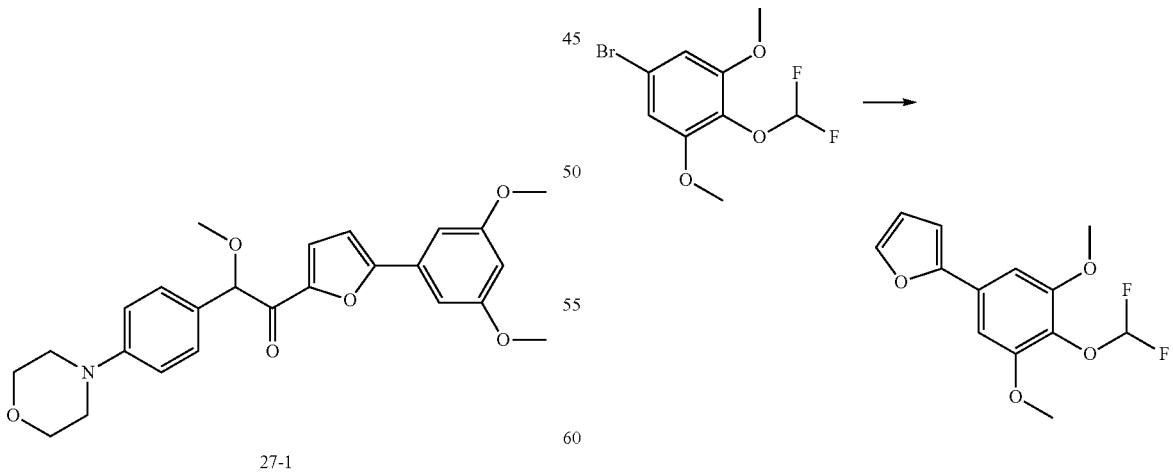

5-Bromo-2-(difluoromethoxy)-1,3-dimethoxybenzene was coupled with 2-furylboronic acid following the procedure for the synthesis of Example 21. Purification by chromatography (0-30% EtOAc-hexanes) provided 2-(4-(difluoromethoxy)-3,5-dimethoxyphenyl)furan as a white crystalline material (0.555 g, 67% yield).

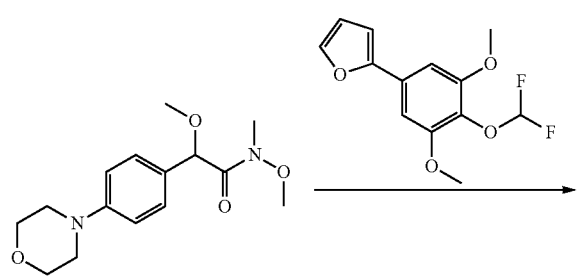

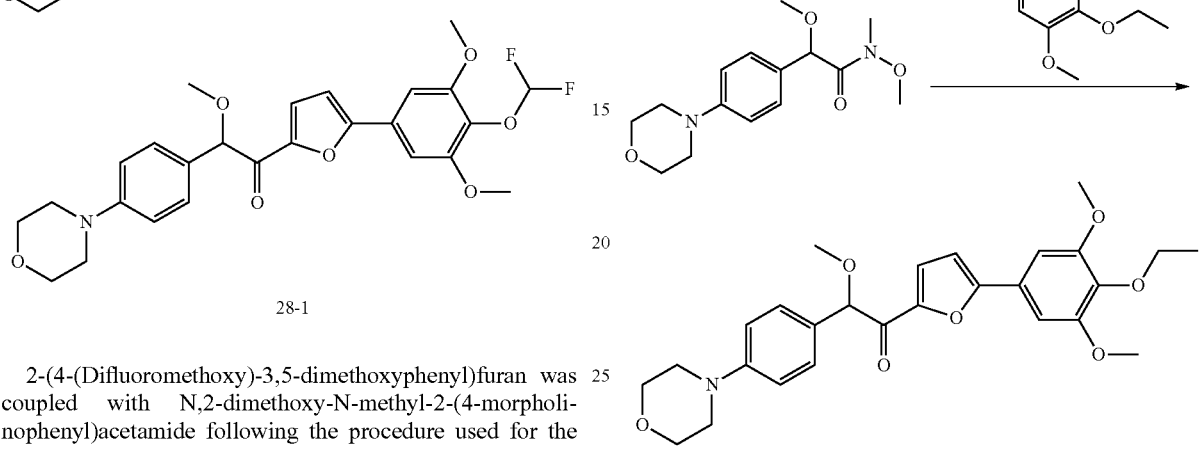

28-1

2-(4-(Difluoromethoxy)-3,5-dimethoxyphenyl)furan was coupled with N,2-dimethoxy-N-methyl-2-(4-morpholinophenyl)acetamide following the procedure used for the synthesis of Example 12. Purification by chromatography (EtOAc-hexanes) provided 1-(5-(4-(difluoromethoxy)-3,5-dimethoxyphenyl)furan-2-yl)-2-methoxy-2-(4-morpholinophenyl)-ethanone as a brown oil (0.021 g, 6% yield). MS: m/z 504.2 [M+H]$^+$.

Example 29

1-(5-(4-Ethoxy-3,5-Dimethoxyphenyl)Furan-2-yl)-2-Methoxy-2-(4-Morpholinophenyl)Ethanone

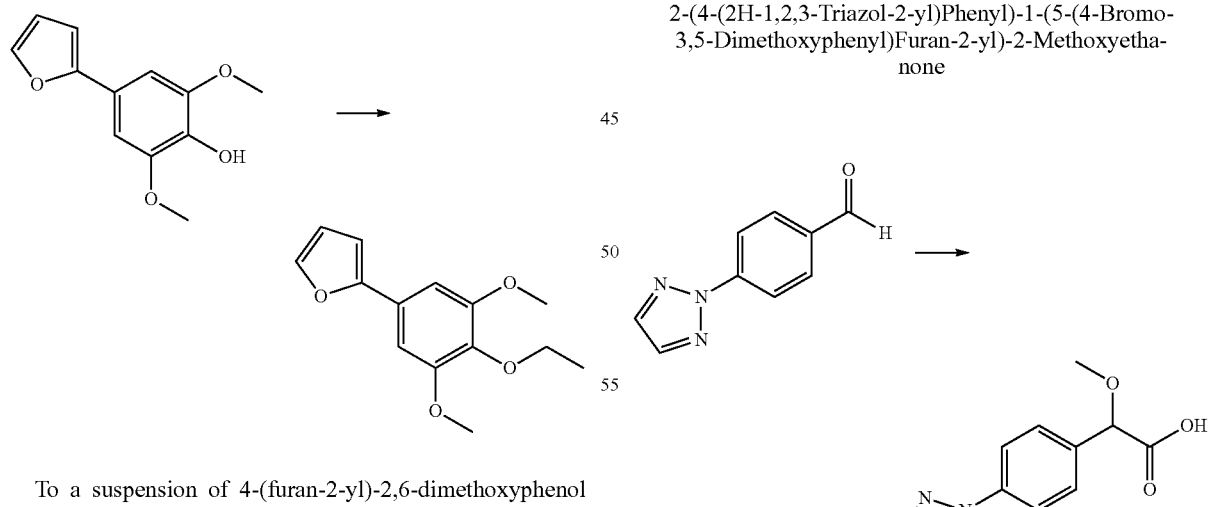

To a suspension of 4-(furan-2-yl)-2,6-dimethoxyphenol (0.493 g, 2.24 mmol) in anhydr DMF (10 mL) under argon was added Cs$_2$CO$_3$ (1.2 g, 3.7 mmol) and iodoethane (0.22 mL, 2.7 mmol). The mixture was stirred for 20 min then heated at 80° C. for 2 hrs. After cooling to room temperature, the reaction was diluted with H$_2$O and EtOAc then it was acidified with the addition of 6 M HCl. The layers were separated and the aqueous layer was extracted with EtOAc. The combined organics were diluted with hexanes and washed with H$_2$O and brine, dried over Na$_2$SO$_4$ and filtered through a pad of silica gel on Celite. The filtrate was concentrated in vacuo to give 2-(4-ethoxy-3,5-dimethoxyphenyl)furan as a beige solid (0.513 g, 92% yield). The product was used without further purification.

29-1

2-(4-Ethoxy-3,5-dimethoxyphenyl)furan was coupled with N,2-dimethoxy-N-methyl-2-(4-morpholinophenyl)acetamide according to the procedure for the synthesis of Example 12. Purification by chromatography (EtOAc-hexanes) gave 1-(5-(4-ethoxy-3,5-dimethoxyphenyl)furan-2-yl)-2-methoxy-2-(4-morpholinophenyl)ethanone as a yellow foam (0.263 g, 58% yield). MS: m/z 482.2 [M+H]$^+$.

Example 30

2-(4-(2H-1,2,3-Triazol-2-yl)Phenyl)-1-(5-(4-Bromo-3,5-Dimethoxyphenyl)Furan-2-yl)-2-Methoxyethanone To a solution of 4-(2H-1,2,3-triazol-2-yl)benzaldehyde (1.0 g, 5.77 mmol) in anhydr MeOH (15 mL) at 0° C. (bath temperature) was added bromoform (1.82 g, 7.21 mmol) with stirring. Solid KOH (1.62 g, 28.9 mmol) was added in aliquots over a period of 10 min. The mixture was stirred for 1 hour and the cold bath was removed. After stirring for 30 min, the reaction was allowed to warm slowly to room temperature overnight then concentrated to dryness. After dissolving in a minimum amount of H₂O, the residue was acidified to pH 1 with 6 M HCl. The aqueous mixture was extracted with EtOAc several times with the addition of brine to the aqueous layer during extraction. The combined organics were washed with brine, dried over Na₂SO₄ and concentrated in vacuo to give 2-(4-(2H-1,2,3-triazol-2-yl)phenyl)-2-methoxyacetic acid as an oil (1.19 g, 88% yield). The product was used without further purification.

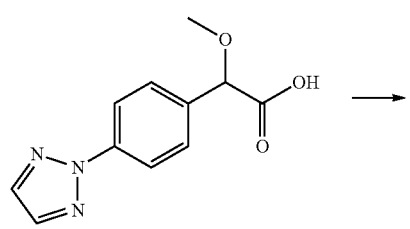

To a solution of 2-(4-(2H-1,2,3-triazol-2-yl)phenyl)-2-methoxyacetic acid (1.19 g, 5.1 mmol in anhydr CH₂Cl₂ (15 ml) was added 4-methylmorpholine (1.55 g, 15.3 mmol) and it was cooled over an ice bath. Isobutylchloroformate (0.84 g, 6.12 mmol) was added and stirred for 45 min. N,O-Dimethylhydroxylamine HCl (0.746 g, 7.65 mmol) was added and the mixture was allowed to stir overnight while warming to room temp. Saturated aqueous NaHCO₃ (15 ml) was added and stirred for 5 min. The organic layer was dried over Na₂SO₄ and evaporated to dryness. Purification by chromatography (100% EtOAc) gave 2-(4-(2H-1,2,3-triazol-2-yl)phenyl)-N,2-dimethoxy-N-methylacetamide as a white solid (0.63 g, 44% yield).

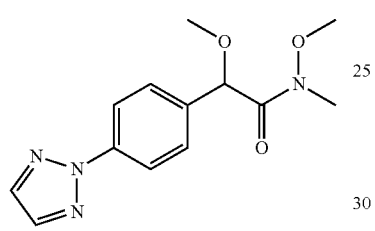

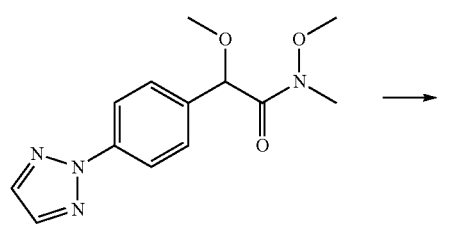

30-1

To a solution of 2-(4-bromo-3,5-dimethoxyphenyl)furan (0.20 g, 0.71 mmol) in anhydr THF (10 mL) under argon in an oven-dried flask cooled to −78° C. was added lithium diisopropylamide (2.0 M in THF/heptane/ethylbenzene; 0.43 mL, 0.85 mmol) dropwise. After stirring for 1 hr at −78° C., a solution of 2-(4-(2H-1,2,3-triazol-2-yl)phenyl)-N,2-dimethoxy-N-methylacetamide (0.195 g, 0.71 mmol) in THF (2 mL) was added dropwise. After stirring for 25 min, the mixture was allowed to warm to room temp while stirring for 2 hrs. The reaction was quenched with the addition of saturated aqueous NH₄Cl and EtOAc was added. The layers were separated and the organic layer was washed with brine, dried over Na₂SO₄ and concentrated in vacuo. Purification by chromatography (30% EtOAc-hexanes) provided 2-(4-(2H-1,2,3-triazol-2-yl)phenyl)-1-(5-(4-bromo-3,5-dimethoxyphenyl)furan-2-yl)-2-methoxyethanone as a yellow solid (0.07 g, 10% yield). MS: m/z 497.9 [M+H]⁺.

Example 31

2-(4-(1H-1,2,3-Triazol-1-yl)Phenyl)-1-(5-(4-Bromo-3,5-Dimethoxyphenyl)Furan-2-yl)-2-Methoxyethanone

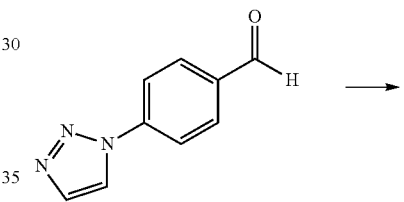

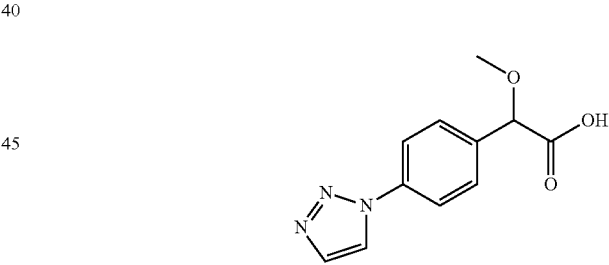

2-(4-(1H-1,2,3-Triazol-1-yl)phenyl)-2-methoxyacetic acid was prepared from 4-(1H-1,2,3-triazol-1-yl)benzaldehyde according to the procedure used in Example 30. The product was obtained as an oil and used without further purification (1.02 g, 76% yield).

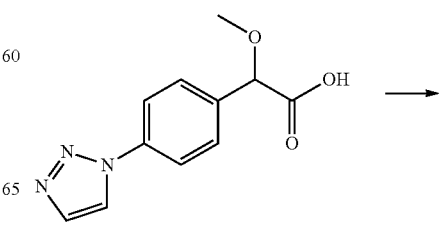

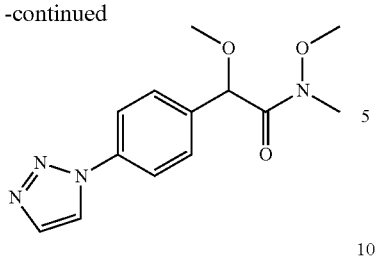

2-(4-(1H-1,2,3-Triazol-1-yl)phenyl)-N,2-dimethoxy-N-methylacetamide was prepared from 2-(4-(1H-1,2,3-triazol-1-yl)phenyl)-2-methoxyacetic acid according to the procedure used in Example 30. Purification by chromatography (60% EtOAc/hexanes) gave of the product as an oil (0.73 g, 58% yield).

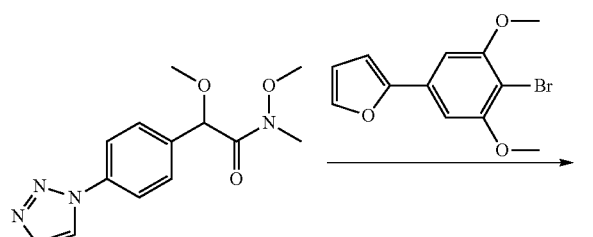

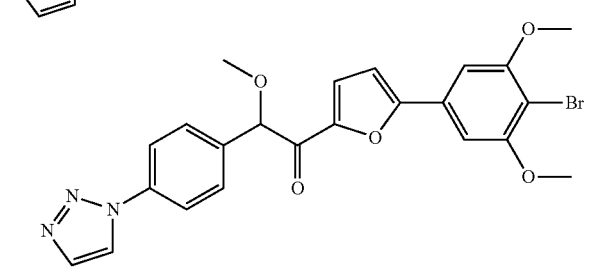

31-1

2-(4-(1H-1,2,3-Triazol-1-yl)phenyl)-1-(5-(4-bromo-3,5-dimethoxyphenyl)furan-2-yl)-2-methoxyethanone was prepared from 2-(4-bromo-3,5-dimethoxyphenyl)furan and 2-(4-(1H-1,2,3-triazol-1-yl)phenyl)-N,2-dimethoxy-N-methylacetamide according to the procedure used in Example 30. Purification by chromatography (50% EtOAc/hexanes) gave 2-(4-(1H-1,2,3-triazol-1-yl)phenyl)-1-(5-(4-bromo-3,5-dimethoxyphenyl)furan-2-yl)-2-methoxyethanone as a yellow solid (0.025 g, 7% yield). MS: m/z 498.2 [M+H]⁺.

Example 32

2-(4-(1H-1,2,4-Triazol-1-yl)Phenyl)-1-(5-(4-Bromo-3,5-Dimethoxyphenyl)Furan-2-yl)-2-Methoxyethanone

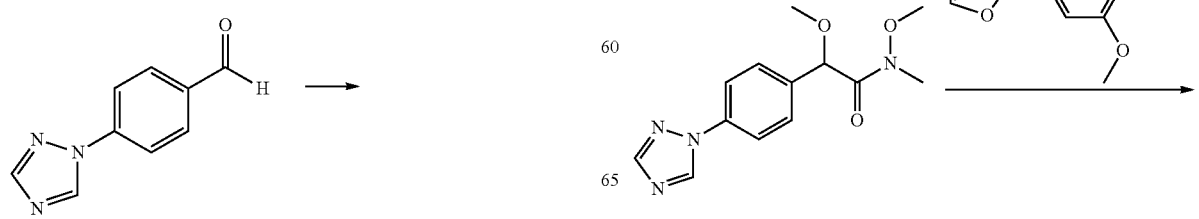

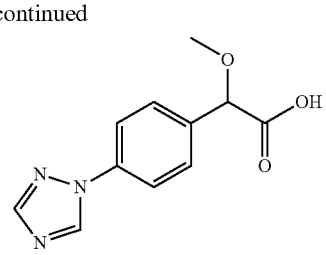

2-(4-(1H-1,2,4-Triazol-1-yl)phenyl)-2-methoxyacetic acid was prepared from 4-(1H-1,2,4-triazol-1-yl)benzaldehyde according to the procedure used in Example 30. The crude product was obtained as a white solid and used without further purification (1.9 g, 47% yield).

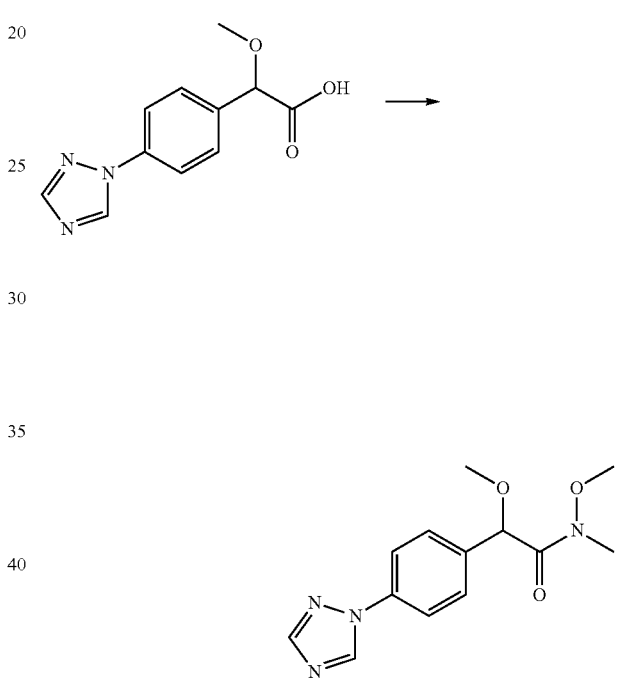

2-(4-(1H-1,2,4-Triazol-1-yl)phenyl)-N,2-dimethoxy-N-methylacetamide was prepared from 2-(4-(1H-1,2,4-triazol-1-yl)phenyl)-2-methoxyacetic acid according to the procedure used in Example 30. Purification by chromatography (100% EtOAc) gave the product as an off-white solid (0.30 g, 26% yield).

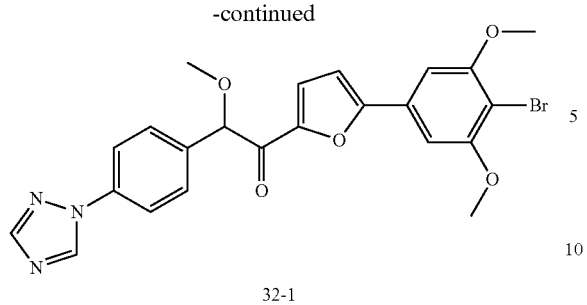

32-1

2-(4-(1H-1,2,4-Triazol-1-yl)phenyl)-1-(5-(4-bromo-3,5-dimethoxyphenyl)furan-2-yl)-2-methoxyethanone was prepared from 2-(4-bromo-3,5-dimethoxyphenyl)furan and 2-(4-(1H-1,2,4-triazol-1-yl)phenyl)-N,2-dimethoxy-N-methylacetamide according to the procedure used in Example 30. Purification by chromatography (60% EtOAc-hexanes) followed by another purification (40% acetone-hexanes) gave 2-(4-(1H-1,2,4-triazol-1-yl)phenyl)-1-(5-(4-bromo-3,5-dimethoxyphenyl)furan-2-yl)-2-methoxyethanone as a pale yellow solid (0.078 g, 11% yield). MS: m/z 498.2 [M+1-1]$^+$.

Example 33

1-(5-(4-Bromo-3,5-Dimethoxyphenyl)Furan-2-yl)-2-Methoxy-2-(4-(2-Methyl-2H-Tetrazol-5-yl)Phenyl)Ethanone

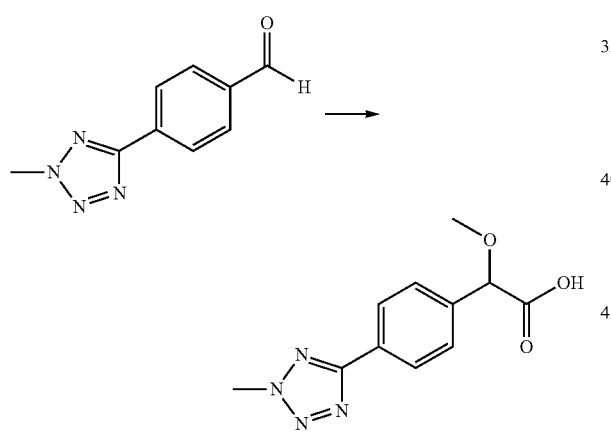

2-Methoxy-2-(4-(2-methyl-2H-tetrazol-5-yl)phenyl)acetic acid was prepared from 4-(2-methyl-2H-tetrazol-5-yl)benzaldehyde according to the procedure used in Example 30. The crude product was obtained as an oil and used without further purification (0.88 g, 86% yield).

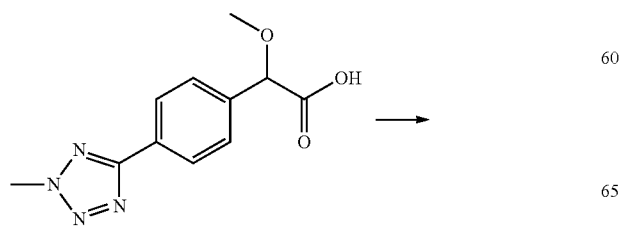

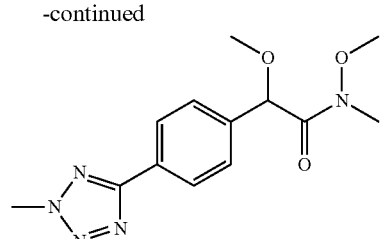

To a solution of 2-methoxy-2-(4-(2-methyl-2H-tetrazol-5-yl)phenyl)acetic acid (0.87 g, 3.5 mmol) in anhydr CH$_2$Cl$_2$ (10 ml) was added N,N-diisopropylethylamine (1.36 g, 10.5 mmol) while cooling over an ice bath. bis(2-Methoxyethyl)aminosulfur trifluoride (0.93 g, 4.2 mmol) was added and stirred 15 min. N,O-Dimethylhydroxylamine HCl (0.512 g, 5.25 mmol) was added and the mixture was allowed to stir overnight while warming to room temp. Saturated aqueous NaHCO$_3$ (15 ml) was added and stirred for 5 min. The organic layer was dried over Na$_2$SO$_4$ and evaporated to dryness. Purification by chromatography (60% EtOAc-hexanes) gave N,2-dimethoxy-N-methyl-2-(4-(2-methyl-2H-tetrazol-5-yl)phenyl)acetamide as a clear oil (0.425 g, 42% yield).

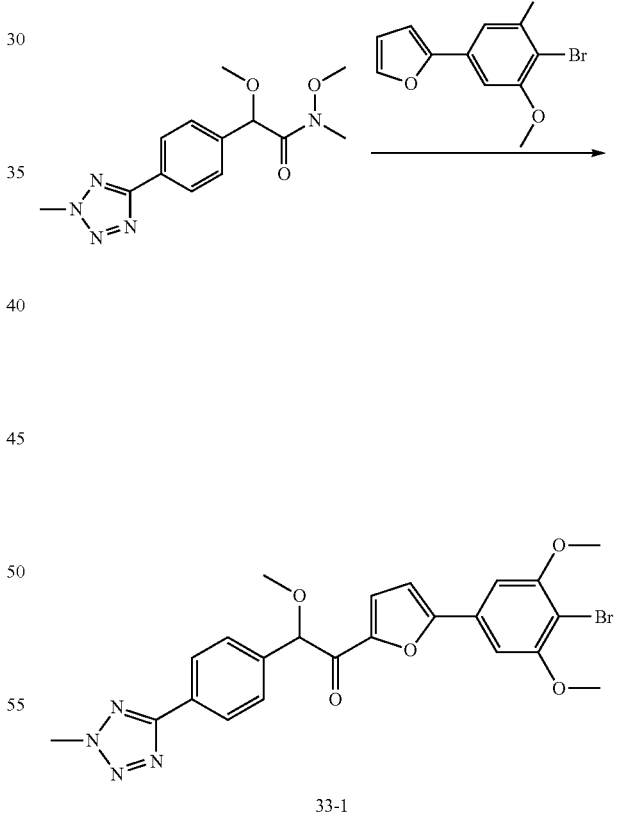

33-1

1-(5-(4-Bromo-3,5-dimethoxyphenyl)furan-2-yl)-2-methoxy-2-(4-(2-methyl-2H-tetrazol-5-yl)phenyl)ethanone was prepared from 2-(4-bromo-3,5-dimethoxyphenyl)furan and N,2-dimethoxy-N-methyl-2-(4-(2-methyl-2H-tetrazol-5-yl)phenyl)acetamide according to the procedure used in Example 30. Purification by chromatography (40% EtOAc/ hexanes) gave the product as a pale yellow solid (0.106 g, 29% yield). MS: m/z 513.3 [M+H]⁺.

Example 34

1-(5-(4-Bromo-3,5-Dimethoxyphenyl)Furan-2-yl)-2-Methoxy-2-(4-(5-Methyl-1,3,4-Thiadiazol-2-yl)Phenyl)Ethanone

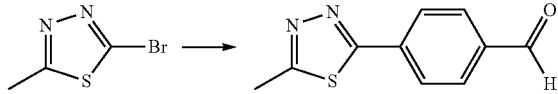

To a solution of 2-bromo-5-methyl-1,3,4-thiadiazole (2.0 g, 11.17 mmol) in dioxane (40 ml) was added 4-formylbenzeneboronic acid (3.35 g, 22.34 mmol) and 2M Na₂CO₃ (23 ml). This mixture was degassed with a stream of argon for 2 min. Tetrakis(triphenylphosphine)palladium (0.636 g, 0.55 mmol) was added and this mixture was heated at reflux overnight under argon. After cooling to room temperature, H₂O (30 ml) and EtOAc (50 ml) were added and stirred for 5 min. The organic layer was separated and washed with brine, dried over Na₂SO₄ and concentrated in vacuo. Purification by chromatography (10 to 20% EtOAc/hexanes) gave 4-(5-methyl-1,3,4-thiadiazol-2-yl)benzaldehyde as a pale yellow liquid (1.16 g, 51% yield).

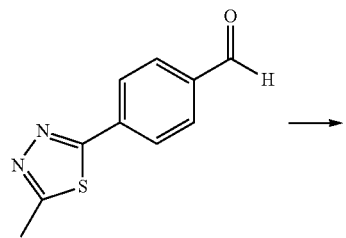

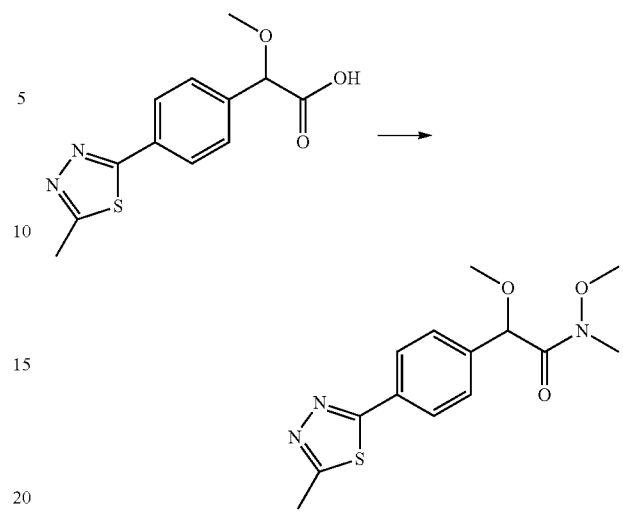

N,2-Dimethoxy-N-methyl-2-(4-(5-methyl-1,3,4-thiadiazol-2-yl)phenyl)acetamide was prepared from 2-methoxy-2-(4-(5-methyl-1,3,4-thiadiazol-2-yl)phenyl)acetic acid according to the procedure used in Example 33. Purification by chromatography (100% EtOAc) gave the product as a pale yellow oil (0.177 g, 26% yield).

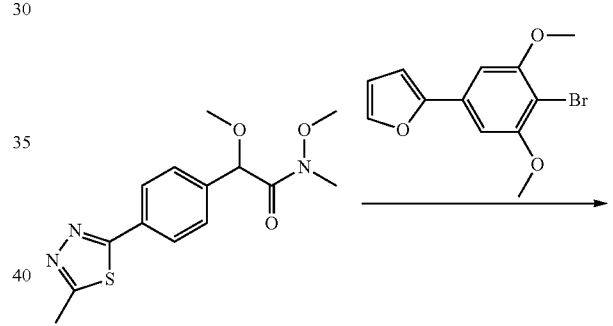

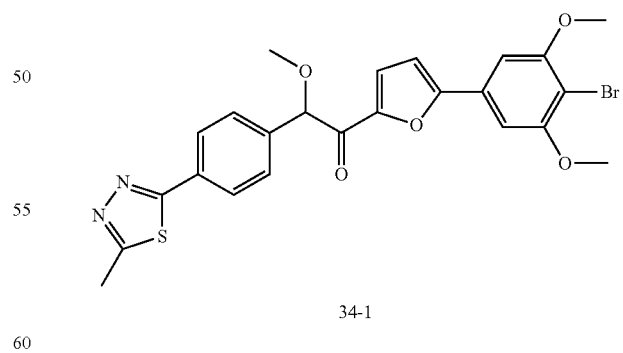

34-1

2-Methoxy-2-(4-(5-methyl-1,3,4-thiadiazol-2-yl)phenyl)acetic acid was prepared from 4-(5-methyl-1,3,4-thiadiazol-2-yl)benzaldehyde according to the procedure used in Example 30. The crude product was obtained as an oil and used without further purification (1.12 g, 75% yield).

1-(5-(4-Bromo-3,5-dimethoxyphenyl)furan-2-yl)-2-methoxy-2-(4-(5-methyl-1,3,4-thiadiazol-2-yl)phenyl)ethanone was prepared from 2-(4-bromo-3,5-dimethoxyphenyl)furan and N,2-dimethoxy-N-methyl-2-(4-(5-methyl-1,3,4-thiadiazol-2-yl)phenyl)acetamide according to the procedure used in Example 30. Purification by chromatography (70%

EtOAc/hexanes) gave the product as a pale yellow solid (0.044 g, 15% yield). MS: m/z 529.3 [M+H]+.

Example 35

1-(5-(4-Bromo-3,5-Dimethoxyphenyl)Furan-2-yl)-2-Methoxy-2-(4-(2-Methylthiazol-4-yl)Phenyl)Ethanone

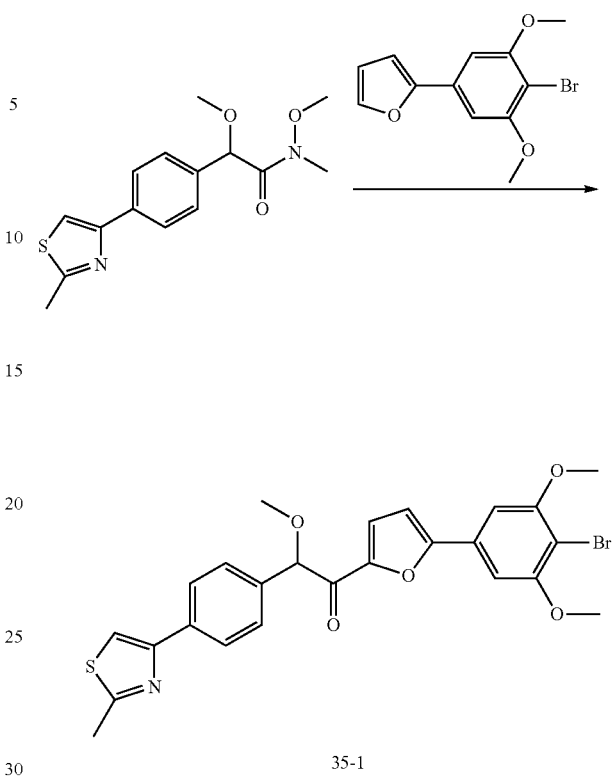

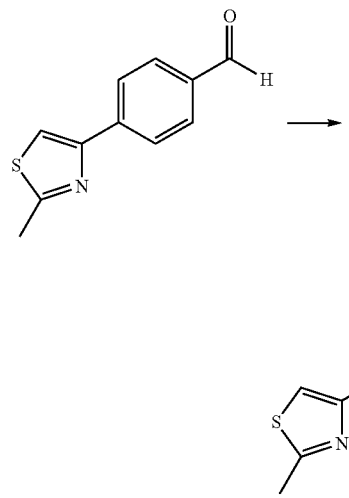

2-Methoxy-2-(4-(2-methylthiazol-4-yl)phenyl)acetic acid was prepared from 4-(2-methylthiazol-4-yl)benzaldehyde according to the procedure used in Example 30. The crude product was obtained as an oil and used without further purification (0.972 g, 78% yield).

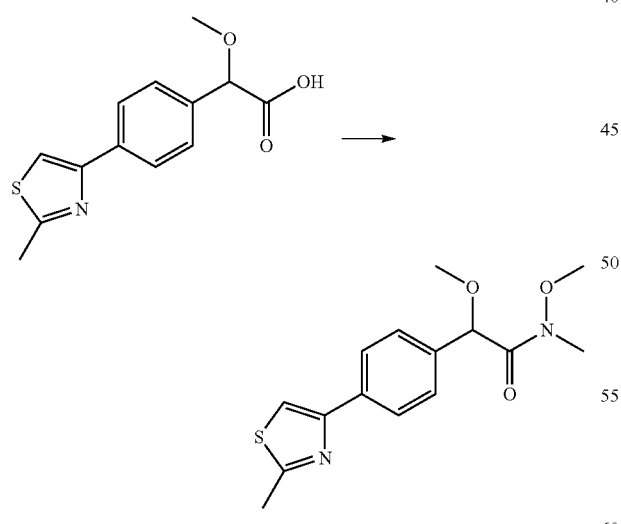

N,2-Dimethoxy-N-methyl-2-(4-(2-methylthiazol-4-yl)phenyl)acetamide was prepared from 2-methoxy-2-(4-(2-methylthiazol-4-yl)phenyl)acetic acid according to the procedure used in Example 33. Purification by chromatography (70% EtOAc/hexanes) gave the product as an oil (0.516 g, 46% yield).

1-(5-(4-Bromo-3,5-dimethoxyphenyl)furan-2-yl)-2-methoxy-2-(4-(2-methylthiazol-4-yl)phenyl)ethanone was prepared from 2-(4-bromo-3,5-dimethoxyphenyl)furan and N,2-dimethoxy-N-methyl-2-(4-(2-methylthiazol-4-yl)phenyl)acetamide according to the procedure used in Example 30. Purification by chromatography (60% EtOAc/hexanes) gave the product as a offwhite solid (0.039 g, 10% yield). MS: m/z 528.2 [M+H]+.

Example 36

2-Methoxy-2-(4-(5-Methyl-1,3,4-Oxadiazol-2-yl)Phenyl)-1-(5-(3,4,5-Trimethoxyphenyl)Furan-2-yl)Ethanone

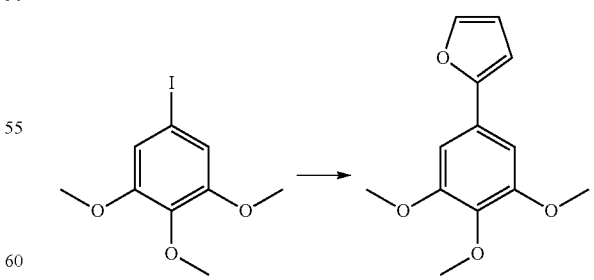

2-(3,4,5-Trimethoxyphenyl)furan was prepared from 5-iodo-1,2,3-trimethoxybenzene according to the procedure used in Example 12. Purification by chromatography (10% EtOAc/hexanes) gave the product as an off white solid (1.2 g, 60% yield).

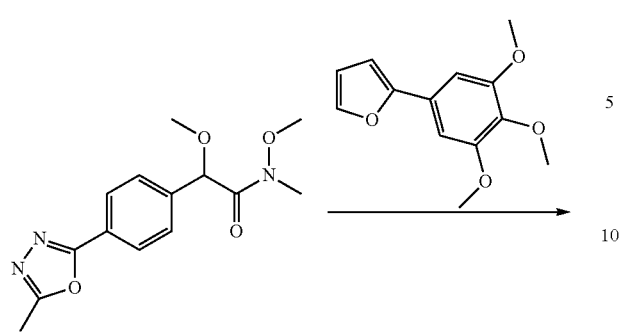
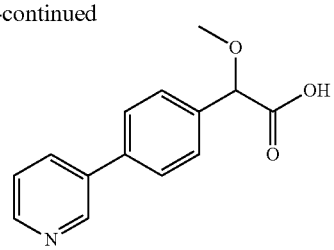

2-Methoxy-2-(4-(pyridin-3-yl)phenyl)acetic acid was prepared from 4-(pyridin-3-yl)benzaldehyde according to the procedure used in Example 30 except pH 4 was used during the extractive work-up. The crude product was obtained as an oil and used without further purification (0.415 g, 33% yield).

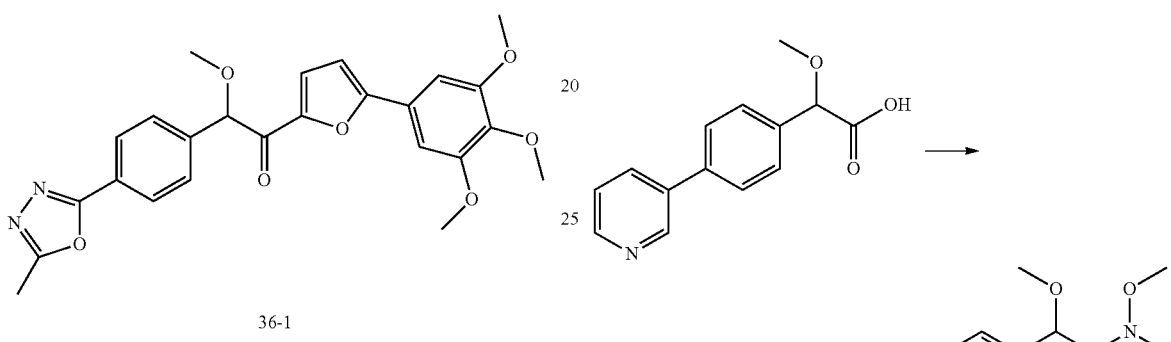

To a solution of 2-(3,4,5-trimethoxyphenyl)furan (1.4 g, 5.98 mmol) in anhydr THF (70 mL) under argon in an oven-dried flask cooled to −78° C. was added n-butyl lithium (2.5 M in hexanes; 2.63 mL, 6.28 mmol) dropwise. After stirring for 1 hr at −78° C., a solution of N,2-dimethoxy-N-methyl-2-(4-(5-methyl-1,3,4-oxadiazol-2-yl)phenyl)acetamide (1.75 g, 6.0 mmol) in THF (5 mL) was added dropwise. After stirring for 25 min, the mixture was allowed to warm to room temp while stirring for 2 hrs. The reaction was quenched with the addition of saturated aqueous NH₄Cl then brine and EtOAc were added. The layers were separated and the organic layer was washed with brine, dried over Na₂SO₄ and concentrated in vacuo. Purification by column chromatography (60% EtOAc-hexanes) gave 2-methoxy-2-(4-(5-methyl-1,3,4-oxadiazol-2-yl)phenyl)-1-(5-(3,4,5-trimethoxyphenyl)furan-2-yl)ethanone as a fluffy yellow solid (0.81 g, 29% yield). MS: m/z 465.3 [M+H]⁺.

Example 37

1-(5-(4-Bromo-3,5-Dimethoxyphenyl)Furan-2-yl)-2-Methoxy-2-(4-(Pyridin-3-yl)Phenyl)Ethanone

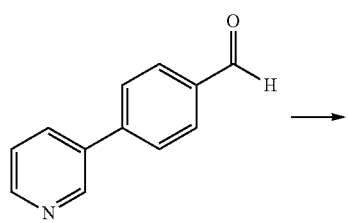

N,2-Dimethoxy-N-methyl-2-(4-(pyridin-3-yl)phenyl)acetamide was prepared from 2-methoxy-2-(4-(pyridin-3-yl)phenyl)acetic acid according to the procedure used in Example 33. Purification by chromatography (100% EtOAc) gave the product as an oil (0.232 g, 48% yield).

1-(5-(4-Bromo-3,5-dimethoxyphenyl)furan-2-yl)-2-methoxy-2-(4-(pyridin-3-yl)phenyl)ethanone was prepared from 2-(4-bromo-3,5-dimethoxyphenyl)furan and N,2-dimethoxy-N-methyl-2-(4-(pyridin-3-yl)phenyl)acetamide according to the procedure used in Example 30. Purification by chromatography (50% EtOAc/hexanes) gave the product as an off white solid (0.126 g, 35% yield). MS: m/z 508.2 [M+H]+.

Example 38

1-(5-(4-Bromo-3,5-Dimethoxyphenyl)Furan-2-yl)-2-Ethoxy-2-(4-Morpholinophenyl)Ethanone

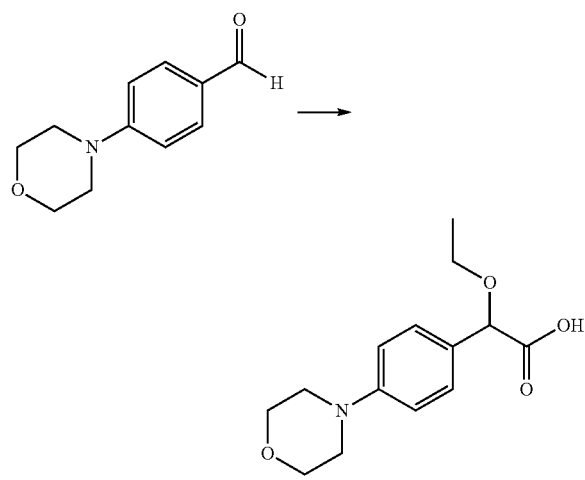

2-Ethoxy-2-(4-morpholinophenyl)acetic acid was synthesized from 4-morpholinobenzaldehyde according to the procedure used for the synthesis of Example 1 except that EtOH was used as the solvent. The product was isolated as a pale red oil and used without further purification.

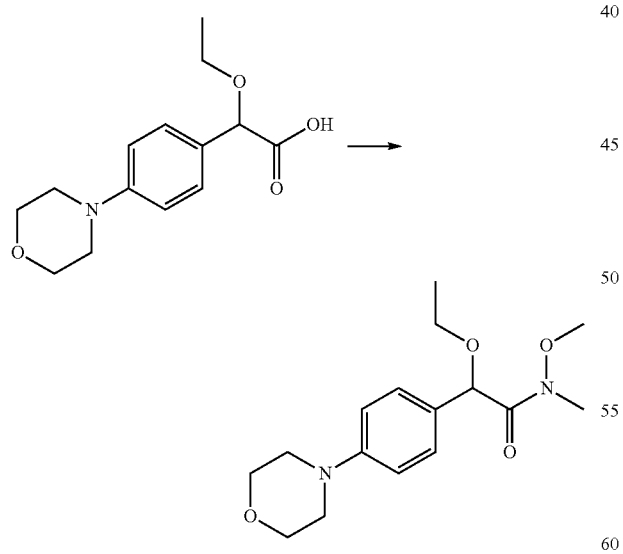

2-Ethoxy-N-methoxy-N-methyl-2-(4-morpholinophenyl) acetamide was synthesized from 2-ethoxy-2-(4-morpholinophenyl)acetic acid following the procedure used for Example 13. Purification by chromatography (EtOAc-hexanes) provided the product as a yellow solid (1.0 g, 31% yield for two steps).

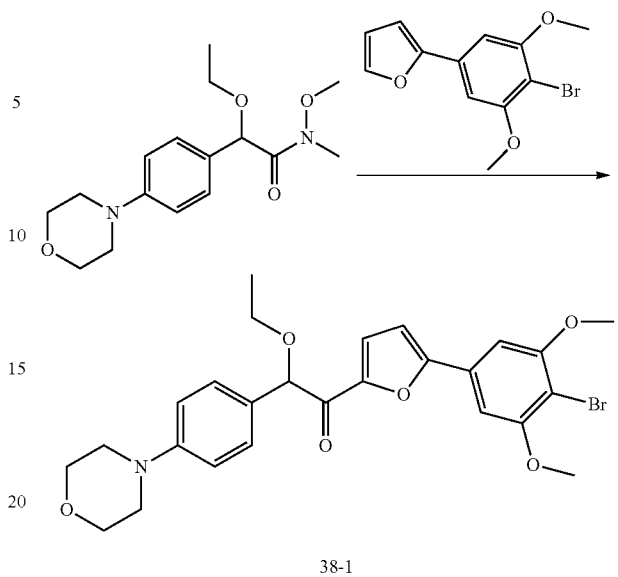

38-1

1-(5-(4-Bromo-3,5-dimethoxyphenyl)furan-2-yl)-2-ethoxy-2-(4-morpholinophenyl)ethanone was prepared from 2-(4-bromo-3,5-dimethoxyphenyl)furan and 2-ethoxy-N-methoxy-N-methyl-2-(4-morpholinophenyl)acetamide according to the procedure used in Example 30. Purification by chromatography (50% EtOAc/hexanes) gave the product as a yellow solid (0.129 g, 34% yield). MS: m/z 530.2 [M+H]+.

Example 39

1-(5-(3-Bromo-4,5-Dimethoxyphenyl)Furan-2-yl)-2-Methoxy-2-(4-(5-Methyl-1,3,4-Oxadiazol-2-yl)Phenyl)Ethanone

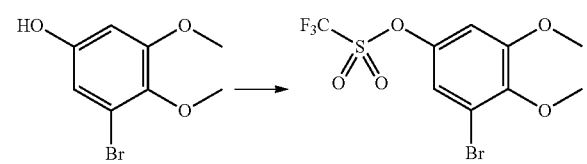 [SMILES: COc1cc(O)cc(Br)c1OC ; COc1cc(OS(=O)(=O)C(F)(F)F)cc(Br)c1OC]

3-Bromo-4,5-dimethoxyphenol was prepared from 3-bromo-4,5-dimethoxybenzaldehyde according to the procedure used in Example 21. Crystallization from ether/hexanes gave the product as a white solid (2.02 g, 39% yield).

3-Bromo-4,5-dimethoxyphenyl trifluoromethanesulfonate was prepared from 3-bromo-4,5-dimethoxyphenol according to the procedure used in Example 21. Evaporation to dryness gave the product as a pale yellow oil (3.3 g, 100% yield).

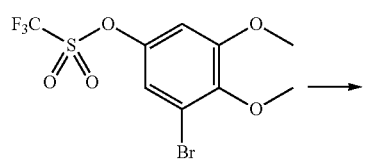

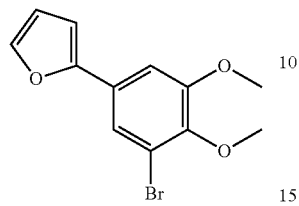

2-(3-Bromo-4,5-dimethoxyphenyl)furan was prepared from 3-bromo-4,5-dimethoxyphenyl trifluoromethanesulfonate according to the procedure used in Example 21. Purification by chromatography (10% ether/hexanes) gave the product as a pale yellow oil (1.7 g, 73% yield).

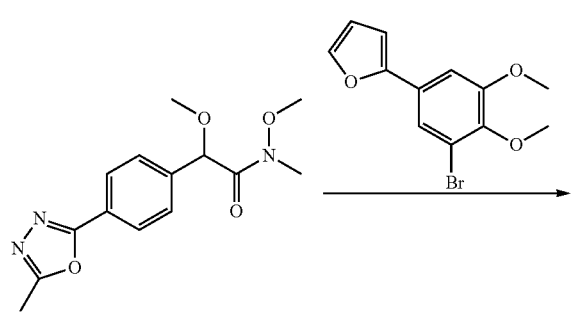

39-1

1-(5-(3-Bromo-4,5-dimethoxyphenyl)furan-2-yl)-2-methoxy-2-(4-(5-methyl-1,3,4-oxadiazol-2-yl)phenyl)ethanone was prepared from 2-(3-bromo-4,5-dimethoxyphenyl)furan and N,2-dimethoxy-N-methyl-2-(4-(5-methyl-1,3,4-oxadiazol-2-yl)phenyl)acetamide according to the procedure used in Example 30. Purification by chromatography (70% EtOAc/hexanes) gave the product as a pale yellow solid (0.037 g, 10% yield). MS: m/z 513.1 [M+H]+.

Example 40

1-(5-(3-Chloro-4,5-Dimethoxyphenyl)Furan-2-yl)-2-Methoxy-2-(4-(5-Methyl-1,3,4-Oxadiazol-2-yl)Phenyl)Ethanone

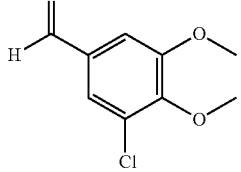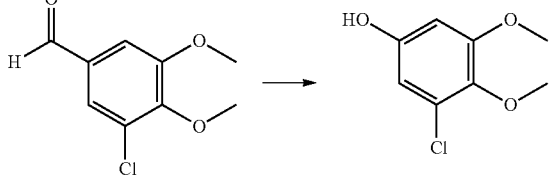

3-Chloro-4,5-dimethoxyphenol was synthesized from 3-chloro-4,5-dimethoxybenzaldehyde according to the procedure used for the synthesis of Example 21. The crude solid obtained was digested with ~10% EtOAc-hexanes at 40° C. for 1 hr. After cooling to room temperature, the solid was collected on a Büchner and dried in vacuo to give a crystalline beige solid (1.44 g, 38% yield for two steps).

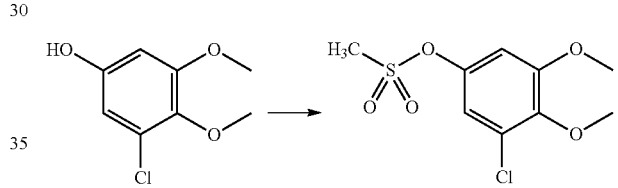

3-Chloro-4,5-dimethoxyphenyl trifluoromethanesulfonate was synthesized from 3-chloro-4,5-dimethoxyphenol according to the procedure for the synthesis of Example 21. The product was isolated as a pale yellow liquid and used in the next synthetic step without further purification (2.33 g, 96% yield).

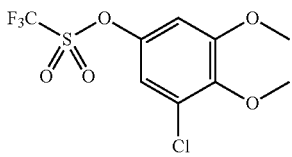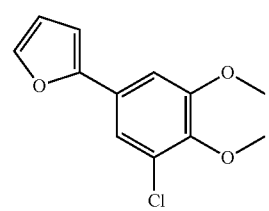

2-(3-Chloro-4,5-dimethoxyphenyl)furan was synthesized from 3-chloro-4,5-dimethoxyphenyl trifluoromethanesulfonate according to the procedure used in the synthesis of Example 21. Purification by chromatography (10% Et₂O-hexanes) gave the product as a pale yellow oil (1.6 g, 94% yield).

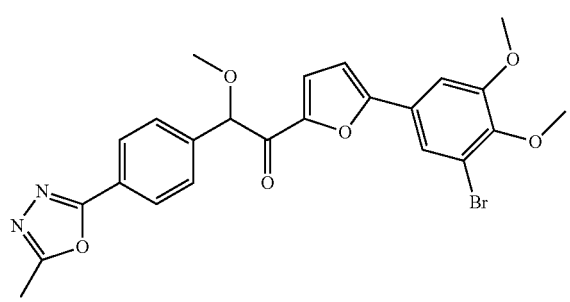

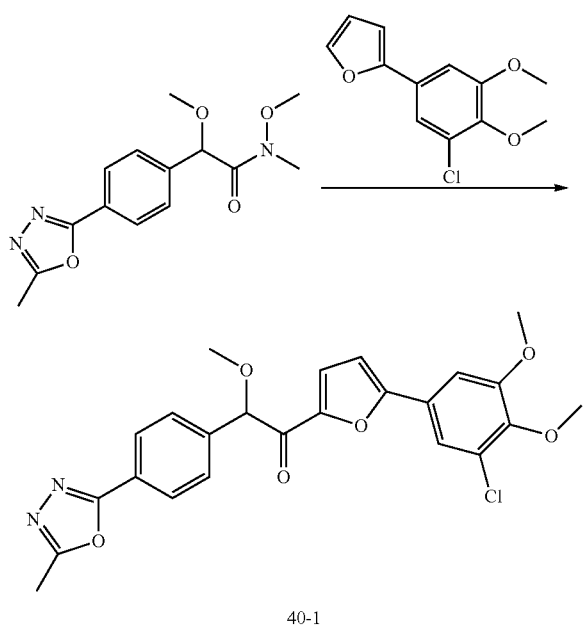

40-1

1-(5-(3-Chloro-4,5-dimethoxyphenyl)furan-2-yl)-2-methoxy-2-(4-(5-methyl-1,3,4-oxadiazol-2-yl)phenyl)ethanone was prepared from 2-(3-chloro-4,5-dimethoxyphenyl)furan and N,2-dimethoxy-N-methyl-2-(4-(5-methyl-1,3,4-oxadiazol-2-yl)phenyl)acetamide according to the procedure used in Example 30. Purification by chromatography (70% EtOAc/hexanes) gave the product as a pale yellow solid (0.051 g, 12% yield). MS: m/z 469.2 [M+H]⁺.

Example 41

1-(5-(4-Bromo-3,5-Dimethoxyphenyl)Furan-2-yl)-2-(Cyclopropylmethoxy)-2-(4-Morpholinophenyl) Ethanone

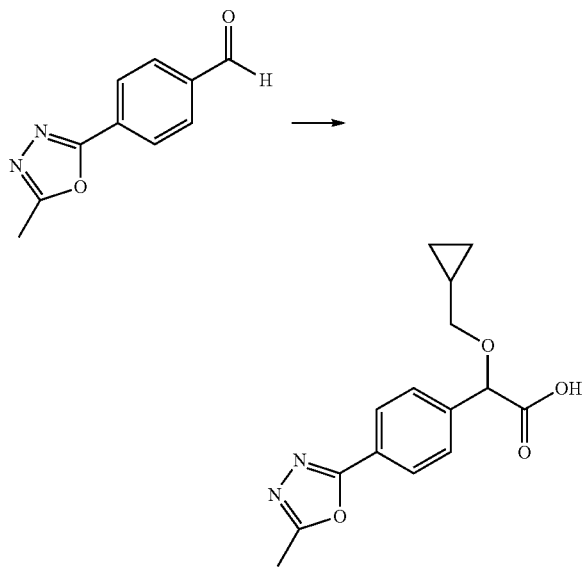 [SMILES: Cc1nnc(-c2ccc(C=O)cc2)o1 ; CCOC(C(=O)O)c1ccc(-c2nnc(C)o2)cc1]

To a solution of 4-(5-methyl-1,3,4-oxadiazol-2-yl)benzaldehyde (5.3 g, 27.7 mmol) in cyclopropylmethanol (25 mL) and anhydrous dioxane (25 mL) at 0° C. (bath temperature) was added several drops of a solution of KOH (7.77 g, 138.5 mmol) in cyclopropylmethanol (35 mL). Bromoform (3.1 mL, 35.2 mmol) was added, then the remaining KOH/cyclopropylmethanol solution was added over a period of 20 min. After stirring for 30 min, the reaction mixture was allowed to warm slowly to room temperature overnight then concentrated to dryness. After dissolving in a minimum amount of H₂O, the residue was acidified to pH 1 with concentrated HCl. The aqueous mixture was extracted with EtOAc several times with the addition of brine to the aqueous layer during extraction. The combined organics were washed with brine, dried over Na₂SO₄ and concentrated in vacuo to give 2-(cyclopropylmethoxy)-2-(4-(5-methyl-1,3,4-oxadiazol-2-yl)phenyl) acetic acid as a semisolid which was then recyrstallized from Et₂O (0.5 g, 7% yield).

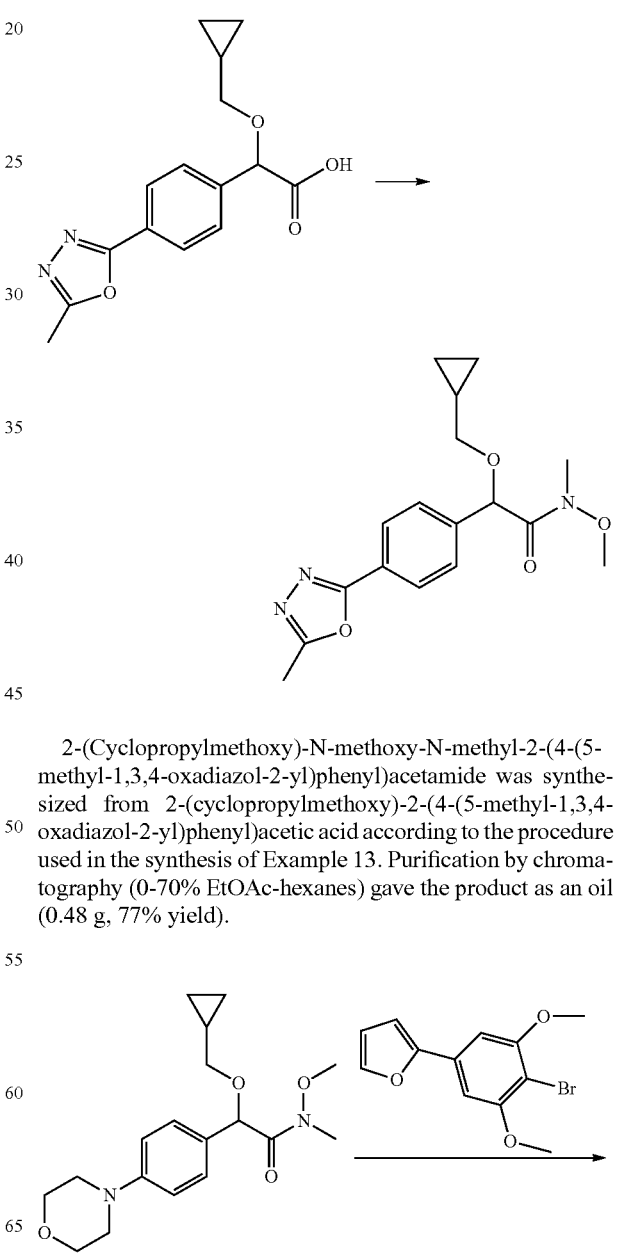

2-(Cyclopropylmethoxy)-N-methoxy-N-methyl-2-(4-(5-methyl-1,3,4-oxadiazol-2-yl)phenyl)acetamide was synthesized from 2-(cyclopropylmethoxy)-2-(4-(5-methyl-1,3,4-oxadiazol-2-yl)phenyl)acetic acid according to the procedure used in the synthesis of Example 13. Purification by chromatography (0-70% EtOAc-hexanes) gave the product as an oil (0.48 g, 77% yield).

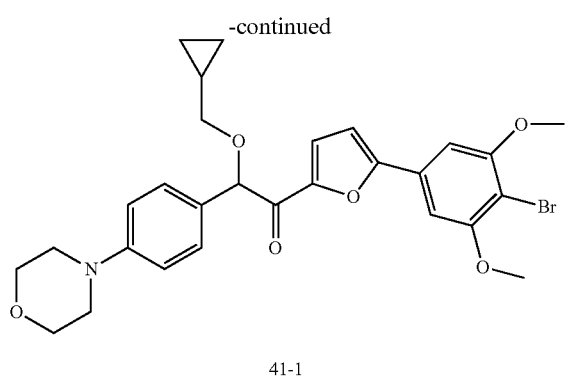

41-1

1-(5-(4-Bromo-3,5-dimethoxyphenyl)furan-2-yl)-2-(cyclopropylmethoxy)-2-(4-morpholinophenyl)ethanone was prepared from 2-(4-bromo-3,5-dimethoxyphenyl)furan and 2-(cyclopropylmethoxy)-N-methoxy-N-methyl-2-(4-morpholinophenyl)acetamide according to the procedure used in Example 30. Purification by chromatography (40% EtOAc/hexanes) gave the product as a pale yellow solid (0.092 g, 23% yield). MS: m/z 556.3 [M+H]+.

Example 42

1-(5-(4-Bromo-3,5-Dimethoxyphenyl)Furan-2-yl)-2-Methoxy-2-(6-Methoxypyridin-3-yl)Ethanone

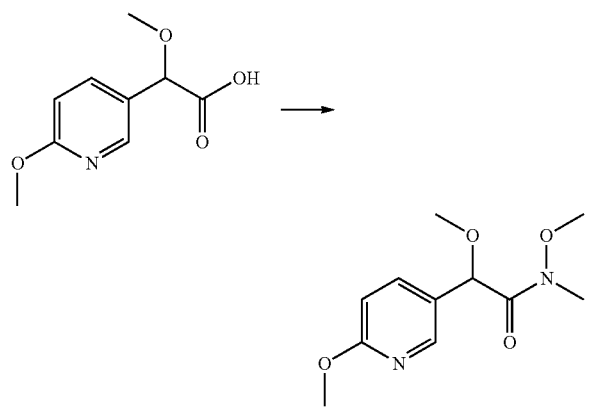

2-Methoxy-2-(6-methoxypyridin-3-yl)acetic acid was prepared from 6-methoxynicotinaldehyde according to the procedure used in Example 37. The crude product was obtained as an oil and used without further purification (5.67 g, 79% yield).

N,2-Dimethoxy-2-(6-methoxypyridin-3-yl)-N-methylacetamide was prepared from 2-methoxy-2-(6-methoxypyridin-3-yl)acetic acid according to the procedure used in Example 33. Purification by chromatography (60% EtOAc/hexanes) gave the product as an oil (0.97 g, 40% yield).

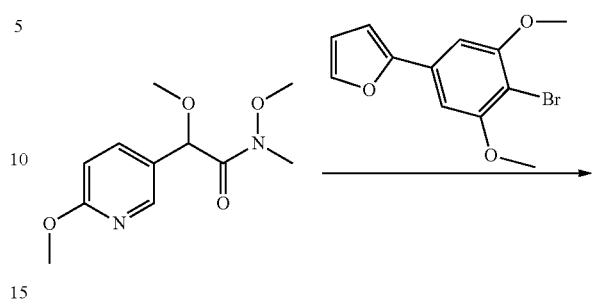

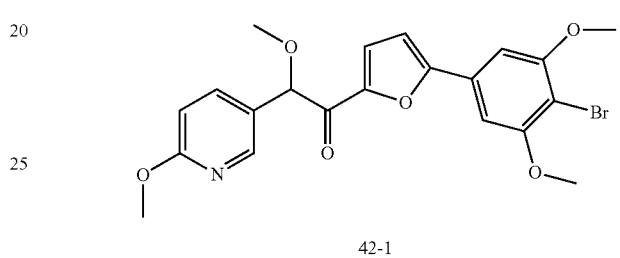

42-1

1-(5-(4-Bromo-3,5-dimethoxyphenyl)furan-2-yl)-2-methoxy-2-(6-methoxypyridin-3-yl)ethanone was prepared from 2-(4-bromo-3,5-dimethoxyphenyl)furan and N,2-dimethoxy-2-(6-methoxypyridin-3-yl)-N-methylacetamide according to the procedure used in Example 30. Purification by chromatography (50% EtOAc/hexanes) gave the product as a pale yellow solid (0.092 g, 28% yield). MS: m/z 462.2 [M+H]+.

Example 43

1-(5-(4-Bromo-3,5-Dimethoxyphenyl)Furan-2-yl)-2-(4-((Dimethylamino)Methyl)Phenyl)-2-Methoxyethanone 2-(4-((Dimethylamino)methyl)phenyl)-2-methoxyacetic acid was prepared from 4-((dimethylamino)methyl)benzaldehyde according to the procedure used in Example 37. After the pH was adjusted to 4 the aqueous solution was evaporated to dryness. MeOH (20 ml) was added with swirling and the material was filtered. Evaporation to dryness gave the crude product that was used without further purification (1.3 g, 95% yield).

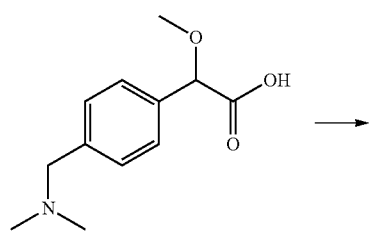

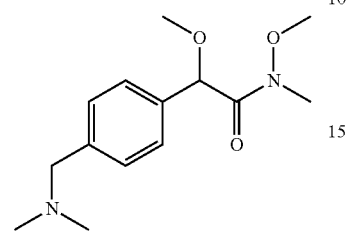

2-(4-((Dimethylamino)methyl)phenyl)-N,2-dimethoxy-N-methylacetamide was prepared from 2-(4-((dimethylamino)methyl)phenyl)-2-methoxyacetic acid according to the procedure used in Example 33. Purification by chromatography (100% EtOAc) gave the product as an oil (0.212 g, 14% yield).

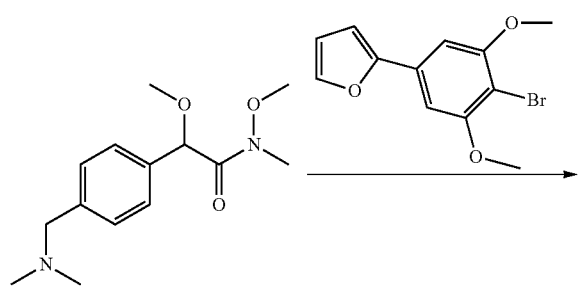

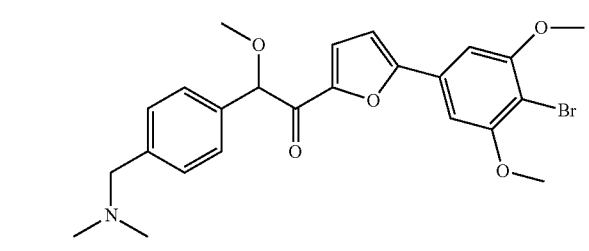

43-1

1-(5-(4-Bromo-3,5-dimethoxyphenyl)furan-2-yl)-2-(4-((dimethylamino)methyl)phenyl)-2-methoxyethanone was prepared from 2-(4-bromo-3,5-dimethoxyphenyl)furan and 2-(4-((dimethylamino)methyl)phenyl)-N,2-dimethoxy-N-methylacetamide according to the procedure used in Example 30. Purification by chromatography (4% MeOH/CH$_2$Cl$_2$) gave the product as a pale yellow oil (0.004 g, 1% yield). MS: m/z 488.3 [M+H]$^+$.

Example 44

1-(5-(4-Bromo-3,5-Dimethoxyphenyl)Furan-2-yl)-2-Methoxy-2-(6-Morpholinopyridin-3-yl)Ethanone 2-Methoxy-2-(6-morpholinopyridin-3-yl)acetic acid was prepared from 6-morpholinonicotinaldehyde according to the procedure used in Example 30 except the aqueous mixture was adjusted to pH 4 during the extractive work-up. The crude product was obtained as an oil and used without further purification (1.17 g, 89% yield).

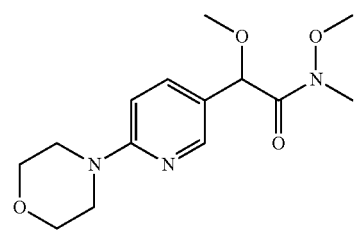

N,2-Dimethoxy-N-methyl-2-(6-morpholinopyridin-3-yl)acetamide was prepared from 2-methoxy-2-(6-morpholinopyridin-3-yl)acetic acid according to the procedure used in Example 33. Purification by chromatography (80% EtOAc/hexanes) gave the product as an oil (0.692 g, 51% yield).

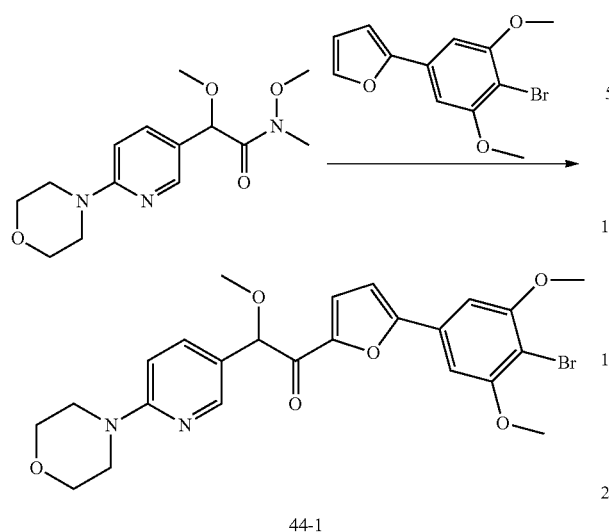

44-1

1-(5-(4-Bromo-3,5-dimethoxyphenyl)furan-2-yl)-2-methoxy-2-(6-morpholinopyridin-3-yl)ethanone was prepared from 2-(4-bromo-3,5-dimethoxyphenyl)furan and N,2-dimethoxy-N-methyl-2-(6-morpholinopyridin-3-yl)acetamide according to the procedure used in Example 30. Purification by chromatography (60% EtOAc/hexanes) gave the product as a pale yellow solid (0.04 g, 11% yield). MS: m/z 517.3 [M+H]$^+$.

Example 45

1-(5-(4-Bromo-3,5-Dimethoxyphenyl)Furan-2-yl)-2-Methoxy-2-(4-(Pyrazin-2-yl)Phenyl)Ethanone 2-Methoxy-2-(4-(pyrazin-2-yl)phenyl)acetic acid was prepared from 4-(pyrazin-2-yl)benzaldehyde according to the procedure used in Example 30 except the aqueous mixture was adjusted to pH 4 during the extractive work-up. The crude product was obtained as an oil and was used without further purification (1.21 g, 91% yield).

N,2-Dimethoxy-N-methyl-2-(4-(pyrazin-2-yl)phenyl)acetamide was prepared from 2-methoxy-2-(4-(pyrazin-2-yl)phenyl)acetic acid according to the procedure used in Example 33. Purification by chromatography (80% EtOAc/hexanes) gave the product as an oil (0.493 g, 35% yield).

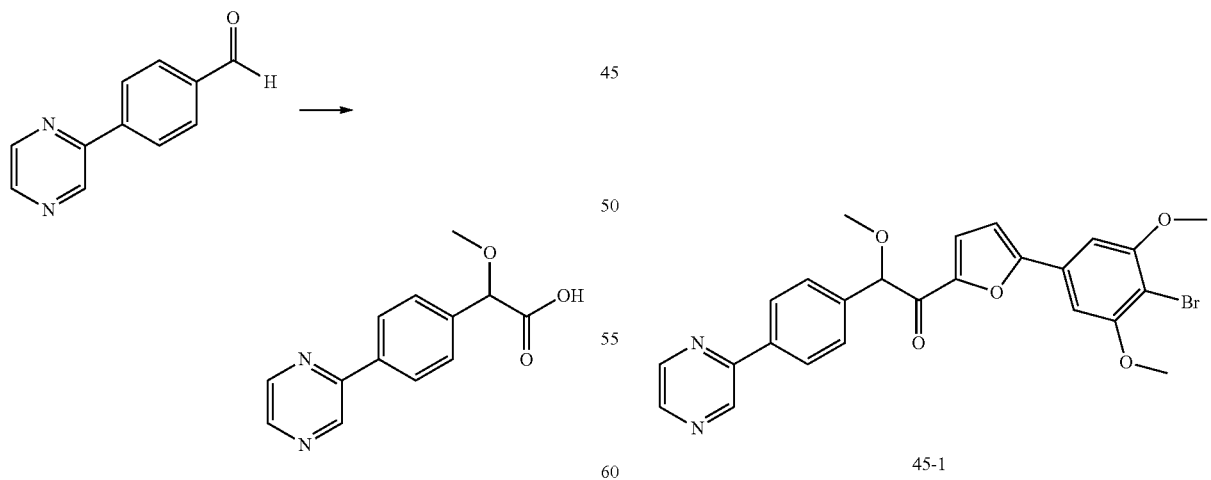

45-1

1-(5-(4-Bromo-3,5-dimethoxyphenyl)furan-2-yl)-2-methoxy-2-(4-(pyrazin-2-yl)phenyl)ethanone was prepared from 2-(4-bromo-3,5-dimethoxyphenyl)furan and N,2-dimethoxy-N-methyl-2-(4-(pyrazin-2-yl)phenyl)acetamide according to the procedure used in Example 30. Purification by chromatography (60% EtOAc/hexanes) gave the product as a pale yellow solid (0.060 g, 17% yield). MS: m/z 509.3 [M+H]⁺.

Example 46

2-Ethoxy-2-(4-(5-Methyl-1,3,4-Oxadiazol-2-yl)Phenyl)-1-(5-(3,4,5-Trimethoxyphenyl)Furan-2-yl)Ethanone

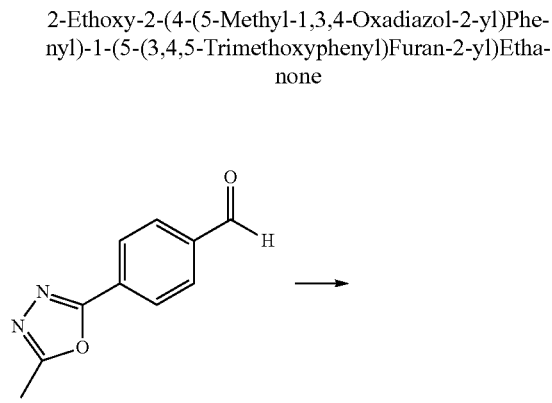

2-Ethoxy-2-(4-(5-methyl-1,3,4-oxadiazol-2-yl)phenyl) acetic acid was synthesized from 4-(5-methyl-1,3,4-oxadiazol-2-yl)benzaldehyde following the procedure for Example 47. The product was isolated as a semisolid and used without further purification (2.6 g, 93% yield).

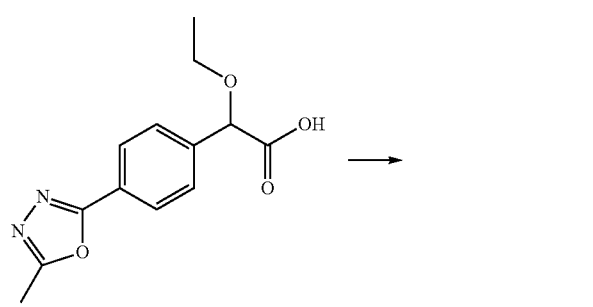

2-Ethoxy-N-methoxy-N-methyl-2-(4-(5-methyl-1,3,4-oxadiazol-2-yl)phenyl)acetamide was synthesized from 2-ethoxy-2-(4-(5-methyl-1,3,4-oxadiazol-2-yl)phenyl)acetic acid according to the procedure for the synthesis of Example 41. Purification by chromatography of (0-60% EtOAc-hexanes) gave the product as an oil (1.0 g, 30% yield).

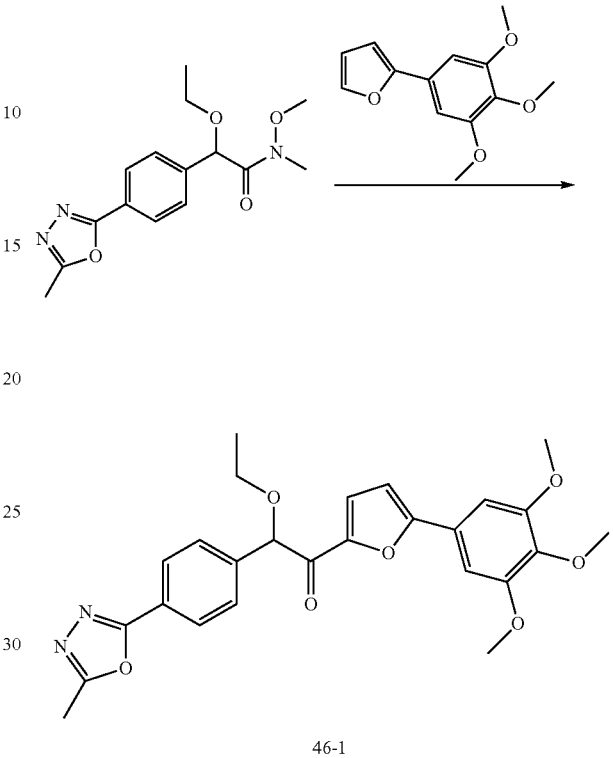

46-1

2-Ethoxy-2-(4-(5-methyl-1,3,4-oxadiazol-2-yl)phenyl)-1-(5-(3,4,5-trimethoxyphenyl)furan-2-yl)ethanone was prepared from 2-(3,4,5-trimethoxyphenyl)furan and 2-ethoxy-N-methoxy-N-methyl-2-(4-(5-methyl-1,3,4-oxadiazol-2-yl)phenyl)acetamide according to the procedure used in Example 30. Purification by chromatography (60% EtOAc/hexanes) gave the product as a pale yellow solid (0.060 g, 15% yield). MS: m/z 479.4 [M+H]⁺.

Example 47

1-(5-(4-Bromo-3,5-Dimethoxyphenyl)Furan-2-yl)-2-Ethoxy-2-(4-(5-Methyl-1,3,4-Oxadiazol-2-yl)Phenyl)Ethanone

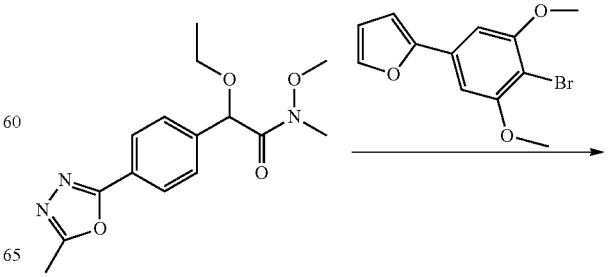

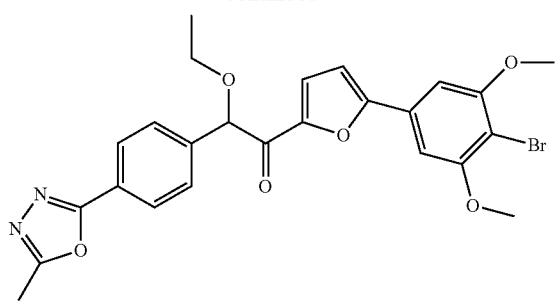

47-1

1-(5-(4-Bromo-3,5-dimethoxyphenyl)furan-2-yl)-2-ethoxy-2-(4-(5-methyl-1,3,4-oxadiazol-2-yl)phenyl)ethanone was prepared from 2-(4-bromo-3,5-dimethoxyphenyl)furan and 2-ethoxy-N-methoxy-N-methyl-2-(4-(5-methyl-1,3,4-oxadiazol-2-yl)phenyl)acetamide according to the procedure used in Example 30. Purification by chromatography (60% EtOAc/hexanes) gave the product as a pale yellow solid (0.070 g, 19% yield). MS: m/z 527.3 [M+H]$^+$.

Example 48

1-(5-(4-Fluoro-3,5-Dimethoxyphenyl)Furan-2-yl)-2-Methoxy-2-(4-Morpholinophenyl)Ethanone

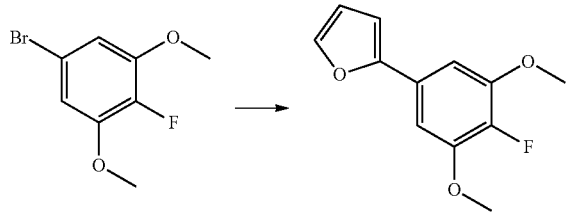 [SMILES: COc1cc(Br)cc(OC)c1F ; COc1cc(-c2ccco2)cc(OC)c1F]

2-(4-Fluoro-3,5-dimethoxyphenyl)furan was prepared from 5-bromo-2-fluoro-1,3-dimethoxybenzene (US6177154 B1) according to the procedure used in Example 15. Purification by chromatography (10% EtOAc/hexanes) gave the product as a white solid (2.1 g, 58% yield).

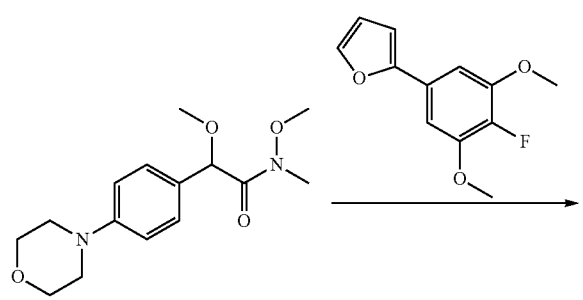

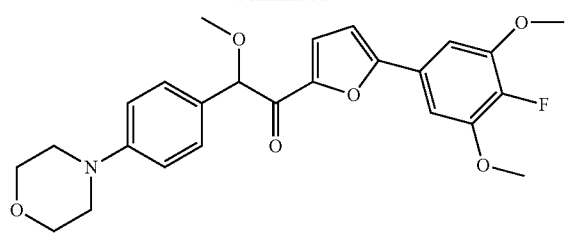

48-1

1-(5-(4-Fluoro-3,5-dimethoxyphenyl)furan-2-yl)-2-methoxy-2-(4-morpholinophenyl)ethanone was prepared from 2-(4-fluoro-3,5-dimethoxyphenyl)furan and N,2-dimethoxy-N-methyl-2-(4-morpholinophenyl)acetamide according to the procedure used in Example 30. Purification by chromatography (60% EtOAc/hexanes) gave the product as a pale yellow solid (0.072 g, 16% yield). MS: m/z 456.4 [M+H]$^+$.

Example 49

1-(5-(4-Chloro-3,5-Dimethoxyphenyl)Furan-2-yl)-2-Methoxy-2-(4-(5-Methyl-1,3,4-Thiadiazol-2-yl)Phenyl)Ethanone

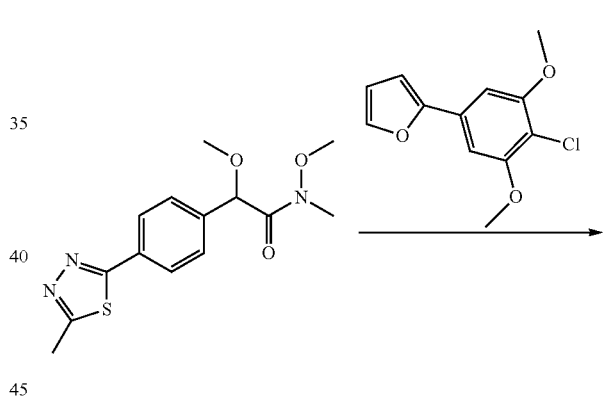

49-1

1-(5-(4-Chloro-3,5-dimethoxyphenyl)furan-2-yl)-2-methoxy-2-(4-(5-methyl-1,3,4-thiadiazol-2-yl)phenyl)ethanone was prepared from 2-(4-chloro-3,5-dimethoxyphenyl)furan and N,2-dimethoxy-N-methyl-2-(4-(5-methyl-1,3,4-thiadiazol-2-yl)phenyl)acetamide according to the procedure used in Example 30. Purification by chromatography (80%

EtOAc-hexanes) gave the product as a pale yellow solid (0.106 g, 26% yield). MS: m/z 485.4 [M+H]+.

Example 50

1-(5-(4-Chloro-3,5-Dimethoxyphenyl)Furan-2-yl)-2-Methoxy-2-(4-Morpholinophenyl)Ethanone

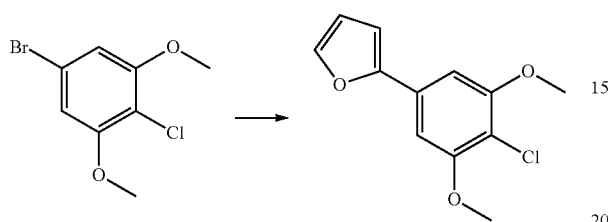

2-(4-Chloro-3,5-dimethoxyphenyl)furan was prepared from 5-bromo-2-chloro-1,3-dimethoxybenzene (EP1568691 A1) according to the procedure used in Example 15. Purification by chromatography (10% ether/hexanes) gave the product as a white solid (1.24 g, 75% yield).

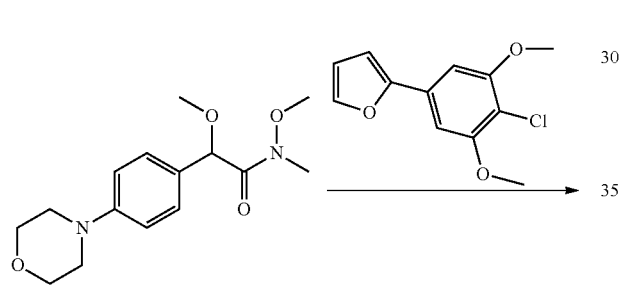

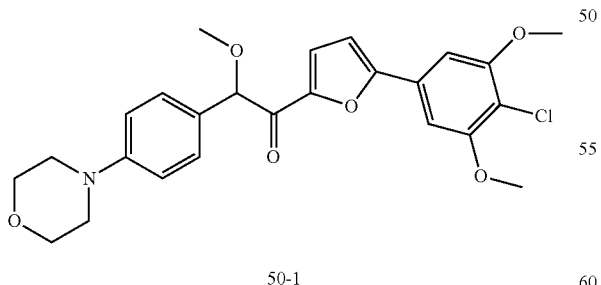

50-1

1-(5-(4-chloro-3,5-dimethoxyphenyl)furan-2-yl)-2-methoxy-2-(4-morpholinophenyl)ethanone was prepared from 2-(4-chloro-3,5-dimethoxyphenyl)furan and N,2-dimethoxy-N-methyl-2-(4-morpholinophenyl)acetamide according to the procedure used in Example 30. Purification by chromatography (70% EtOAc/hexanes) gave the product as a pale yellow solid (0.201 g, 43% yield). MS: m/z 472.2 [M+H]+.

Example 51

1-(3-(3,4-Dimethoxyphenyl)-1H-Pyrazol-1-yl)-2-(4-Fluorophenyl)-2-Methoxyethanone

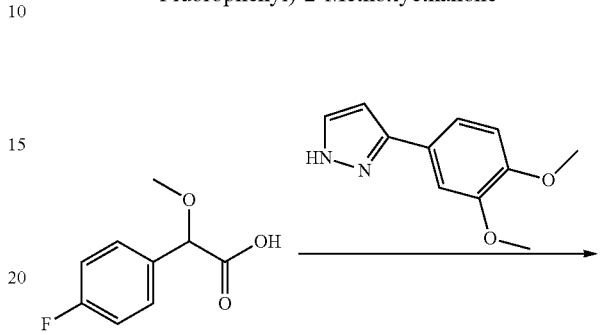

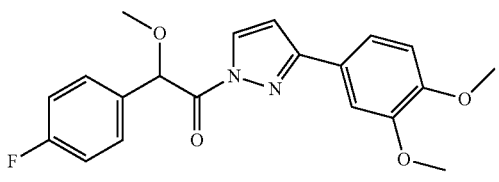

51-1

To a solution of 2-(4-fluorophenyl)-2-methoxyacetic acid (0.11 g, 0.61 mmol) in anhydrous THF (2 mL) at room temperature was added DCC (0.14 g, 0.67 mmol) in one portion. After stirring for 10 min, 3-(3,4-dimethoxyphenyl)-1H-pyrazole (0.14 g, 0.67 mmol) was added in one portion. After 48 hrs, the reaction mixture was diluted with EtOAc and the solids removed via filtration. The filtrate was concentrated in vacuo. Purification by chromatography (0-30% EtOAc-hexanes) gave the product as an oil (0.12 g, 46% yield). MS: m/z 371.1 [M+H]+.

Example 52

1-(3-(4-Bromo-3,5-Dimethoxyphenyl)-1H-Pyrazol-1-yl)-2-Methoxy-2-(4-Morpholinophenyl)Ethanone

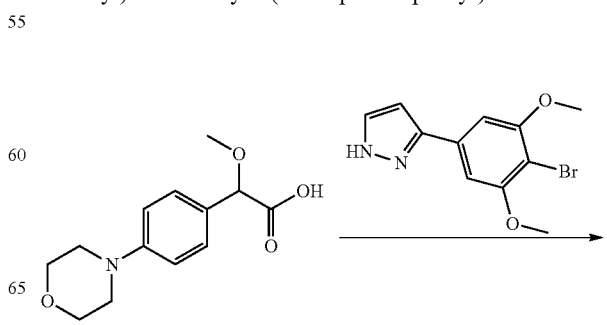

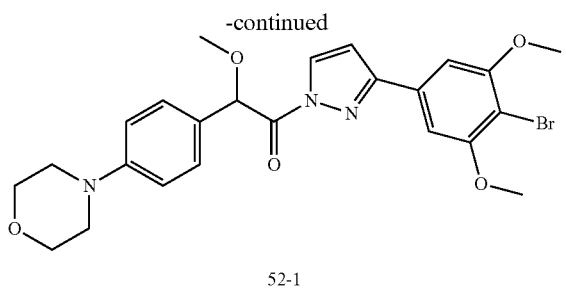

52-1

1-(3-(4-Bromo-3,5-dimethoxyphenyl)-1H-pyrazol-1-yl)-2-methoxy-2-(4-morpholinophenyl)ethanone was synthesized from 3-(4-bromo-3,5-dimethoxyphenyl)-1H-pyrazole (prepared according to *Journal of Org. Chem.*, 2003, 68, 5381) and 2-methoxy-2-(4-morpholinophenyl)acetic acid using the analogous procedure as for Example 51 to give 1-(3-(4-bromo-3,5-dimethoxyphenyl)-1H-pyrazol-1-yl)-2-methoxy-2-(4-morpholinophenyl)ethanone as a solid (0.065 g, 22% yield). MS: m/z 516.1 [M+H]+.

Example 53

1-(3-(3,4-Dimethoxyphenyl)-1H-Pyrazol-1-yl)-2-Methoxy-2-(4-Morpholinophenyl)Ethanone

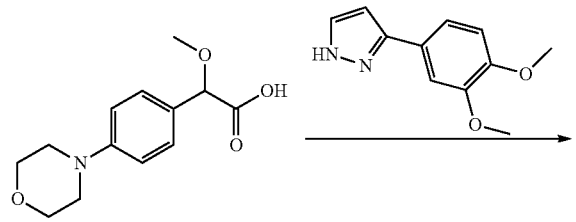

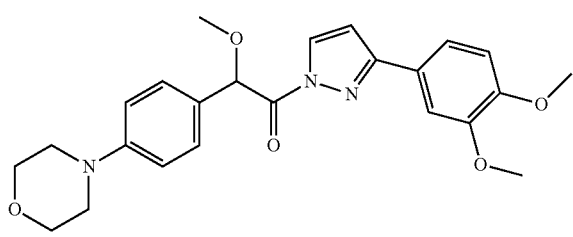

53-1

To a solution of 2-methoxy-2-(4-morpholinophenyl)acetic acid (0.1 g, 0.42 mmol) and 3-(3,4-dimethoxyphenyl)-1H-pyrazole (0.86 g, 0.42 mmol) in anhydrous DMF (4 mL) at room temperature was added diisopropylethylamine (0.22 ml, 1.26 mmol) then bromotripyrrolidinophosphonium hexafluorophosphate (0.23 g, 0.50 mmol). After 24 hrs, saturated aqueous NaHCO₃ was added. The layers were separated and the aqueous layer was extracted with EtOAc. The combined organics were washed with H₂O and brine, dried over Na₂SO₄ and concentrated in vacuo. Purification by chromatography (0-60% EtOAc-hexanes) gave 1-(3-(3,4-dimethoxyphenyl)-1H-pyrazol-1-yl)-2-methoxy-2-(4-morpholinophenyl)ethanone as a white solid (0.90 g, 50% yield). MS: m/z 438.2 [M+H]+.

Example 54

1-(5-(4-Bromo-3,5-Dimethoxyphenyl)-1,2,4-Oxadiazol-3-yl)-2-Methoxy-2-(4-Morpholinophenyl)Ethanone

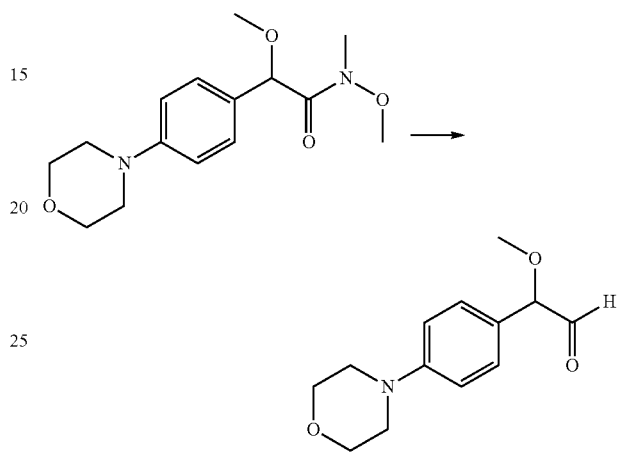

To a solution of N,2-dimethoxy-N-methyl-2-(4-morpholinophenyl)acetamide (1.5 g, 5.1 mmol) in anhydr CH₂Cl₂ (12 mL) and anhydr toluene (6 mL) at −78° C. was added a solution of DIBALH (1 M in hexanes, 7.8 mL, 7.8 mmol) dropwise over 5 min. After stirring at −78° C. for 1 hr, the reaction was quenched with the dropwise addition of EtOAc. The mixture was stirred 2 min then Et₂O and saturated aqueous NH₄Cl were added and the mixture was warmed to room temp. After stirring for 30 min the mixture was diluted with EtOAc and H₂O and the layers separated. 10% Aqueous potassium sodium tartrate was added to the aqueous layer and it was extracted with EtOAc/Et₂O. The combined organics were washed with saturated aqeuous NH₄Cl and dried over Na₂SO₄ to give 2-methoxy-2-(4-morpholinophenyl)acetaldehyde as a yellow oil (1.27 g). The product was used in the next synthetic step without further purification.

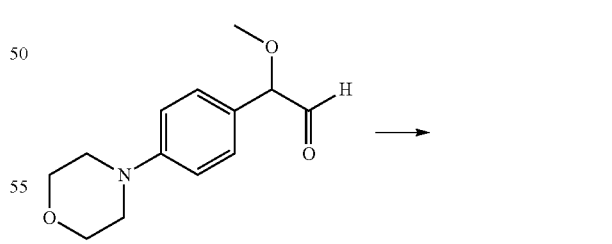

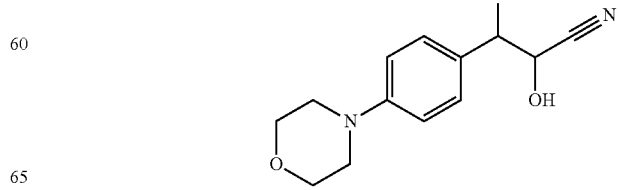

To a solution of 2-methoxy-2-(4-morpholinophenyl)acetaldehyde (1.27 g, ~5.1 mmol) in Et₂O (35 mL) under a drying tube was added trimethylsilyl cyanide (1 mL, 8 mmol) and ZnI₂ (50 mg, 0.16 mmol). After stirring at room temperature for 15.5 hrs, saturated aqueous NaHCO₃ was added and the mixture was stirred several hrs. The mixture was diluted with EtOAc and H₂O and the layers were separated. The organic layers were washed with saturated aqueous NaHCO₃, dried over Na₂SO₄ and concentrated in vacuo to give 2-hydroxy-3-methoxy-3-(4-morpholinophenyl)propanenitrile as an orange foam (1.26 g). The product was used without further purification.

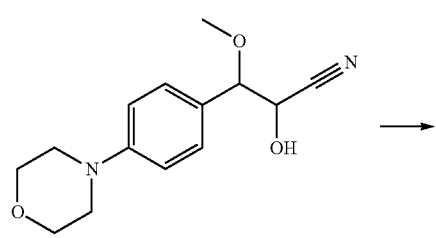

To a solution of 2-hydroxy-3-methoxy-3-(4-morpholinophenyl)propanenitrile (~5.1 mmol) in anhydr CH₂Cl₂ (17 mL) under argon was added pyridinium para-toluenesulfonate (0.094 g, 0.37 mmol) and ethyl vinyl ether (17 mL, 178 mmol). The mixture was placed under a drying tube and stirred at room temperature for 16 hrs. Additional ethylvinyl ether (4 mL, 42 mmol) and pyridinium para-toluenesulfonate (0.11 g, 0.44 mmol) were added and the mixture stirred for 24 hrs more. Saturated aqueous NaHCO₃ was added to the mixture then it was diluted with H₂O and CH₂Cl₂. The layers were separated and the aqueous layer was extracted with CH₂Cl₂. The combined organics were washed with brine, dried over MgSO₄ and concentrated in vacuo. Purification by chromatography (20-35% EtOAc-hexanes containing 1% Et₃N) gave 2-(1-ethoxyethoxy)-3-methoxy-3-(4-morpholinophenyl)propanenitrile (0.606 g, 35% for three steps).

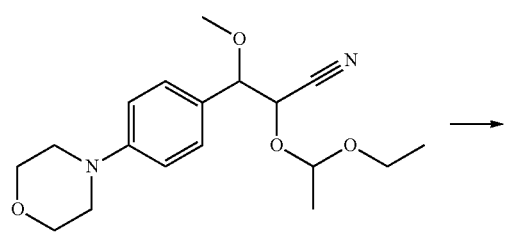

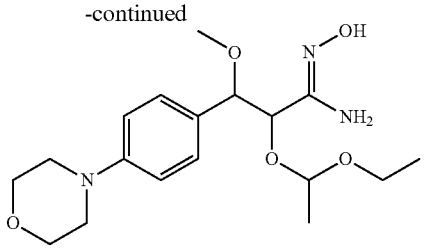

To a solution of 2-(1-ethoxyethoxy)-3-methoxy-3-(4-morpholinophenyl)propanenitrile (0.60 g, 1.8 mmol) in anhydr MeOH (10 mL) under argon was added NH₂OH.HCl (0.175 g, 2.5 mmol) and NaHCO₃ (0.234 g, 2.8 mmol). The reaction was heated briefly at 75° C. then at 60° C. for 16 hrs. After cooling to room temp, the mixture was concentrated in vacuo to give (Z)-2-(1-ethoxyethoxy)-N-hydroxy-3-methoxy-3-(4-morpholinophenyl)propanimidamide which was used in the next synthetic step without further purification (0.777 g).

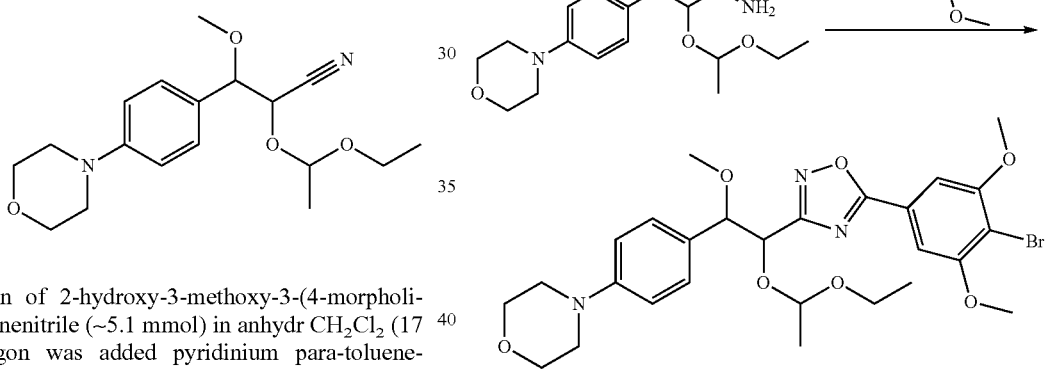

To an ice-cold suspension of (Z)-2-(1-ethoxyethoxy)-N-hydroxy-3-methoxy-3-(4-morpholinophenyl)propanimidamide (~1.41 mmol) in anhydr CH₂Cl₂ under argon was added Et₃N (0.8 mL, 5.7 mmol), 4-bromo-3,5-dimethoxybenzoyl chloride (0.434 g, 1.6 mmol) and 4-dimethylaminopyridine (0.015 g, 0.12 mmol). The reaction was stirred for 1 hr over an ice bath then allowed to warm to room temperature. After stirring for 3 hrs at room temp, additional 4-bromo-3,5-dimethoxybenzoyl chloride (0.047 g, 0.17 mmol) was added and the mixture was stirred for an additional hour. 10% Aqueous NaHCO₃ solution was added and stirred for 20 min. The layers were separated and the organic layer was washed with H₂O, brine, dried over MgSO₄ and concentrated in vacuo to give an off-white foam.

This synthetic intermediate was dissolved in anhydr DMF (15 mL) under argon then heated at 120° C. for 7 hrs. After cooling to room temp, the reaction was diluted with H₂O and extracted with EtOAc. The combined organics were washed with H₂O and brine, dried over Na₂SO₄ and concentrated in vacuo. Purification by chromatography (25-35% EtOAc-hexanes containing 1% Et₃N) gave 4-(4-(2-(5-(4-bromo-3,5-dimethoxyphenyl)-1,2,4-oxadiazol-3-yl)-2-(1-ethoxyethoxy)-1-methoxyethyl)phenyl)morpholine as a light yellow oil (0.335 g, 40% yield).

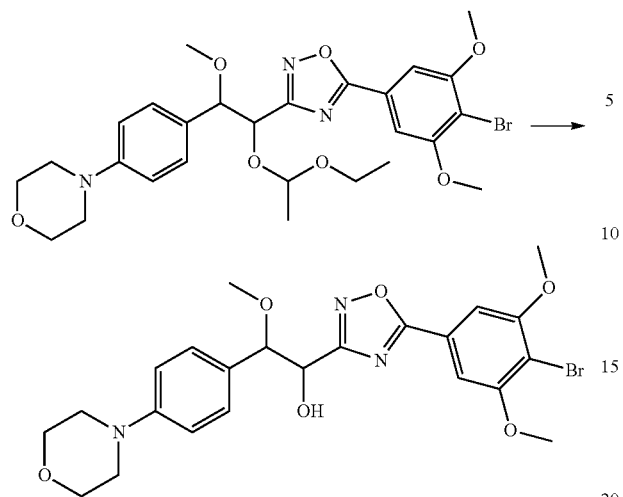

To a solution of 4-(4-(2-(5-(4-bromo-3,5-dimethoxyphenyl)-1,2,4-oxadiazol-3-yl)-2-(1-ethoxyethoxy)-1-methoxyethyl)phenyl)morpholine (0.335 g, 0.57 mmol) in MeOH (15 mL) was added pyridinium para-toluenesulfonate (0.15 g, 0.6 mmol) and the mixture was stirred at room temperature for 16.5 hrs. The reaction was then heated at 40° C. for 6 hrs, cooled to room temp, and concentrated in vacuo. The residue was dissolved in EtOAc and washed with H₂O, saturated NaHCO₃ and brine then dried over Na₂SO₄ and concentrated in vacuo. Purification by chromatography (50-60% EtOAc-hexanes) gave 1-(5-(4-bromo-3,5-dimethoxyphenyl)-1,2,4-oxadiazol-3-yl)-2-methoxy-2-(4-morpholinophenyl)ethanol as a colorless residue (0.234, 79% yield).

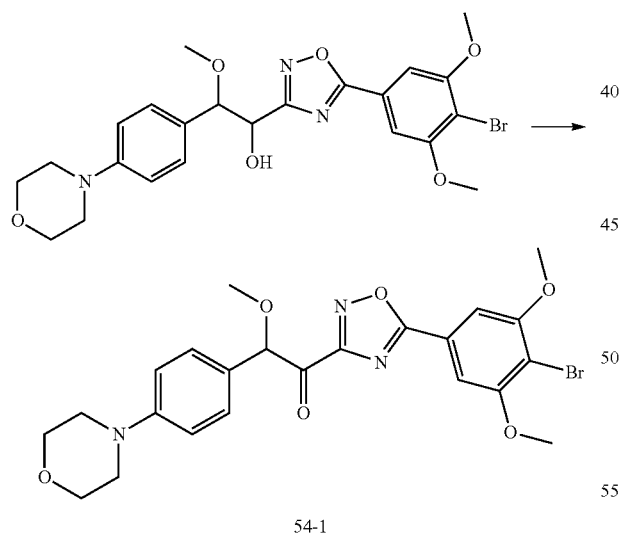

54-1

To a solution of 1-(5-(4-bromo-3,5-dimethoxyphenyl)-1,2,4-oxadiazol-3-yl)-2-methoxy-2-(4-morpholinophenyl)ethanol (0.18 g, 0.35 mmol) in anhydr CH₂Cl₂ (4 mL) under argon was added 1,1,1-tris(acetyloxy)-1,1-dihydro-1,2-benziodoxol-3-(1H)-one (0.198 g, 0.47 mmol). After stirring at room temperature for 50 min, the mixture was diluted with Et₂O, saturated aqueous NaHCO₃ and 20% Na₂S₂O₃. The layers were separated and the organic layer was washed with saturated NaHCO₃, dried over Na₂SO₄ and concentrated in vacuo. Purification by chromatography (40-50% EtOAc-hexanes) gave the product as a bright yellow solid (0.1249 g, 70% yield). MS: m/z 518.1 [M+H]⁺.

Example 55

1-(4-(4-Bromo-3,5-Dimethoxyphenyl)-5-Methyloxazol-2-yl)-2-Methoxy-2-(4-Morpholinophenyl)Ethanone

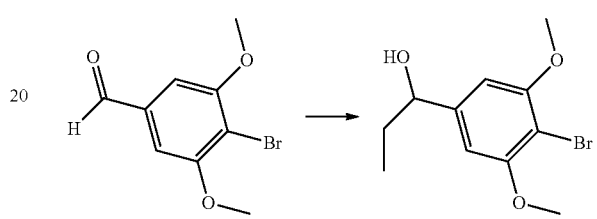

An oven-dried flask under argon was charged with 4-bromo-3,5-dimethoxybenzaldehyde (5.0 g, 20.4 mmol) and anhydrous THF (30 mL). The mixture was cooled over ice then a solution of ethyl magnesium bromide (3.0 M in diethyl ether, 8.2 mL, 24.5 mmol) was added dropwise from an addition funnel over a period of 45 min. After stirring for 20 min, the mixture was allowed to warm to room temperature and stirred for 19 hrs. After quenching with a solution of aqueous NH₄Cl, it was diluted with H₂O and EtOAc then cooled over an ice bath. After the mixture was cooled, the layers were separated. The organics were washed with H₂O and brine then dried over Na₂SO₄ and concentrated in vacuo. The residue was dissolved in CH₂Cl₂ and concentrated in vacuo again to give 1-(4-bromo-3,5-dimethoxyphenyl)propan-1-ol as a clear oil (5.43 g, 97% yield). The product was used without further purification.

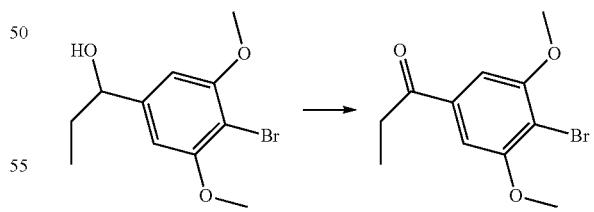

To a solution of 1-(4-bromo-3,5-dimethoxyphenyl)propan-1-ol (5.4 g, 19.6 mmol) in anhydrous CH₂Cl₂ (75 mL) was added MnO₂ (17 g, 196 mmol). After the mixture was placed under a drying tube and stirred at room temperature for 22 hrs, it was filtered through a pad of Celite and silica gel and rinsed with EtOAc. Concentration of the filtrate in vacuo gave 1-(4-bromo-3,5-dimethoxyphenyl)propan-1-one as a white solid (5.4 g, 100% yield). The product was used without further purification.

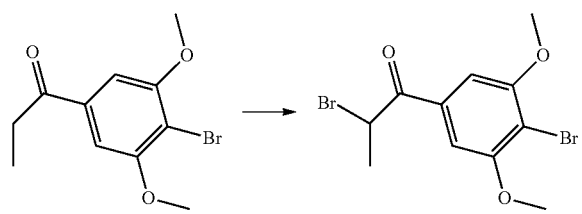 [SMILES: CCC(=O)c1cc(OC)c(Br)c(OC)c1 ; COc1cc(C(=O)C(C)Br)cc(OC)c1Br]

To a solution of 1-(4-bromo-3,5-dimethoxyphenyl)propan-1-one (1.50 g, 5.49 mmol) in anhydrous THF (20 mL) was added pyridinium tribromide (1.93 g, 6.04 mmole). The reaction was stirred at room temperature for 2 hrs then neutralized with a solution of saturated aqueous NaHCO$_3$. The mixture was extracted with EtOAc the combined organics were washed with saturated aqueous NaHCO$_3$ and brine then dried over Na$_2$SO$_4$ and concentrated in vacuo. Purification by chromatography (10-20% EtOAc-hexanes) gave 2-bromo-1-(4-bromo-3,5-dimethoxyphenyl)propan-1-one as an orange oil (1.09 g, 56% yield).

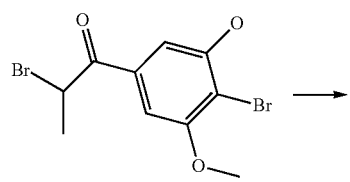

A solution of 2-bromo-1-(4-bromo-3,5-dimethoxyphenyl)propan-1-one (1.07 g, 3.04 mmol) in formamide (10 mL) in an oven-dried flask under argon was heated at 110° C. for 16 hrs. After cooling to room temp, EtOAc and saturated aqueous NaHCO$_3$ were carefully added and the mixture was stirred for 15 minutes. It was then extracted with EtOAc twice and the combined organics were washed with H$_2$O and brine, dried over Na$_2$SO$_4$ and concentrated. Purification by chromatography (30% EtOAc-hexanes) gave 4-(4-bromo-3,5-dimethoxyphenyl)-5-methyloxazole as a yellow solid (0.496 g, 55% yield).

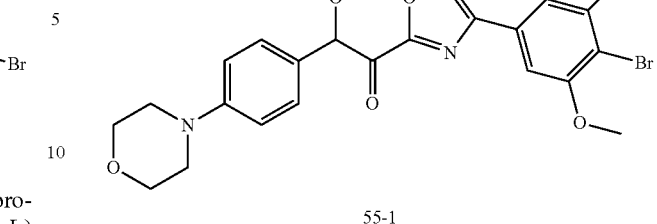

55-1

1-(4-(4-Bromo-3,5-dimethoxyphenyl)-5-methyloxazol-2-yl)-2-methoxy-2-(4-morpholinophenyl)ethanone was prepared from 4-(4-bromo-3,5-dimethoxyphenyl)-5-methyloxazole and N,2-dimethoxy-N-methyl-2-(4-morpholinophenyl)acetamide according to the procedure used in Example 30. Purification by chromatography (40% EtOAc-hexanes) gave the product as a yellow solid (0.048 g, 13% yield). MS: m/z 531.1 [M+H]$^+$.

Example 56

1-(5-(4-Bromo-3,5-Dimethoxyphenyl)Oxazol-2-yl)-2-Methoxy-2-(4-Morpholinophenyl)Ethanone

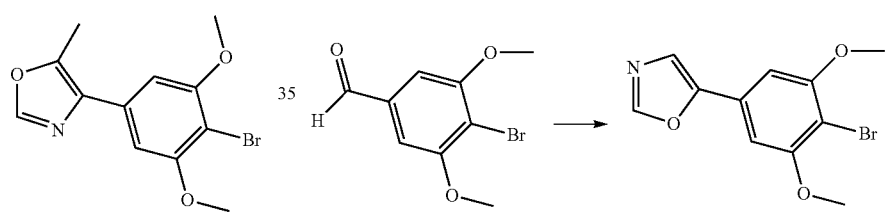

A solution of 4-bromo-3,5-dimethoxybenzaldehyde (5.04 g, 20.57 mmole) and toluenesulfonylmethyl isocyanide (4.22 g, 21.6 mmole) in MeOH (50 ml) was heated at reflux for 3 hrs. After evaporation to near dryness, H$_2$O (50 ml) and EtOAc (200 ml) were added with stirring. The organic layer was separated and washed with brine (50 ml), dried over Na$_2$SO$_4$ and concentrated in vacuo. Et$_2$O (50 ml) was added with swirling and the product was collected by filtration, washed with Et$_2$O (2×25 ml) and dried giving 5-(4-bromo-3,5-dimethoxyphenyl)oxazole as a pale yellow solid (2.25 g, 39% yield).

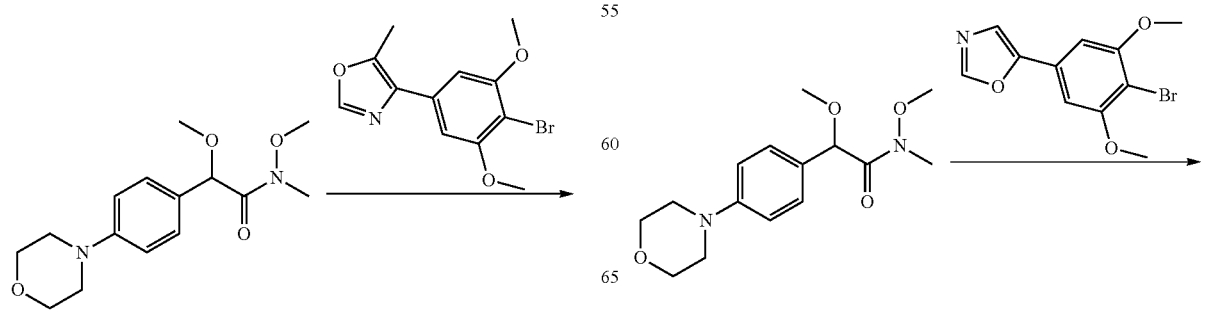

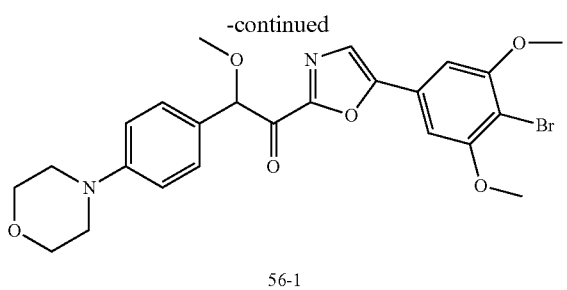

56-1

1-(5-(4-Bromo-3,5-dimethoxyphenyl)oxazol-2-yl)-2-methoxy-2-(4-morpholinophenyl)ethanone was prepared from 5-(4-bromo-3,5-dimethoxyphenyl)oxazole and N,2-dimethoxy-N-methyl-2-(4-morpholinophenyl)acetamide according to the procedure used in Example 30. Recrystallization from EtOAc gave the product as a yellow solid (0.308 g, 56% yield). MS: m/z 517.3 [M+H]$^+$.

Example 57

1-(5-(4-Bromo-3,5-Dimethoxyphenyl)Thiophen-2-yl)-2-Methoxy-2-(4-(5-Methyl-1,3,4-Oxadiazol-2-yl)Phenyl)Ethanone

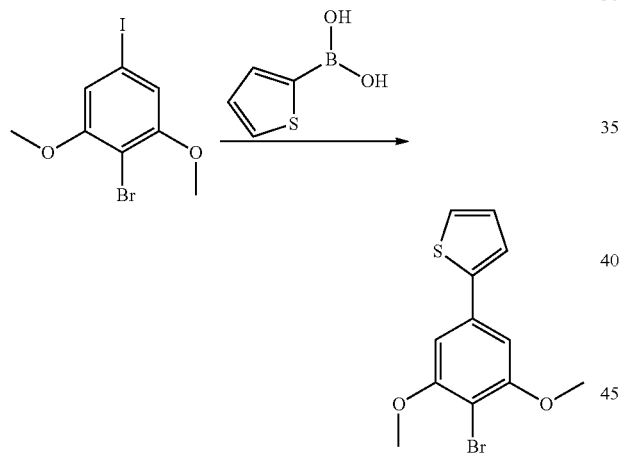

2-(4-Bromo-3,5-dimethoxyphenyl)thiophene was prepared from 2-bromo-5-iodo-1,3-dimethoxybenzene and thiophen-2-ylboronic acid according to the procedure used in Example 12. Purification by chromatography (0-10% EtOAc-hexanes) gave a yellow solid (0.624 g, 55% yield).

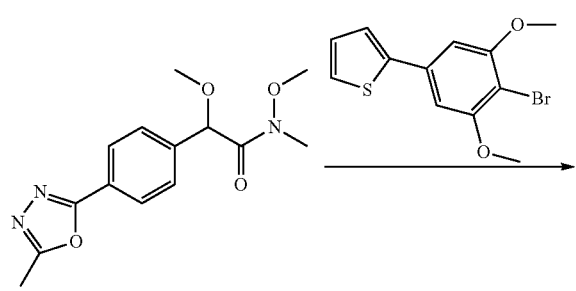

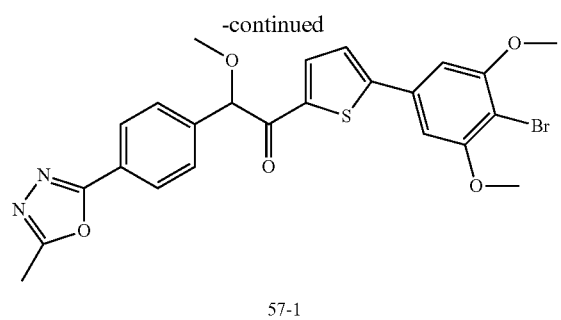

57-1

1-(5-(4-Bromo-3,5-dimethoxyphenyl)thiophen-2-yl)-2-methoxy-2-(4-(5-methyl-1,3,4-oxadiazol-2-yl)phenyl)ethanone was prepared from 2-(4-bromo-3,5-dimethoxyphenyl)thiophene and N,2-dimethoxy-N-methyl-2-(4-(5-methyl-1,3,4-oxadiazol-2-yl)phenyl)acetamide according to the procedure used in Example 30. Purification by chromatography (70% EtOAc-hexanes) gave the product as a yellow foam (0.031 g, 11% yield). MS: m/z 529.2 [M+H]$^+$.

Example 58

1-(4-(4-Bromo-3,5-Dimethoxyphenyl)-5-(Trifluoromethyl)Oxazol-2-yl)-2-Methoxy-2-(4-Morpholinophenyl)Ethanone

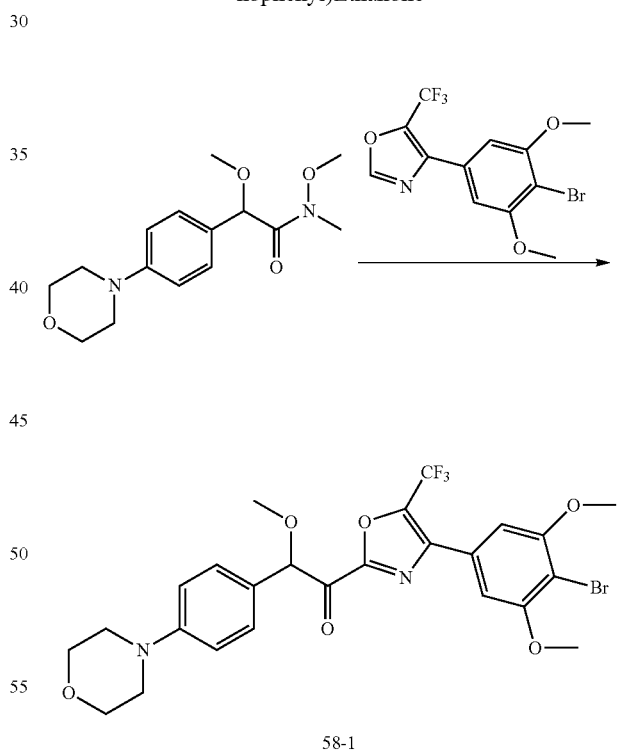

58-1

1-(4-(4-Bromo-3,5-dimethoxyphenyl)-5-(trifluoromethyl)oxazol-2-yl)-2-methoxy-2-(4-morpholinophenyl)ethanone was prepared from 4-(4-bromo-3,5-dimethoxyphenyl)-5-(trifluoromethyl)oxazole (prepared from 4-bromo-3,5-dimethoxybenzaldehyde according to *Heterocycles*, 1992, 34, 1047) and N,2-dimethoxy-N-methyl-2-(4-morpholinophenyl)acetamide according to the procedure used in Example 30. Purification by chromatography (20-40%

EtOAc-hexanes) gave the product as a yellow solid (0.032 g, 14% yield). MS: m/z 585.3 [M+H]+.

Example 59

1-(5-(4-Bromo-3,5-Dimethoxyphenyl)Thiophen-2-yl)-2-Methoxy-2-(4-Morpholinophenyl)Ethanone

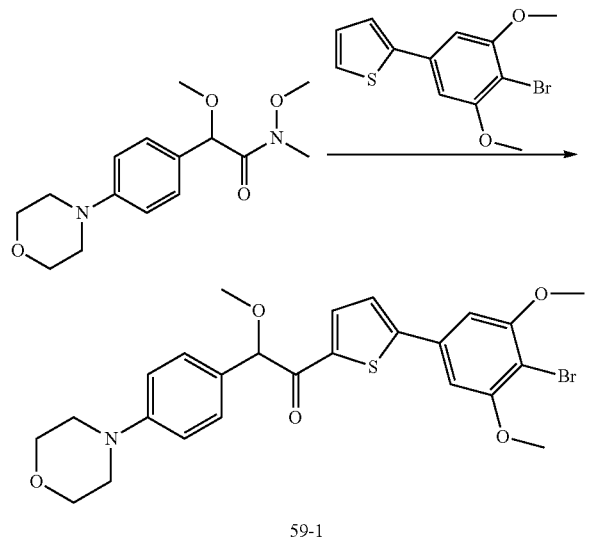

59-1

1-(5-(4-Bromo-3,5-dimethoxyphenyl)thiophen-2-yl)-2-methoxy-2-(4-morpholinophenyl)ethanone was prepared from 2-(4-bromo-3,5-dimethoxyphenyl)thiophene and N,2-dimethoxy-N-methyl-2-(4-morpholinophenyl)acetamide according to the procedure used in Example 30. Purification by chromatography (40% EtOAc-hexanes) gave the product as a yellow solid (0.122 g, 46% yield). MS: m/z 532.4 [M+H]+.

Example 60

2-(4-(5-Cyclopropyl-1,3,4-Oxadiazol-2-yl)Phenyl)-2-Methoxy-1-(5-(3,4,5-Trimethoxyphenyl)Furan-2-yl)Ethanone

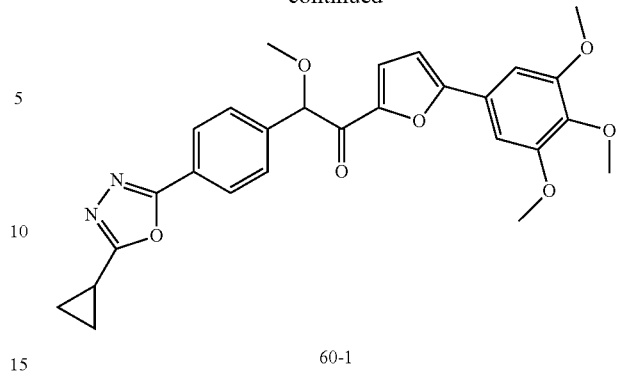

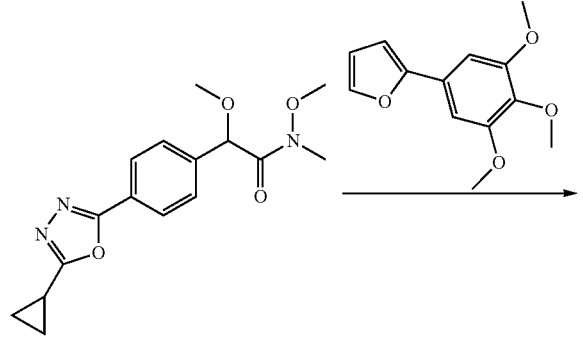

60-1

2-(4-(5-Cyclopropyl-1,3,4-oxadiazol-2-yl)phenyl)-2-methoxy-1-(5-(3,4,5-trimethoxyphenyl)furan-2-yl)ethanone was prepared from 2-(3,4,5-trimethoxyphenyl)furan and 2-(4-(5-cyclopropyl-1,3,4-oxadiazol-2-yl)phenyl)-N,2-dimethoxy-N-methylacetamide according to the procedure used in Example 30. Purification by chromatography (60% EtOAc-hexanes) gave the product as a pale yellow solid (0.129 g, 42% yield). MS: m/z 491.1 [M+H]+.

Example 61

1-(5-(4-Chloro-3,5-Dimethoxyphenyl)Furan-2-yl)-2-Methoxy-2-(4-(5-Methyl-1,3,4-Oxadiazol-2-yl)Phenyl)Ethanone

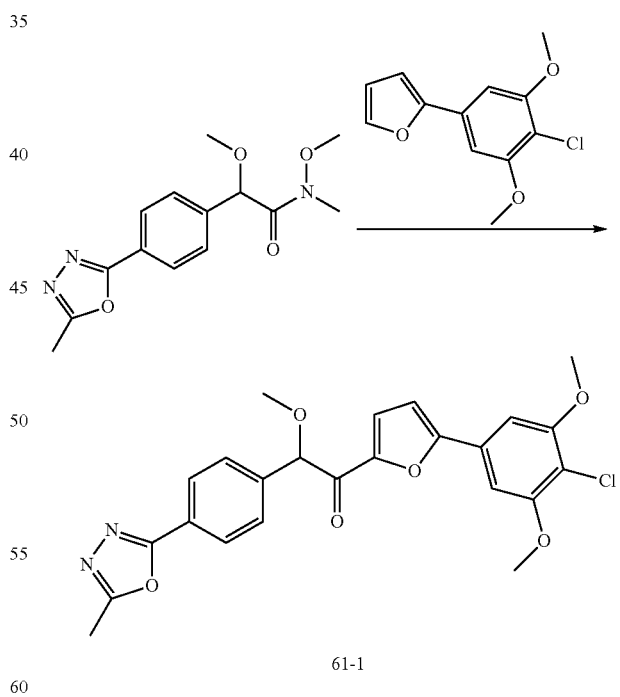

61-1

1-(5-(4-Chloro-3,5-dimethoxyphenyl)furan-2-yl)-2-methoxy-2-(4-(5-methyl-1,3,4-oxadiazol-2-yl)phenyl)ethanone was prepared from 2-(4-chloro-3,5-dimethoxyphenyl)furan and N,2-dimethoxy-N-methyl-2-(4-(5-methyl-1,3,4-oxadiazol-2-yl)phenyl)acetamide according to the procedure used in Example 30. Purification by chromatography (60%

Example 62

1-(5-(4-Fluoro-3,5-Dimethoxyphenyl)Furan-2-yl)-2-Methoxy-2-(4-(5-Methyl-1,3,4-Oxadiazol-2-yl)Phenyl)Ethanone

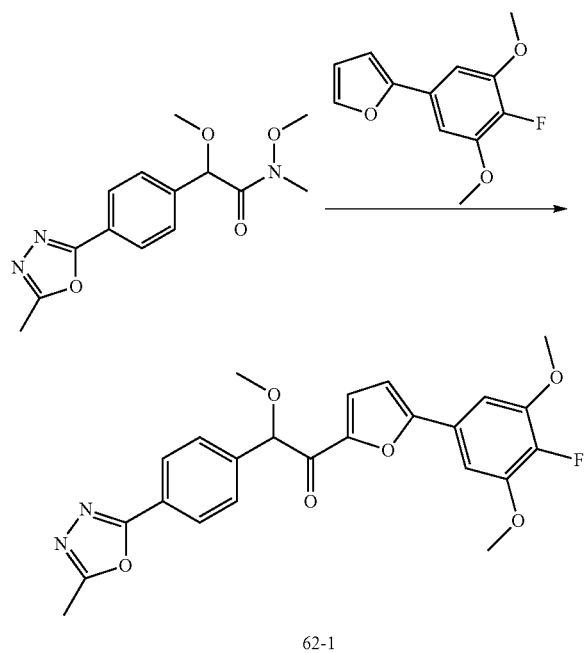

62-1

1-(5-(4-Fluoro-3,5-dimethoxyphenyl)furan-2-yl)-2-methoxy-2-(4-(5-methyl-1,3,4-oxadiazol-2-yl)phenyl)ethanone was prepared from 2-(4-fluoro-3,5-dimethoxyphenyl)furan and N,2-dimethoxy-N-methyl-2-(4-(5-methyl-1,3,4-oxadiazol-2-yl)phenyl)acetamide according to the procedure used in Example 30. Purification by chromatography (60% EtOAc-hexanes) gave the product as a pale yellow solid (0.036 g, 8% yield). MS: m/z 453.2 [M+H]$^+$.

Example 63

1-(5-(4-Chloro-3,5-Dimethoxyphenyl)Furan-2-yl)-2-Ethoxy-2-(4-(5-Methyl-1,3,4-Oxadiazol-2-yl)Phenyl)Ethanone

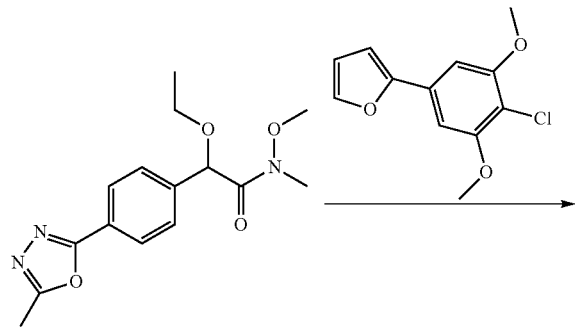

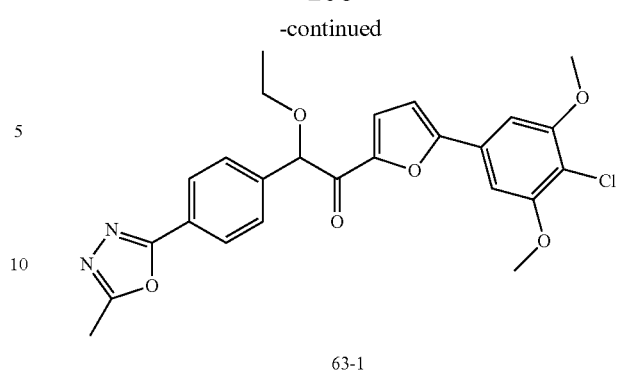

63-1

1-(5-(4-Chloro-3,5-dimethoxyphenyl)furan-2-yl)-2-ethoxy-2-(4-(5-methyl-1,3,4-oxadiazol-2-yl)phenyl)ethanone was prepared from 2-(4-chloro-3,5-dimethoxyphenyl)furan and 2-ethoxy-N-methoxy-N-methyl-2-(4-(5-methyl-1,3,4-oxadiazol-2-yl)phenyl)acetamide according to the procedure used in Example 30. Purification by chromatography (60% EtOAc-hexanes) gave the product as a pale yellow solid (0.122 g, 25% yield). MS: m/z 483.1 [M+H]$^+$.

Example 64

1-(5-(4-Chloro-3,5-Dimethoxyphenyl)Furan-2-yl)-2-Ethoxy-2-(4-Morpholinophenyl)Ethanone

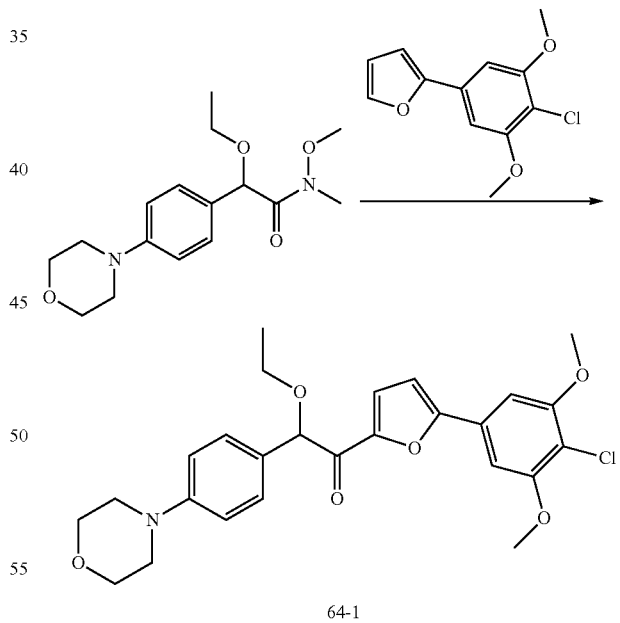

64-1

1-(5-(4-Chloro-3,5-dimethoxyphenyl)furan-2-yl)-2-ethoxy-2-(4-morpholinophenyl)ethanone was prepared from 2-(4-chloro-3,5-dimethoxyphenyl)furan and 2-ethoxy-N-methoxy-N-methyl-2-(4-morpholinophenyl)acetamide according to the procedure used in Example 30. Purification by chromatography (60% EtOAc-hexanes) gave the product as a pale yellow solid (0.127 g, 26% yield). MS: m/z 486.5 [M+H]$^+$.

Example 65

Synthesis of Further Representative Compounds

The following representative compounds in Table 1 were synthesized according to (i) the foregoing procedures by selecting appropriate starting materials and (ii) known organic synthesis techniques.

TABLE 1

| Compound No. | Structure | MS m/z [M + H]⁺ |
|---|---|---|
| 65-1 | 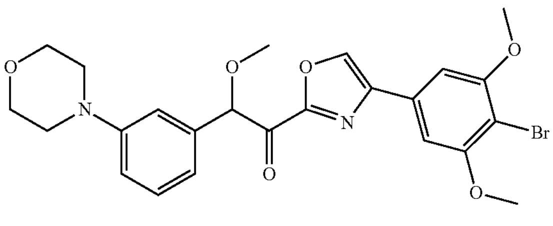 [SMILES: COc1cc(-c2coc(C(=O)C(OC)c3cccc(N4CCOCC4)c3)n2)cc(OC)c1Br] | 517.3 |
| 65-2 | 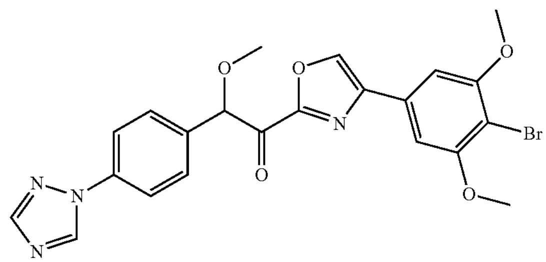 [SMILES: COc1cc(-c2coc(C(=O)C(OC)c3ccc(-n4cncn4)cc3)n2)cc(OC)c1Br] | 499.3 |
| 65-3 | 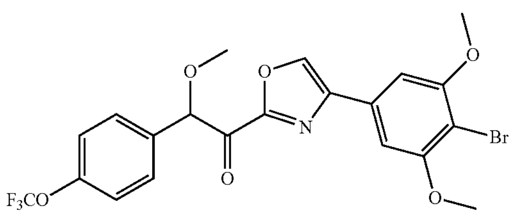 [SMILES: COc1cc(-c2coc(C(=O)C(OC)c3ccc(OC(F)(F)F)cc3)n2)cc(OC)c1Br] | 514.0 [M − H]⁻ |
| 65-4 | 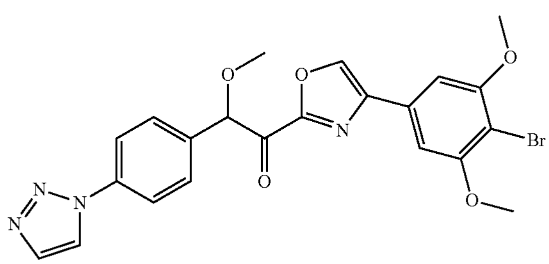 [SMILES: COc1cc(-c2coc(C(=O)C(OC)c3ccc(-n4ccnn4)cc3)n2)cc(OC)c1Br] | 499.3 |
| 65-5 | 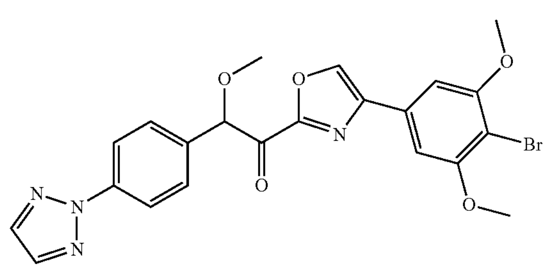 [SMILES: COc1cc(-c2coc(C(=O)C(OC)c3ccc(-n4nccn4)cc3)n2)cc(OC)c1Br] | 499.3 |

TABLE 1-continued

| Compound No. | Structure | MS m/z [M + H]+ |
|---|---|---|
| 65-6 | 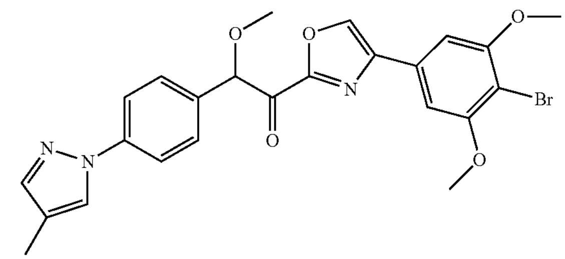 [SMILES: COc1cc(-c2coc(C(=O)C(OC)c3ccc(-n4cc(C)cn4)cc3)n2)cc(OC)c1Br] | 512.4 |
| 65-7 | 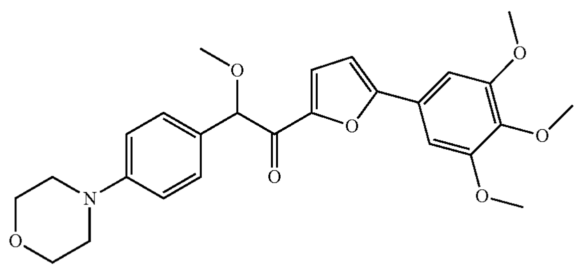 [SMILES: COc1cc(-c2ccc(C(=O)C(OC)c3ccc(N4CCOCC4)cc3)o2)cc(OC)c1OC] | 468.2 |
| 65-8 | 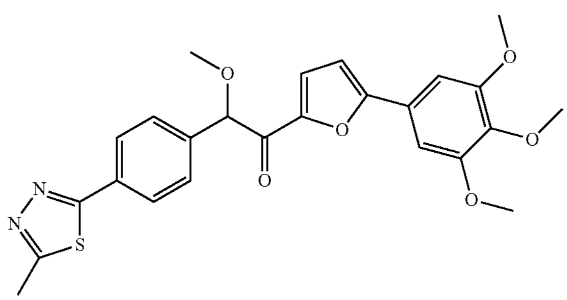 [SMILES: COc1cc(-c2ccc(C(=O)C(OC)c3ccc(-c4nnc(C)s4)cc3)o2)cc(OC)c1OC] | 481.1 |
| 65-9 | 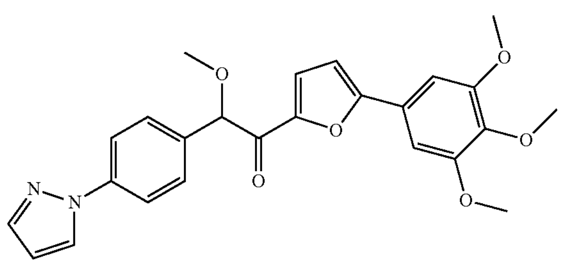 [SMILES: COc1cc(-c2ccc(C(=O)C(OC)c3ccc(-n4cccn4)cc3)o2)cc(OC)c1OC] | 449.2 |
| 65-10 | 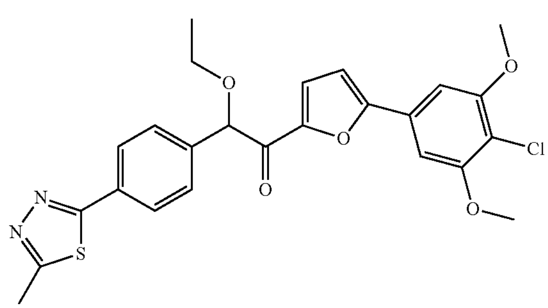 [SMILES: CCOC(C(=O)c1ccc(-c2cc(OC)c(Cl)c(OC)c2)o1)c1ccc(-c2nnc(C)s2)cc1] | 499.1 |

TABLE 1-continued
| Compound No. | Structure | MS m/z [M + H]+ |
|---|---|---|
| 65-11 | 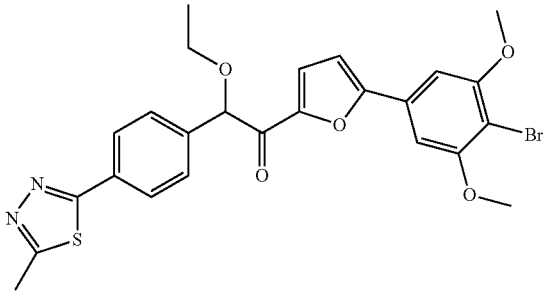 [SMILES: CCOC(C(=O)c1ccc(-c2cc(OC)c(Br)c(OC)c2)o1)c1ccc(-c2nnc(C)s2)cc1] | 543 |
| 65-12 | 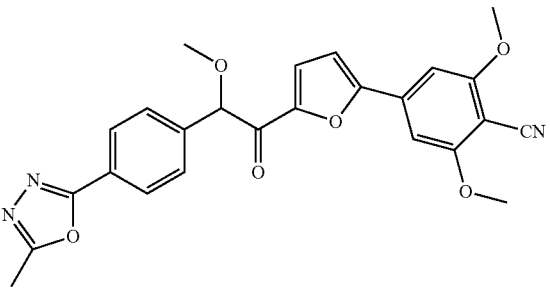 [SMILES: COc1cc(-c2ccc(C(=O)C(OC)c3ccc(-c4nnc(C)o4)cc3)o2)cc(OC)c1C#N] | 460.2 |
| 65-13 | 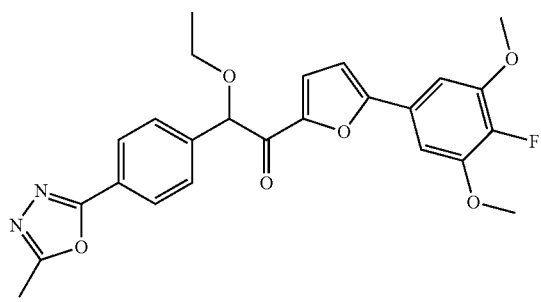 | 467.4 |
| 65-14 | 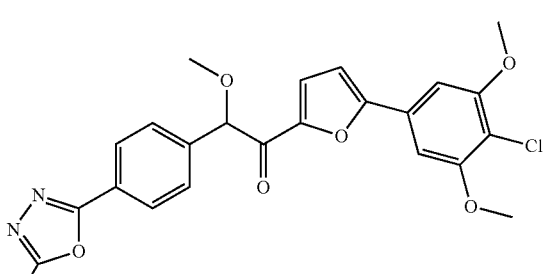 | 469.1 |
| 65-15 | 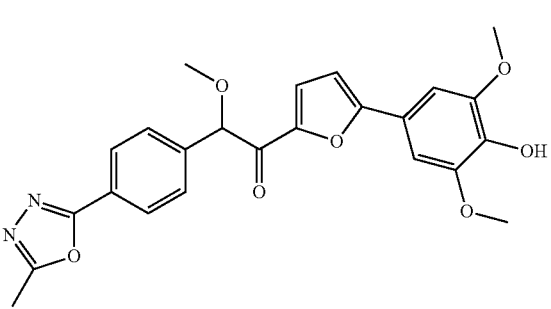 [SMILES: COc1cc(-c2ccc(C(=O)C(OC)c3ccc(-c4nnc(C)o4)cc3)o2)cc(OC)c1O] | 451.2 |

TABLE 1-continued

| Compound No. | Structure | MS m/z [M + H]+ |
|---|---|---|
| 65-16 | | 459.1 |
| 65-16 | | 541.0 |
| 65-17 | 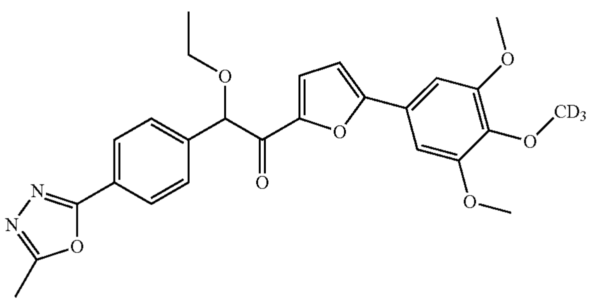 [SMILES: [2H]C([2H])([2H])Oc1c(OC)cc(-c2ccc(C(=O)C(OCC)c3ccc(-c4nnc(C)o4)cc3)o2)cc1OC] | 482.2 |

The following representative compounds in Table 2 are synthesized according to (i) the foregoing procedures by selecting appropriate starting materials and (ii) known organic synthesis techniques.

TABLE 2

| Compound No. | Structure | MW |
|---|---|---|
| 65-18 | 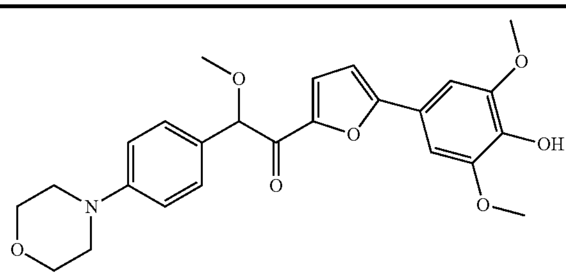 | 453.49 |

TABLE 2-continued
| Compound No. | Structure | MW |
|---|---|---|
| 65-19 | 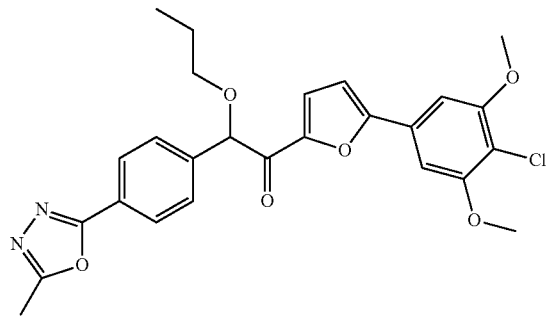 [SMILES: CCCOC(C(=O)c1ccc(-c2cc(OC)c(Cl)c(OC)c2)o1)c1ccc(-c2nnc(C)o2)cc1] | 496.95 |
| 65-20 | 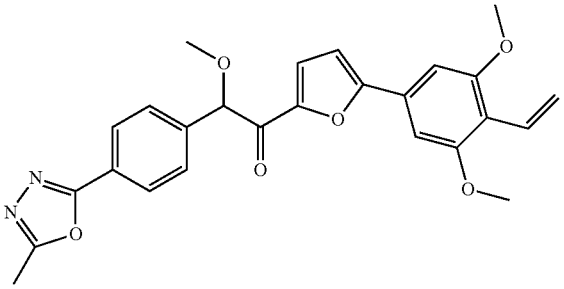 [SMILES: C=Cc1c(OC)cc(-c2ccc(C(=O)C(OC)c3ccc(-c4nnc(C)o4)cc3)o2)cc1OC] | 460.49 |
| 65-21 | 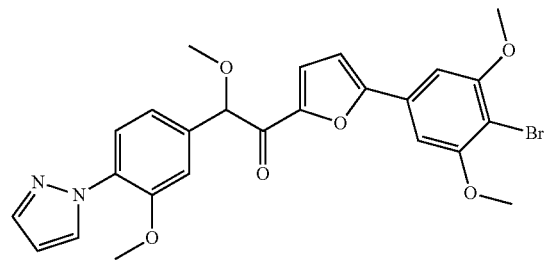 [SMILES: COc1cc(C(OC)C(=O)c2ccc(-c3cc(OC)c(Br)c(OC)c3)o2)ccc1-n1cccn1] | 527.38 |
| 65-22 | 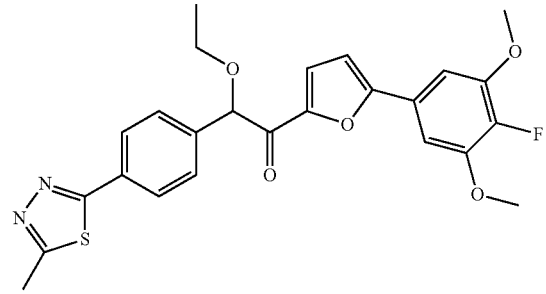 [SMILES: CCOC(C(=O)c1ccc(-c2cc(OC)c(F)c(OC)c2)o1)c1ccc(-c2nnc(C)s2)cc1] | 482.53 |
| 65-23 | 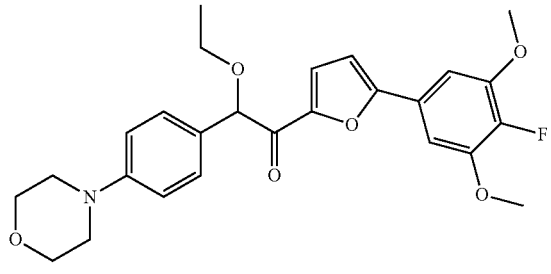 [SMILES: CCOC(C(=O)c1ccc(-c2cc(OC)c(F)c(OC)c2)o1)c1ccc(N2CCOCC2)cc1] | 469.51 |

TABLE 2-continued

| Compound No. | Structure | MW |
|---|---|---|
| 65-24 | 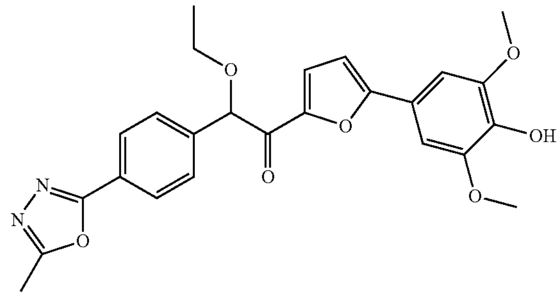 | 464.47 |
| 65-25 | 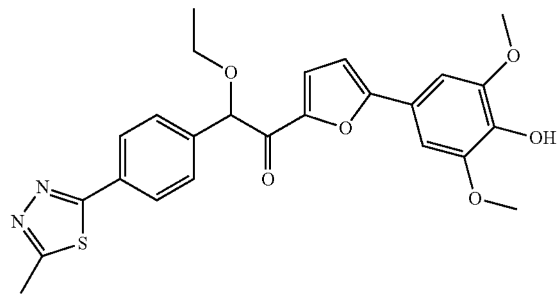 [SMILES: CCOC(C(=O)c1ccc(-c2cc(OC)c(O)c(OC)c2)o1)c1ccc(-c2nnc(C)o2)cc1] | 480.54 |
| 65-26 | 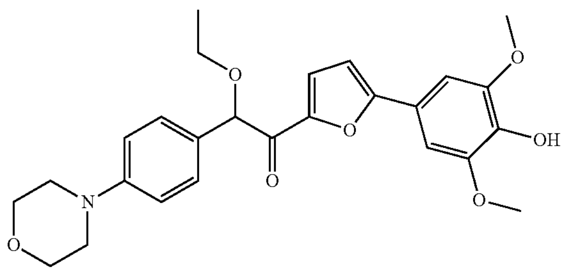 [SMILES: CCOC(C(=O)c1ccc(-c2cc(OC)c(O)c(OC)c2)o1)c1ccc(N2CCOCC2)cc1] | 467.52 |

Example 66

Compound Assay

PDE10 Biochemical Assay

The phosphodiesterase (PDE) assay was performed using recombinant human PDE 1A3, 2A3, 3 catalytic region, 4 catalytic region, 5 catalytic region, 7A, 8A, 9A2, 10A1 and 11A1 enzymes expressed in a baculoviral system using Sf9 cells. PDE activity was measured using a modification of the two-step method of Thompson and Appleman described above which was adapted for 96 well plate format. The effect of the PDE inhibitors was determined by assaying a fixed amount of the enzyme in the presence of test compound concentrations and a substrate concentration below that of the Km, so that Ki equals $IC_{50}$. The final assay volume was 110 µl with assay buffer (10 mM $MgCl_2$; 40 mM Tris.HCl; pH 7.4). Reactions were initiated with enzyme and incubated with ($^3$H)—substrate and substance for 20 minutes at 30° C. The reaction was terminated by denaturing the enzyme (heating the reaction to 70° C. for 2 minutes). The reaction was then cooled at 4° C. for 10 minutes before the addition of snake venom (*Crotalus atrox*, 0.2 mg/ml) for 10 minutes at 30° C., thus allowing non-specific hydrolysis of the tritiated substrate. Separation of the remaining unhydrolysed cyclic nucleotide was achieved by a batch binding of the mixture to activated Dowex (200 µl) anion exchange resin. The anion exchange resin bound the charged nucleotides, leaving only hydrolysed ($^3$H) substrate in the soluble fraction. The soluble fraction (50 µl) was then added to microscint-20 (200 µl) and counted on a Top Count Plate reader. Radioactivity units were plotted against inhibitor concentration and $IC_{50}$ values obtained using Graph Pad Prism software.

Alternatively, phosphodiesterase activity was measured by scintillation proximity assay (SPA) with [$^3$H]-cGMP as substrate. Purified PDE10 was diluted and stored in 25 mM Tris-Cl (pH 8.0)/100 mM NaCl/0.05% Tween 20/50% glycerol/3 mM DTT. Assays contained (final concentrations): 50 mM Tris-Cl (pH 7.5)/8.3 mM $MgCl_2$/1.7 mM EGTA/0.5 mg/ml BSA/5% DMSO and 2 ng PDE10 in a final volume of 0.1 mL. Inhibition was evaluated at 8 concentrations in duplicate. Reactions were initiated by addition of enzyme and were terminated after 20 minutes at 30° C. by the addition of 50 µl of SPA beads containing $Zn^{++}$. The mixture was shaken, allowed to settle for 3 hours, and counted in a Wallac plate counter. Results (net cpm) were fitted to a four parameter logistic model using Excel Solver®.

Further, the inhibition of other PDE enzymes by the PDE10 inhibitors was evaluated under the same conditions described above for PDE10 except the amount of enzyme added was optimized for each PDE. Fractional inhibition was evaluated at four concentrations (0.1, 1, 10, and 100 µM). In cases where inhibition at the highest concentration was less than 50%, the lower limit value in the logistic model was fixed to 0% activity.

In the above assay, compounds of this invention are PDE10 inhibitors with an $IC_{50}$ of 100 μM or less, generally less than 10 μM, and typically less than 1 μM. To this end, compounds 1-1, 2-1, 3-1, 4-1, 5-1, 6-1, 7-1, 8-1, 9-1, 10-1, 11-1, 12-1, 13-1, 14-1, 15-1, 16-1, 17-1, 18-1, 19-1, 20-1, 21-1, 22-1, 23-1, 25-1, 26-1, 27-1, 28-1, 29-1, 30-1, 31-1, 32-1, 33-1, 34-1, 35-1, 36-1, 37-1, 38-1, 39-1, 40-1, 41-1, 42-1, 43-1, 44-1, 45-1, 46-1, 47-1, 48-1, 49-1, 50-1, 51-1, 52-1, 53-1, 54-1, 55-1, 56-1, 57-1, 58-1, 59-1, 60-1, 61-1, 62-1, 63-1, 64-1, 65-1, 65-2, 65-3, 65-4, 65-5, 65-6, 65-7, 65-8, 65-9, 65-10, 65-11, 65-12, 65-13, 65-14, and 65-15 for example, were found to have $IO_{50}$ values of less than or equal to 1 μM.

Examples 67-77

Evaluation of Representative Compounds in Behavioral Models

Schizophrenia has been associated with dysfunctions of dopaminergic, glutamatergic and serotonergic neurotransmission. Psychostimulant drugs in these three classes, dopaminergic agonists (such as amphetamine and apomorphine), glutamatergic antagonists (such as phencyclidine (PCP) and ketamine), and serotonergic agonists (such as LSD and MDMA), all induce psychotomimetic states (e.g., hyperactivity and disruption of prepulse inhibition) in animals, that closely resemble schizophrenia symptoms in humans. Known antipsychotic drugs, including both typical antipsychotics (e.g., haloperidol) and atypical antipsychotics (e.g., olanzapine), reverse such psychotomimetic states in animals. Examples 67-77 described below evaluate representative compounds of the present invention in animal behavioral models to allow comparison of the resulting effect to that of known antipsychotics. Methods used in the Examples 67-77 are as follows.

Dosing of the compounds is by intraperitoneal (i.p.) injection or oral gavage (p.o.). Intraperitoneal injection is accomplished by restraining the animal, exposing the abdomen and inserting the needle just above the knees on the mouse's right side. Oral gavage is performed by restraining the animal in such a way that its head is tilted back and the esophagus is relatively straight. The gavage needle (20G×1.5", Cadence Science) is inserted into the mouth in line with the body and gently pushed along the esophagus and into the stomach. If resistance is encountered the needle is removed and reinserted.

Psychostimulant-induced hyperactivity is measured by injecting animals with PCP and monitoring the animals' activity levels in VersaMax chambers (Accuscan Instruments, Columbus, Ohio) measuring 40×40 cm. Locomotor activity is detected by photobeam breaks as the animal crosses each beam. The animal is placed in the center of the field and left undisturbed for 20 minutes to measure its spontaneous activity in a novel environment. Measurements used to assess locomotor activity include: horizontal activity, total distance traveled, vertical activity (rearing events—animal raises up on hindlimbs), rotation, stereotypy, and distance traveled in the center compared to total distance traveled (center: total distance ratio). The NMDA antagonist PCP induces a pychosis-like syndrome manifest as hyperactivity and increased stereotypic behavior. Known antipsychotics are able to reverse psychostimulant-induced hyperactivity and stereotypy.

Conditioned avoidance response (CAR) is a behavioral test to evaluate the antipsychotic effect of a test compound. It utilizes a shuttle box (Med Associates, St. Albans, Vt.) with two identical chambers separated by a retractable door. Each chamber is fitted with a metal grid floor that is capable of delivering electric shocks independently. A computer program is used to implement the testing paradigm as well as record the animal's movement between the two chambers through infrared beam sensors. The testing paradigm is as follows. A mouse is placed into one chamber. A light (conditioned stimulus, CS) comes on. Five seconds later, mild electric shocks (0.4 mA; (unconditioned stimulus, US) are delivered to the chamber where the mouse is located (as detected by infrared beams) until the mouse escapes to the adjacent chamber or until 10 sec has elapsed. The US and CS always co-terminate. With randomized inter-trial intervals averaging 15 sec, 30 such CS-US pairing trials are given to each mouse each day. For each trial, an escape response is registered if the mouse crosses to the other chamber after being shocked (i.e., during the 10-sec US period), and an avoidance response is registered if the mouse crosses to the other chamber during the first 5-sec CS only period. The animals are trained in this paradigm for 30-40 days, during which the average percentage of avoidance responses will improve to 80-90%. This indicates that animals have learned to avoid the onset of footshocks by moving to the opposite chamber upon activation of the CS (light). These trained animals are then used for compound testing with the same paradigm. Known antipsychotics have been found to inhibit the conditioned avoidance response, and the ability of new compounds to inhibit this response is thought to be predictive of antipsychotic effects in humans.

Example 67

Reduction of PCP-Induced Hyperactivity by Compound 1-1

Figure 2:
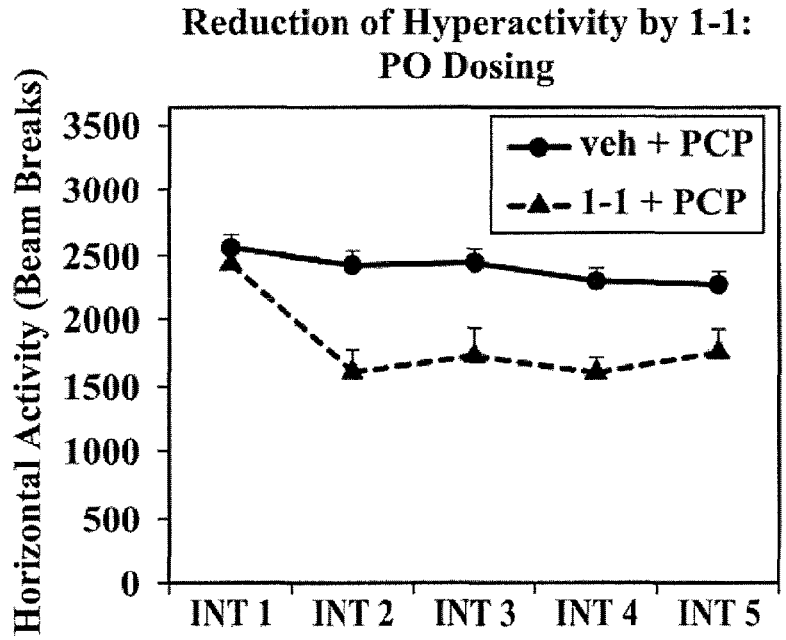
FIG. 2 illustrates that Compound 1-1 of the present invention (Example 1) administered by oral gavage significantly reduces hyperactivity of mice in a psychostimulant (PCP)-induced model of psychosis as compared to vehicle control.

Compound 1-1 (Example 1) was found to reduce PCP-induced hyperactivity, as shown in FIGS. 1 and 2. C57BL/6 male mice were given either compound 1-1 or vehicle by intraperitoneal injection (FIG. 1) or oral gavage (FIG. 2). Twenty minutes (for i.p.) or forty minutes (for p.o.) later, they were injected with PCP (5 mg/kg, i.p.). Ten minutes later, the mice were placed in activity chambers and their locomotor activity in the horizontal dimension was monitored by infrared beam breaks for 20 min (5 consecutive 4-minute intervals (INT) as indicated). FIG. 1 shows that compound 1-1 (10 mg/kg) significantly reduces the hyperactivity induced by PCP, as seen by comparison to the vehicle+PCP control (p=0.0088, n=8 per group, independent sample t-test). FIG. 2 shows that compound 1-1 is also effective when given by oral gavage (p=0.0045, n=8 per group, independent sample t-test)

Example 68

Reduction of PCP-Induced Hyperactivity by Compound 2-1

Figure 3:
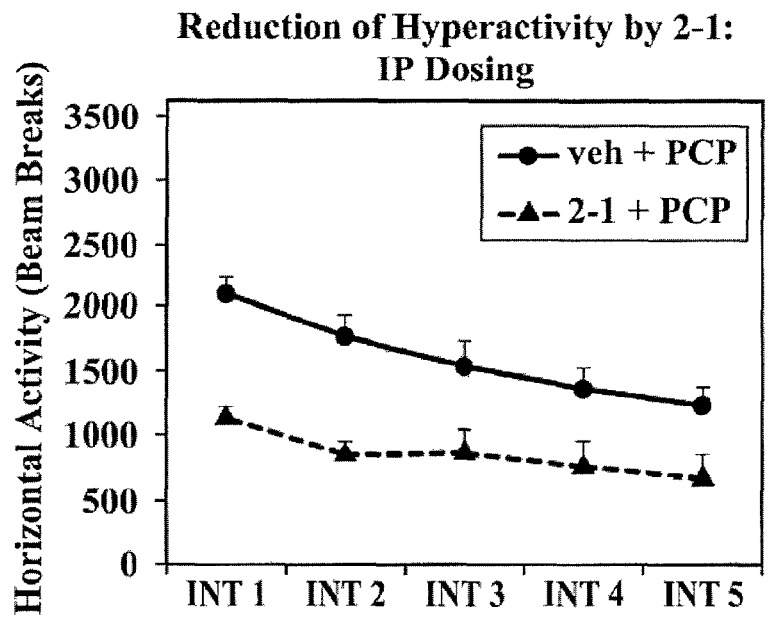
FIG. 3 illustrates that Compound 2-1 of the present invention (Example 2) administered by intraperitoneal injection significantly reduces hyperactivity of mice in a psychostimulant (PCP)-induced model of psychosis as compared to vehicle control.
Figure 4:
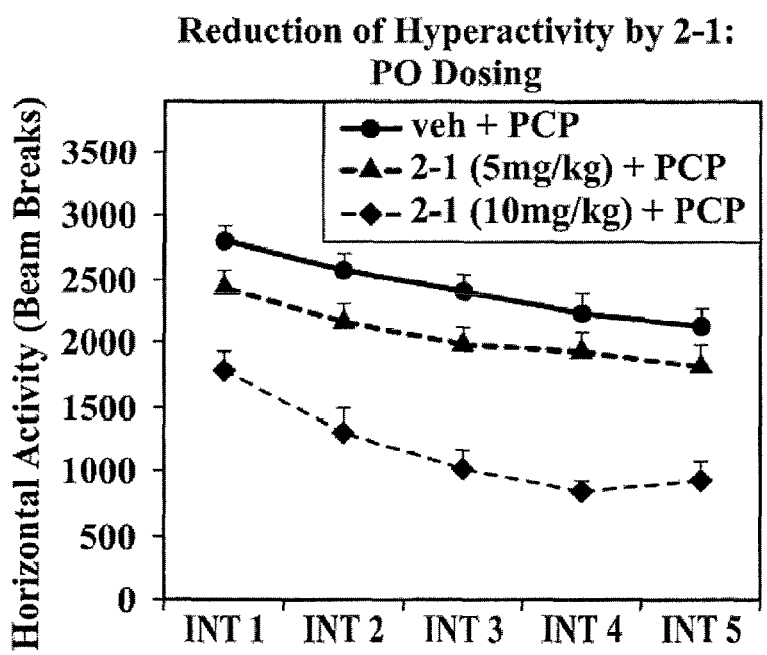
FIG. 4 illustrates that Compound 2-1 of the present invention (Example 2) administered by oral gavage significantly reduces hyperactivity of mice in a psychostimulant (PCP)-induced model of psychosis as compared to vehicle control.

Compound 2-1 (Example 2) was found to reduce PCP-induced hyperactivity, as shown in FIGS. 3 and 4. C57BL/6 male mice were given either compound 2-1 or vehicle by intraperitoneal injection (FIG. 3) or oral gavage (FIG. 4). Twenty minutes (for i.p.) or 40 minutes (for p.o.) later, they were injected with PCP (5 mg/kg, i.p.). Ten minutes later, the mice were placed in activity chambers and their locomotor activity in the horizontal dimension was monitored by infrared beam breaks for 20 min (5 consecutive 4-minute intervals (INT) as indicated). FIG. 3 shows that compound 2-1 (10 mg/kg) significantly reduces the hyperactivity induced by PCP, as seen by comparison to the vehicle+PCP control (p=0.0021, n=8 per group, independent sample t-test). FIG. 4 shows that compound 2-1 is also effective when given by oral gavage (p=0.000005 for 10 mg/kg dose, n=8 per group, independent sample t-test)

Example 69

Reduction of Conditioned Avoidance Response by Compound 2-1

Figure 5:
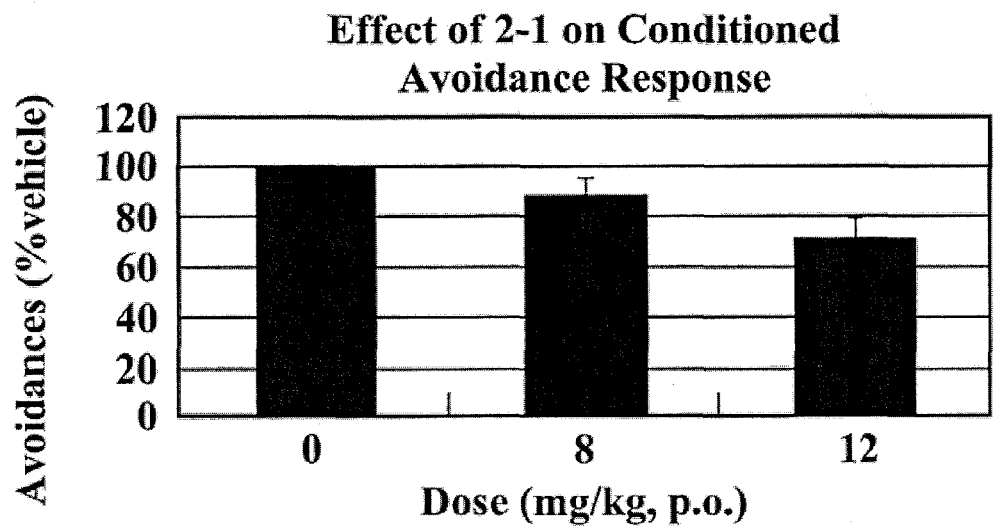
FIG. 5 illustrates that Compound 2-1 of the present invention (Example 2) significantly reduces a conditioned avoidance response (CAR) in mice trained in a CAR model of psychosis as compared to vehicle control.

Compound 2-1 (Example 2) was found to reduce Conditioned Avoidance Responses (CAR), as shown in FIG. 5. C57BL/6 male mice were trained in the CAR paradigm to predict and avoid the noxious stimulus (foot shock), reaching a plateau of approximately 25 avoidance responses per 30 trials each day. The mice were then given either vehicle or compound 2-1 via oral gavage, 30 minutes before testing for 30 trials in the CAR paradigm. Vehicle treatment and compound treatment were given to the same animals on alternating days, and the effect of compound in reducing avoidance response was analyzed through within-subject comparison (paired t-test). Vehicle exposure does not alter the avoidance response of these trained animals. FIG. 5 shows that compound 2-1 (12 mg/kg) significantly reduces the number of avoidance response (p=0.0048, n=7 per group, paired t-test).

Example 70

Reduction of PCP-Induced Hyperactivity by Compound 11-1

Figure 6:
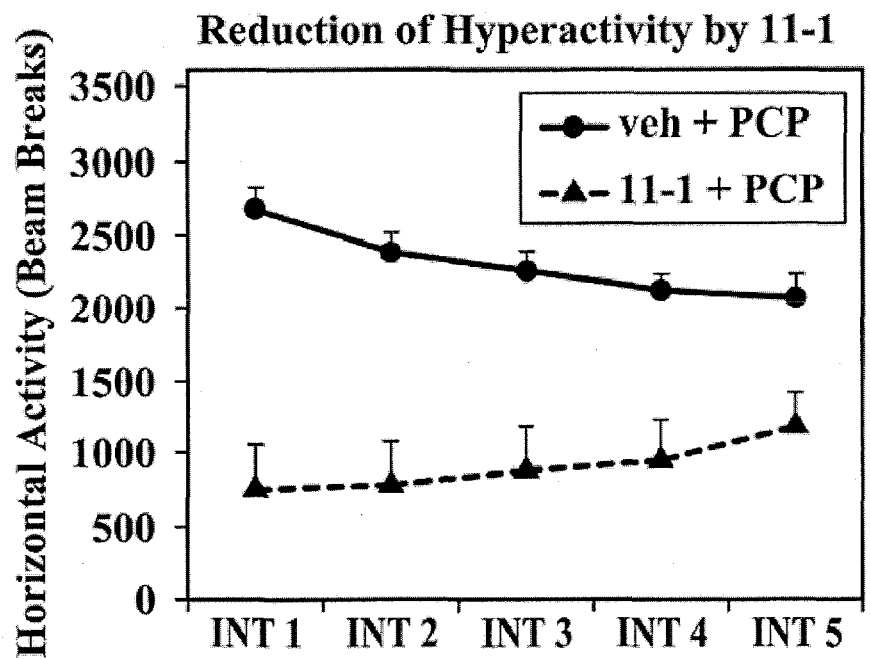
FIG. 6 illustrates that Compound 11-1 of the present invention (Example 11) administered by intraperitoneal injection significantly reduces hyperactivity of mice in a psychostimulant (PCP)-induced model of psychosis as compared to vehicle control.

Compound 11-1 (Example 11) was found to reduce PCP-induced hyperactivity, as shown in FIG. 6. C57BL/6 male mice were given either compound 11-1 or vehicle by intraperitoneal injection. Five minutes later they were injected with PCP (5 mg/kg, i.p.). Ten minutes later, the mice were placed in activity chambers and their locomotor activity in the horizontal dimension was monitored by infrared beam breaks for 20 min (5 consecutive 4-minute intervals (INT) as indicated). FIG. 6 shows that compound 11-1 (10 mg/kg) significantly reduces the hyperactivity induced by PCP, as seen by comparison to the vehicle+PCP control (p=0.00040, n=8 per group, independent sample t-test).

Example 71

Reduction of Conditioned Avoidance Response by Compound 34-1

Figure 7:
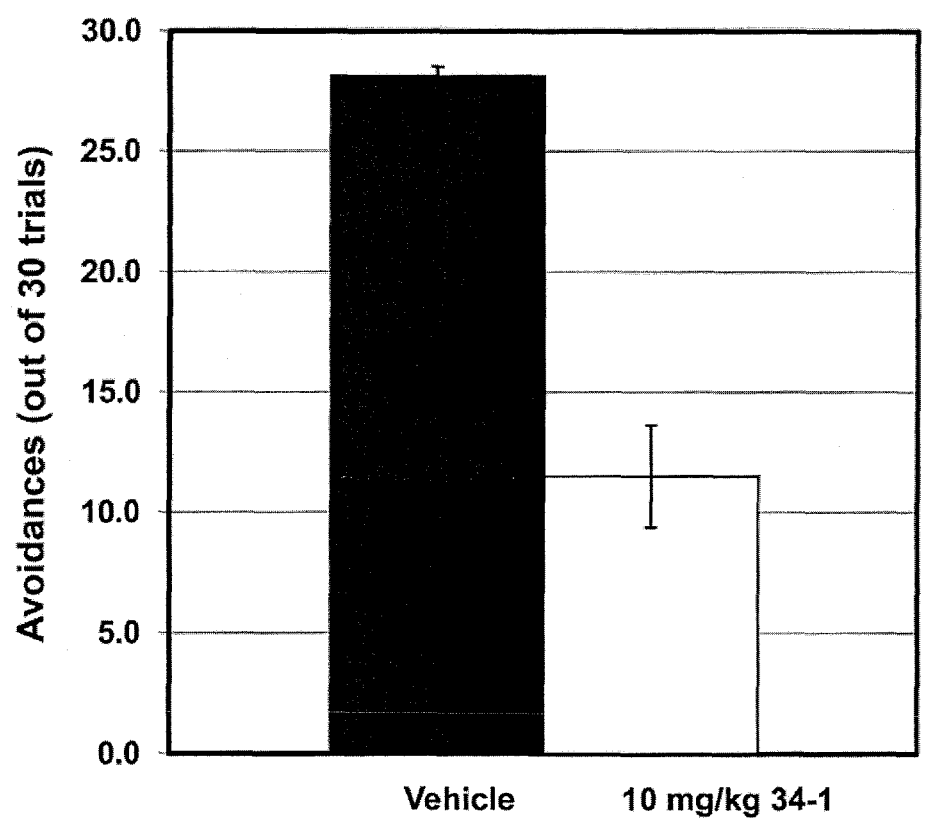
FIG. 7 illustrates that Compound 34-1 of the present invention (Example 34) significantly reduces a conditioned avoidance response (CAR) in mice trained in a CAR model of psychosis as compared to vehicle control.

Compound 34-1 (Example 34) was found to reduce Conditioned Avoidance Responses (CAR), as shown in FIG. 7. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (25 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 7 shows that compound 34-1 significantly reduces the number of avoidance responses at 10 mg/kg (p=0.0003, n=7 per group).

Example 72

Reduction of Conditioned Avoidance Response by Compound 36-1

Figure 8:
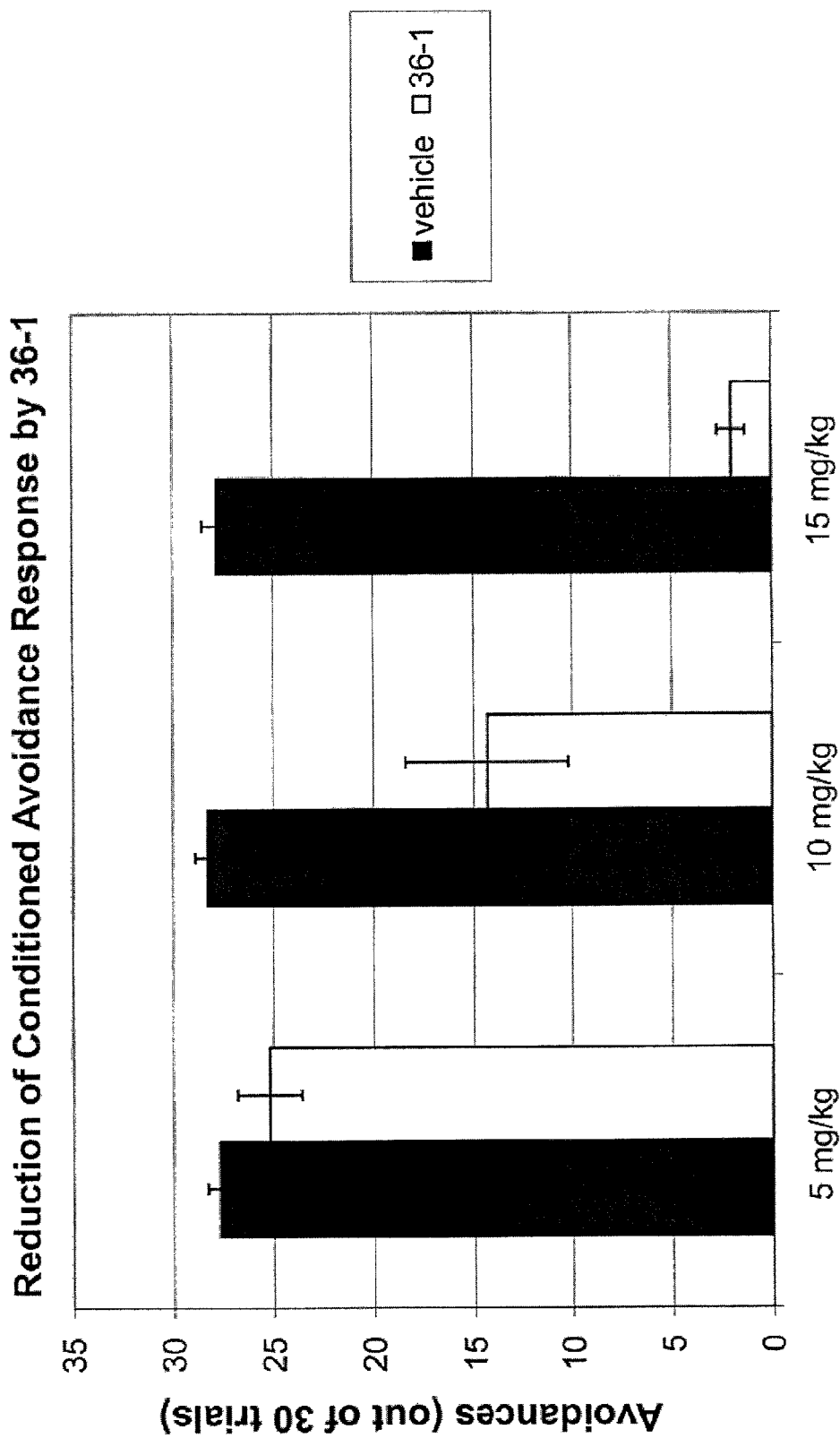
FIG. 8 illustrates that Compound 36-1 of the present invention (Example 36) significantly reduces a conditioned avoidance response (CAR) in mice trained in a CAR model of psychosis as compared to vehicle control.

Compound 36-1 (Example 36) was found to reduce Conditioned Avoidance Responses (CAR), as shown in FIG. 8. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (25 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 8 shows that compound 36-1 significantly reduces the number of avoidance responses at 15 mg/kg (p=0.000014, n=5 per group) and shows a trend that did not reach significance at 5 and 10 mg/kg.

Example 73

Reduction of Conditioned Avoidance Response by Compound 47-1

Figure 9:
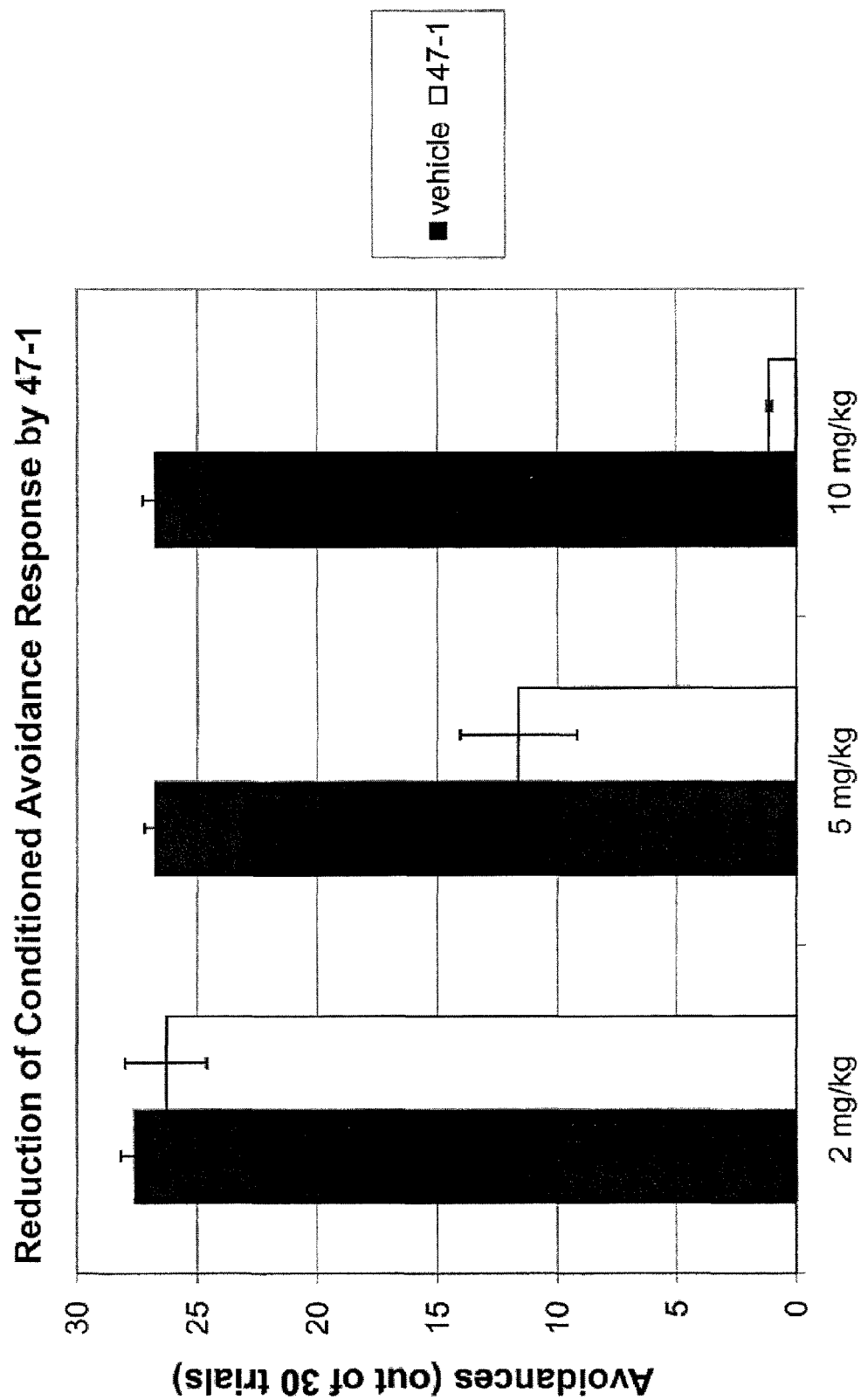
FIG. 9 illustrates that Compound 47-1 of the present invention (Example 47) significantly reduces a conditioned avoidance response (CAR) in mice trained in a CAR model of psychosis as compared to vehicle control.

Compound 47-1 (Example 47) was found to reduce Conditioned Avoidance Responses (CAR), as shown in FIG. 9. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (55 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 9 shows that compound 47-1 significantly reduces the number of avoidance responses at 5 and 10 mg/kg (p=0.0002 and p=3.3 E-10, respectively, n=8 per group) and shows a trend that did not reach significance at 2 mg/kg.

Example 74

Reduction of Conditioned Avoidance Response by Compound 61-1

Figure 10:
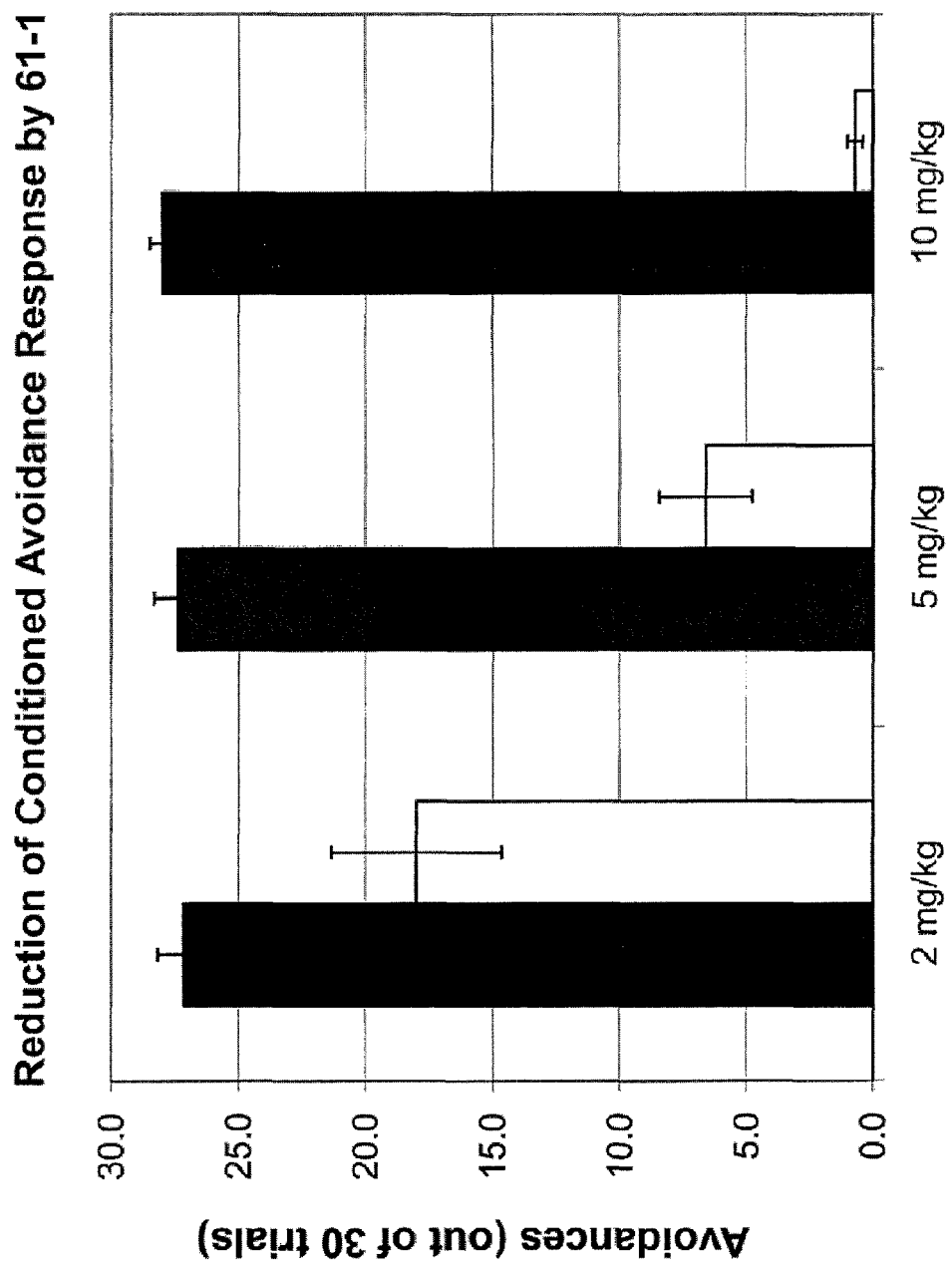
FIG. 10 illustrates that Compound 61-1 of the present invention (Example 61) significantly reduces a conditioned avoidance response (CAR) in mice trained in a CAR model of psychosis as compared to vehicle control.

Compound 61-1 (Example 61) was found to reduce Conditioned Avoidance Responses (CAR), as shown in FIG. 10. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (55 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 10 shows that compound 61-1 significantly reduces the number of avoidance responses at 2, 5, and 10 mg/kg (p=0.015, p=0.00008 and p=2.1 E-7, respectively, n=5 per group).

Example 75

Reduction of Conditioned Avoidance Response by Compound 63-1

Figure 11:
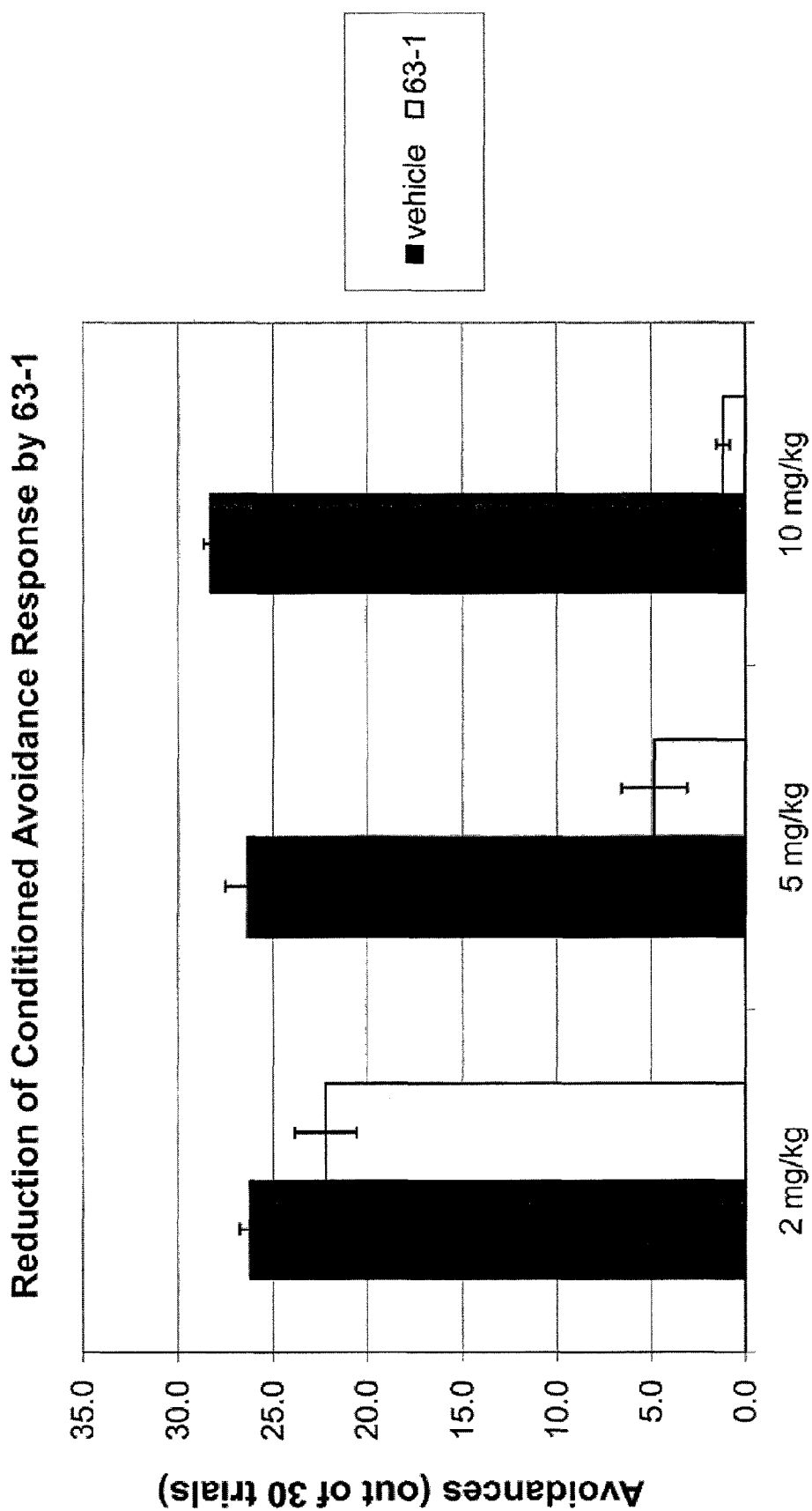
FIG. 11 illustrates that Compound 63-1 of the present invention (Example 63) significantly reduces a conditioned avoidance response (CAR) in mice trained in a CAR model of psychosis as compared to vehicle control.

Compound 63-1 (Example 63) was found to reduce Conditioned Avoidance Responses (CAR), as shown in FIG. 11. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (55 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 11 shows that compound 63-1 significantly reduces the number of avoidance responses at 2, 5, and 10 mg/kg (p=0.0099, p=0.00011, and p=6.6 E-16 respectively, n=6 per group).

Example 76

Reduction of Conditioned Avoidance Response by Compound 49-1

Figure 12:
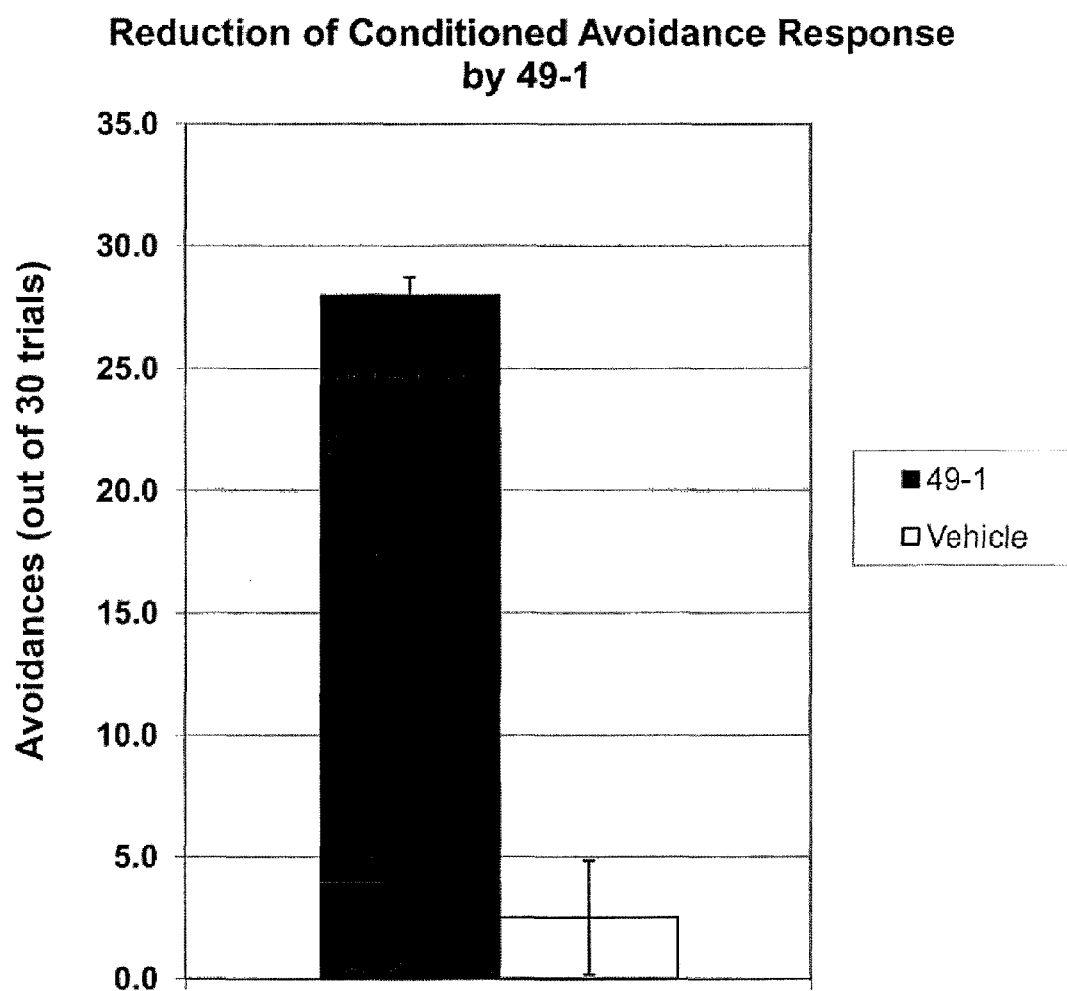
FIG. 12 illustrates that Compound 49-1 of the present invention (Example 49) significantly reduces a conditioned avoidance response (CAR) in mice trained in a CAR model of psychosis as compared to vehicle control.

Compound 49-1 (Example 49) was found to reduce Conditioned Avoidance Responses (CAR), as shown in FIG. 12. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (55 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 12 shows that compound 49-1 significantly reduces the number of avoidance responses at 10 mg/kg (p=5.7 E-9, n=8 per group).

Example 77

Reduction of Conditioned Avoidance Response by Compound 65-10

Figure 13:
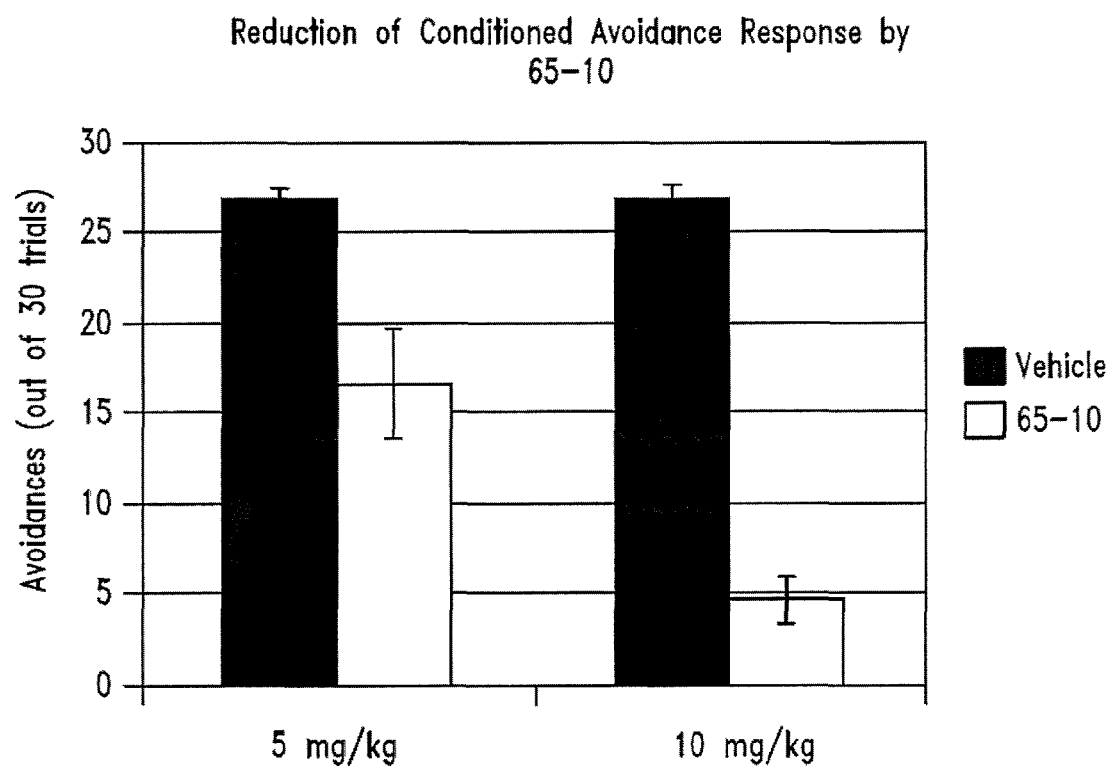
FIG. 13 illustrates that Compound 65-10 of the present invention (Example 65, Table 1) significantly reduces a conditioned avoidance response (CAR) in mice trained in a CAR model of psychosis as compared to vehicle control.

Compound 65-10 (Example 65, Table 1) was found to reduce Conditioned Avoidance Responses (CAR), as shown in FIG. 13. C57BL/6 male mice were trained in the CAR paradigm to predict and avoid the noxious stimulus (foot shock), reaching a plateau of approximately 25-28 avoidance responses per 30 trials ("training plateau") each day. The mice were then given either vehicle or compound (55 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 13 shows that compound 65-10 significantly reduces the number of avoidance responses at 5 and 10 mg/kg (p=0.0145 and p=0.00011; n=8 per group).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

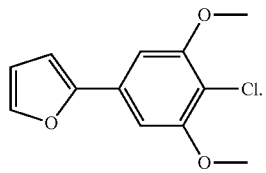 [SMILES: COc1cc(-c2ccco2)cc(OC)c1Cl]

* * * * *

UNITED STATES PATENT AND TRADEMARK OFFICE
CERTIFICATE OF CORRECTION

PATENT NO. : 9,102,643 B2
APPLICATION NO. : 14/177952
DATED : August 11, 2015
INVENTOR(S) : Cutshall et al.

It is certified that error appears in the above-identified patent and that said Letters Patent is hereby corrected as shown below:

In the Specification

| COLUMN | LINE | ERROR |
|---|---|---|
| 9 | 36 | "$^{36}$C" should read --$^{36}$Cl-- |
| 55 | 43 | "[D]" should read --[d]-- |
| 57 | 33 | "[M+1-1]$^+$." should read --[M+H]$^+$.-- |
| 67 | 23 | "[M+1-1]$^+$." should read --[M+H]$^+$.-- |
| 78 | 35 | Replace the compound with the following: |

| | | |
|---|---|---|
| 96 | 14 | "NH$_2$OH.HCl" should read --NH$_2$OH·HCl-- |
| 96 | 18 | "(Z)-2-(1-ethoxyethoxy)-N-hydroxy" should read --(Z)-2-(1-ethoxyethoxy)-N'-hydroxy-- |
| 96 | 44 | "(Z)-2-(1-ethoxyethoxy)-N-hydroxy" should read --(Z)-2-(1-ethoxyethoxy)-N'-hydroxy-- |
| 119 | 15 | "10$_{50}$" should read --IC$_{50}$-- |

Signed and Sealed this
Third Day of May, 2016

Michelle K. Lee
*Director of the United States Patent and Trademark Office*